US006951852B2

(12) United States Patent
Miller et al.

(10) Patent No.: US 6,951,852 B2
(45) Date of Patent: Oct. 4, 2005

(54) 2-PHENYL-1-[4-(2-AMINOETHOXY)-BENZYL]-INDOLES AS ESTROGENIC AGENTS

(75) Inventors: Chris P. Miller, Strafford, PA (US); Michael D. Collini, Clifton Heights, PA (US); Bach D. Tran, Baltimore, MD (US); Arthur A. Santilli, Havertown, PA (US)

(73) Assignee: Wyeth, Madison, NJ (US)

( * ) Notice: Subject to any disclaimer, the term of this patent is extended or adjusted under 35 U.S.C. 154(b) by 45 days.

(21) Appl. No.: 10/692,777

(22) Filed: Oct. 24, 2003

(65) Prior Publication Data

US 2004/0229932 A1 Nov. 18, 2004

Related U.S. Application Data

(60) Continuation of application No. 10/617,096, filed on Jul. 10, 2003, now Pat. No. 6,787,538, which is a continuation of application No. 10/192,069, filed on Jul. 10, 2002, now abandoned, which is a continuation of application No. 09/974,416, filed on Oct. 10, 2001, now abandoned, which is a division of application No. 09/388,581, filed on Sep. 2, 1999, now Pat. No. 6,326,367, which is a division of application No. 08/833,271, filed on Apr. 4, 1997, now Pat. No. 5,998,402.
(60) Provisional application No. 60/015,553, filed on Apr. 19, 1996.

(51) Int. Cl.$^7$ .......................... A61P 19/00; A61P 19/02
(52) U.S. Cl. ................. 514/217.07; 514/323; 514/414; 514/415
(58) Field of Search ........................... 514/217.07, 323, 514/414, 415

(56) References Cited

U.S. PATENT DOCUMENTS

| | | | |
|---|---|---|---|
| 4,943,572 A | 7/1990 | von Angerer et al. |
| 5,023,254 A | 6/1991 | von Angerer et al. |
| 5,124,335 A | 6/1992 | Patchett et al. |
| 5,389,641 A | 2/1995 | Naka et al. |
| 5,496,844 A | 3/1996 | Inai et al. |
| 5,998,402 A | 12/1999 | Miller et al. |
| 6,127,404 A | 10/2000 | Miller et al. |
| 6,225,308 B1 | 5/2001 | Miller et al. |
| 6,232,307 B1 | 5/2001 | Miller et al. |
| 6,291,451 B1 | 9/2001 | Miller et al. |
| 6,326,367 B1 | 12/2001 | Miller et al. |
| 6,787,538 B2 | 9/2004 | Miller et al. |
| 2004/0110824 A1 | 6/2004 | Miller et al. |

FOREIGN PATENT DOCUMENTS

| | | |
|---|---|---|
| EP | 0 639 567 | 2/1995 |
| WO | WO 93/10741 | 6/1993 |
| WO | WO 93/23374 | 11/1993 |
| WO | WO 95/17383 | 6/1995 |
| WO | WO 96/03375 | 2/1996 |
| WO | WO 00/51983 | 9/2000 |

OTHER PUBLICATIONS von Angerer et al., Amer. Chem. Soc., 2635–2640, 1990.

von Angerer et al., Amer. Chem. Soc., 132–136, 1986.

Biberger et al., J. Steroid Biochem. Molec. Biol, 58(1), 31–43, 1996.

Henderson et al., Ann. N.Y. Aca. Sci., pp. 176, 177 and 189, 1995.

Oparil, "Hypertension in Postmenopausal Women: Pathology and Management", EMBASE 95:283951, 1995.

Biberger, "2–Phenylindoles with Sulfer Containing Side Chains", CA 125:316191, 1996.

von Angerer et al., J. Med. Chem., 27, 1439–1447, 1984.

*Primary Examiner*—Bruck Kifle
(74) *Attorney, Agent, or Firm*—Howson and Howson

(57) ABSTRACT

The present invention relates to new 2-Phenyl-1-[4-(2-Aminoethoxy)-Benzyl]-Indole compounds having the general structures below:

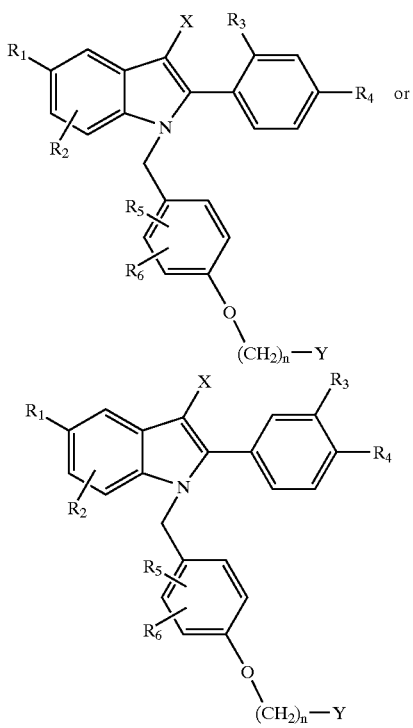

which are useful in the treatment or inhibition of osteoarthritis.

5 Claims, No Drawings

2-PHENYL-1-[4-(2-AMINOETHOXY)-BENZYL]-INDOLES AS ESTROGENIC AGENTS

This application is a continuation application of U.S. Ser. No. 10/617,096, filed Jul. 10, 2003, now U.S. Pat. No. 6,787,538 which is a continuation application of U.S. Ser. No. 10/192,069, filed Jul. 10, 2002, now abandoned which is a continuation application of U.S. Ser. No. 09/974,416, filed Oct. 10, 2001, now abandoned which is a divisional application of U.S. Ser. No. 09/388,581, filed Sep. 2, 1999, now U.S. Pat. No. 6,326,367 which is a divisional application of U.S. Ser. No. 08/833,271 (now U.S. Pat. No. 5,998,402, filed Apr. 4, 1997, which claims priority from U.S. Provisional Application 60/015,553, filed Apr. 19, 1996.

The present invention relates to new 2-Phenyl-1-[4-(2-Aminoethoxy)-Benzyl]-Indole compounds which are useful as estrogenic agents, as well as pharmaceutical compositions and methods of treatment utilizing these compounds.

BACKGROUND OF THE INVENTION

The use of hormone replacement therapy for bone loss prevention in post-menopausal women is well precedented. The normal protocol calls for estrogen supplementation using such formulations containing estrone, estriol, ethynyl estradiol or conjugated estrogens isolated from natural sources (i.e. Premarin® conjugated estrogens from Wyeth-Ayerst). In some patients, therapy may be contraindicated due to the proliferative effects of unopposed estrogens (estrogens not given in combination with progestins) have on uterine tissue. This proliferation is associated with increased risk for endomemosis and/or endometaial cancer. The effects of unopposed estrogens on breast tissue is less clear, but is of some concern. The need for estrogens which can maintain the bone sparing effect while minimizing the proliferative effects in the uterus and breast is evident. Certain nonsteroidal antiestrogens have been shown to maintain bone mass in the ovariectomized rat model as well as in human clinical trials. Tamoxifen (sold as Novadex® brand tamoxifen citrate by Zeneca Pharmaceuticals, Wilmington, Del.), for example, is a useful palliative for the treatment of breast cancer and has been demonstrated to exert an estrogen agonist-like effect on the bone, in humans. However, it is also a partial agonist in the uterus and this is cause for some concern. Raloxifene, a benzothiophene antiestmgen, has been shown to stimulate uterine growth in the ovariectomized rat to a lesser extent than Tamoxifen while maintaining the ability to spare bone. A suitable review of tissue selective estrogens is seen in the article "Tissue-Selective Actions Of Estrogen Analogs", *Bone* Vol. 17, No. 4, Oct. 1995, 181S–190S.

The use of indoles as estrogen antagonists has been reported by Von Angerer, Chemical Abstracts, Vol. 99, No. 7 (1983), Abstract No. 53886u. Also, see, J. Med. Chem. 1990, 33, 2635–2640; J. Med. Chem. 1998, 30, 131–136. Also see Ger. Offen., DE 3821148 A1 891228 and WO 96/03375. These prior art compounds share some structural simlarities with the present compounds, but are functionally different. For compounds containing a basic amine, there is no phenyl group to ridgidify the side chain. The reported data for these compounds indicates that they may have a weaker binding to estrogen receptor than the compounds of the present invention and the reported compounds containing the basic side chain show some uterotrophic effect in the rat uterus. One compound from the listed family of compounds in WO 96/03375 possesses a benzyl group, but does not have a basic side chain. The majority of these compounds fall into a class of compounds best characterized as being "pure antiestrogens". Many of the compounds described presently, due to their particular side chain, act as pure antiestrogens in the uterus, however, show strong estrogenic action in the bone and cardiovascular systems. No such action is demonstrated for the related prior art compounds described herein.

WO A 95 17383 (Kar Bio AB) describes indole antiestrogens with long straight chains. Another related patent WO A 93 10741 describes 5-Hydroxyindole with a generic descriptor incorporating other side chains. WO 93/23374 (Otsuka Pharmaceuticals, Japan) describes compounds which differ from the present invention; where $R_3$ in the present formulas I and II, below, is defined as thioalkyl and the reference discloses no such compounds having chains from the indole nitrogen having the same structure as the ones provided by the present invention. Where the side chain claimed is similar to that described herein, the compounds are amides: Acylated indoles are not claimed in the present invention.

DESCRIPTION OF THE INVENTION

2-Phenylindoles of the general structure type shown in formulas (I) and (II) are estrogen agonists/antagonists useful for the treatment of diseases associated with estrogen deficiency. The compounds of the present invention show strong binding to the estrogen receptor. In vitro assays, including an Ishikawa alkaline phosphatase assay and an ERE transfection assay, show these compounds are antiestrogens with little to no intrinsic estrogenicity and they have proven capable of completely antagonizing the effects of 17β-estradiol while showing little or no uterine stimulation in a rat uterine assay when dosed alone. Additionally, some of these compounds are capable of inhibiting bone loss in an ovariectomized rat while showing little or no uterine stimulation. These compounds also decrease the weight gain normally seen in the ovariectomized animals as well as reduce total cholesterol levels.

The present invention includes compounds of the formulas I or II, below:

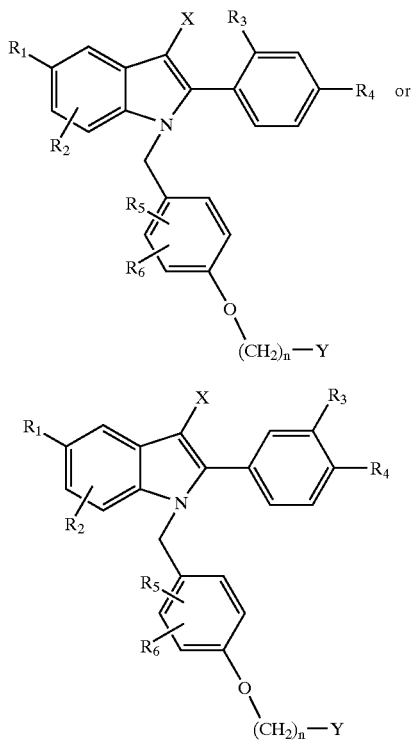

wherein:

R$_1$ is selected from H, OH or the C$_1$–C$_{12}$ esters (straight chain or branched) or C$_1$–C$_{12}$ (straight chain or branched or cyclic) alkyl ethers thereof, or halogens; or C$_1$–C$_4$ halogenated ethers including triflouromethyl ether and trichloromethyl ether.

R$_2$, R$_3$, R$_4$, R$_5$, and R$_6$ are independently selected from H, OH or the C$_1$–C$_{12}$ esters (straight chain or branched) or C$_1$–C$_{12}$ alkyl ethers (straight chain or branched or cyclic) thereof, halogens, or C$_1$–C$_4$ halogenated ethers including triflouromethyl ether and trichloromethyl ether, cyano, C$_1$–C$_6$ alkyl (straight chain or branched), or trifluoromethyl, with the proviso that, when R$_1$ is H, R$_2$ is not OH.

X is selected from H, C$_1$–C$_6$ alkyl, cyano, nitro, triflouromethyl, halogen;

n is 2 or 3;

Y is selected from:
a) the moiety:

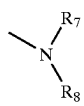

wherein R$_7$ and R$_8$ are independently selected from the group of H, C$_1$–C$_6$ alkyl, or phenyl optionally substituted by CN, C$_1$–C$_6$ alkyl (straight chain or branched), C$_1$–C$_6$ alkoxy (straight chain or branched), halogen, —OH, —CF$_3$, or —OCF$_3$;

b) a five-membered saturated, unsaturated or partially unsaturated heterocycle containing up to two heteroatoms selected from the group consisting of —O—, —NH—, —N(C$_1$C$_4$ alkyl)—, —N═, and —S(O)$_m$—, wherein, m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy(C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl;

c) a six-membered saturated, unsaturated or partially unsaturated heterocycle containing up to two heteroatoms selected from the group consisting of —O—, —NH—, —N(C$_1$C$_4$ alkyl)—, —N═, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy(C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl;

d) a seven-membered saturated, unsaturated or partially unsaturated heterocycle containing up to two heteroatoms selected from the group consisting of —O—, —NH—, —N(C$_1$C$_4$ alkyl)—, —N═, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy(C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl; or e) a bicyclic heterocycle containing from 6–12 carbon atoms either bridged or fused and containing up to two heteroatoms selected from the group consisting of —O—, —NH—, —N(C$_1$C$_4$ alkyl)—, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy(C$_1$–C$_4$)alkyl, —CO$_2$H—, —CN—, —CONHR$_1$—, NH$_2$—, C$_1$–C$_4$ alkylamino, di(C$_1$–C)alkylamino, —NHSO$_2$R$_1$—, —NHCOR$_1$—, —NO$_2$, and phenyl optionally substituted with 1–3 (C$_1$–C$_4$)alkyl;

and the pharmaceutically acceptable salts thereof.

The more preferred compounds of this invention are those having the general structures I or II, above, wherein:

R$_1$ is selected from H, OH or the C$_1$–C$_{12}$ esters or alkyl ethers thereof, halogen;

R$_2$, R$_3$, R$_4$, R$_5$, and R$_6$ are independently selected from H, OH or the C$_1$–C$_{12}$ esters or alkyl ethers thereof, halogen, cyano, C$_1$–C$_6$ alkyl, or trihalomethyl, preferably trifluoromethyl, with the proviso that, when R$_1$ is H, R$_2$ is not OH;

X is selected from H, C$_1$–C$_6$ alkyl, cyano, nitro, triflouromethyl, halogen;

Y is the moiety

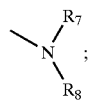

$R_7$ and $R_8$ are selected independently from H, $C_1$–$C_6$ alkyl, or combined by —$(CH_2)$p-, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy($C_1$–$C_4$)alkyl, —$CO_2H$, —CN, —$CONH(C_1$–$C_4)$, —$NH_3$, $C_1$–$C_4$ alkylamino, $C_1$–$C_4$ dialkylamino, —$NHSO_2$ $(C_1$–$C_4)$, —$NHCO(C_1$–$C_4)$, and —$NO_3$;
and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneamine or heptamethyleneamine rings.

The most preferred compounds of the present invention are those having the structural formulas I or II, above, wherein $R_1$ is OH; $R_2$–$R_6$ are as defined above; X is selected from the group of Cl, $NO_2$, CN, $CF_3$, or $CH_3$; and Y is the moiety

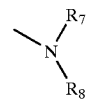

and $R_7$ and $R_8$ are concatenated together as —$(CH_2)_r$—, wherein r is an integer of from 4 to 6, to form a ring optionally substituted by up to three subsituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy($C_1$–$C_4$)alkyl, —$CO_2H$, —CN, —$CONH(C_1$–$C_4)$ alkyl, —$NH_2$, $C_1$–$C_4$ alkylamino, di($C_1$–$C_4$)alkylamino, —$NHSO_2(C_1$–$C_4)$alkyl, —$NHCO(C_1$–$C_4)$alkyl, and —$NO_2$;
and the pharmaceutically acceptable salts thereof.

In another embodiment of this invention, when $R_7$ and $R_8$ are concatenated together as —$(CH_2)$p-, wherein p is an integer of from 2 to 6, preferably 4 to 6, the ring so formed is optionally substituted with 1–3 substituents selected from a group containing $C_1$–$C_3$ alkyl, trifluoromethyl, halogen, hydrogen, phenyl, nitro, —CN.

The invention includes sulfate, sulfamates and sulfate esters of phenolic groups. Sulfates can be readily prepared by the reaction of the free phenolic compounds with sulfur trioxide complexed with an amine such as pyridine, trimethylamine, triethylamine, etc. Sulfamates can be prepared by treating the free phenolic compound with the desired amino or alkylamino or dialkylamino sulfamyl chloride in the presence of a suitable base such as pyridine. Sulfate esters can be prepared by reaction of the free phenol with the desired alkanesulfonyl chloride in the presence of a suitable base such as pyridine. Additionally, this invention includes compounds containing phosphates at the phenol as well as dialkyl phosphates. Phosphates can be prepared by ration of the phenol with the appropriate chlorophosphate. The dialkylphosphates can be hydrolyzed to yield the free phosphates. Phosphinates are also claimed where the phenol is reacted with the desired dialkylphosphinic chloride to yield the desired dialkylphosphinate of the phenol.

The invention includes acceptable salt forms formed from the addition reaction with either inorganic or organic acids. Inorganic acids such as hydrochloric acid, hydrobromic acid, hydroiodic acid, sufuric acid, phoshoric acid, nitric acid useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. It is known that compounds possessing a basic nitrogen can be complexed with many different acids (both protic and non-protic) and usually it is preferred to administer a compound of this invention in the form of an acid addition salt. Additionally, this invention includes quaternary ammonium salts of the compounds herein. These can be prepared by reacting the nucleophilic amines of the side chain with a suitably reactive alkylating agent such as an alkyl halide or benzyl halide.

Methods

Compounds of this invention can be synthesized in a general sense according to Scheme 1, below.

Scheme 1

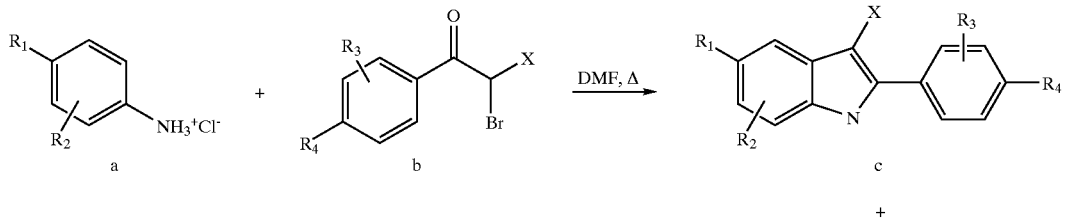

+

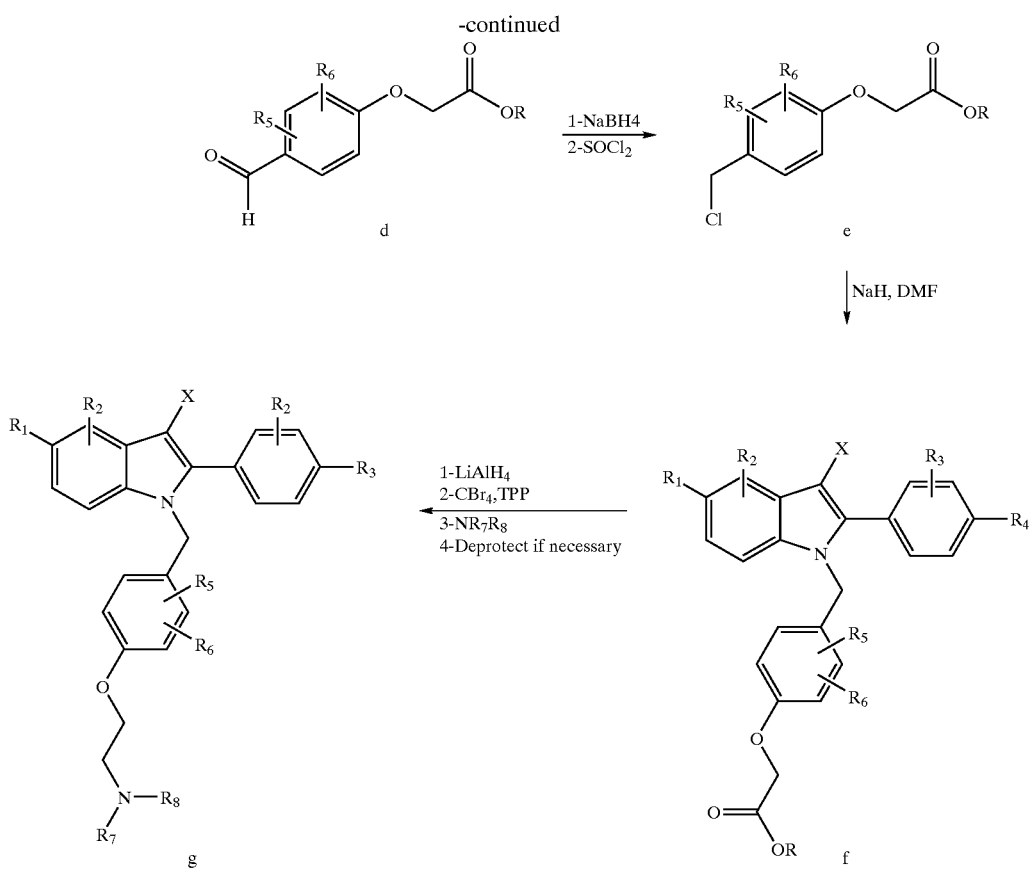

The initial indole synthesis is accomplished by heating an appropriately substituted alpha-bromo ketone (b) with the desired aniline (a) in DMF to form the indole (c). The product is then alkylated with a benzyl chloride (e) to give the substituted indole (f). The benzyl chloride (e) can be readily prepared from the aldehyde (d) in 2 steps as given. Product (g) can be prepared from (f) by reduction of the ester, conversion of the alcohol to a bromide, displacement of the bromide with the desired amine in a suitable solvent such as THF or DMF, and finally, deprotection if necessary. Deprotection is necessary when either $R_1$ or $R_2$ or both is a protected phenol. The preferred protecting group is a benzyl group which can be conveniently removed by several conventional methods, especially hydrogenolysis.

For the synthesis of compounds with X=H, halogen, trifluoromethyl, cyano, nitro, an alternative synthesis shown in scheme 2 may be preferable. The formation of halogens at the 3-position can be easily performed with such reagents as N-chlorosuccinamide, N-bromosuccinamide, or N-iodosuccinamide. A 3-Iodoindole compound obtained can be used as a precursor to the 3-trifluoromethyl compound by a coupling reaction utilizing a palladium catalyst and bis-trifluoromethyl mercury (II). A compound with a cyano group in the 3-position can be prepared by electrophilic cyanation or alternatively the 3-position can be formylated (with a formyl iminium salt, for example) then the formyl group converted to an oxime and subsequently dehydrated to a nitrile. Alternatively, the 3-cyano compound can be synthesized by reaction of the 3-unsubstituted indole with chlorosulfonylisocyanate followed by trimethylamine. A compound with the nitro group in the 3-position can be prepared by treating the indole with sodium nitrite and acetic acid. One skilled in the art recognizes these routes are not limiting and other routes are also available.

Scheme 2

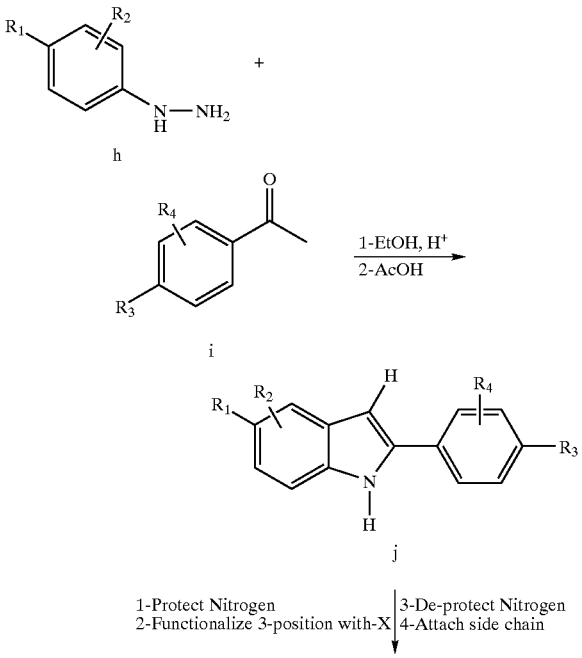

-continued
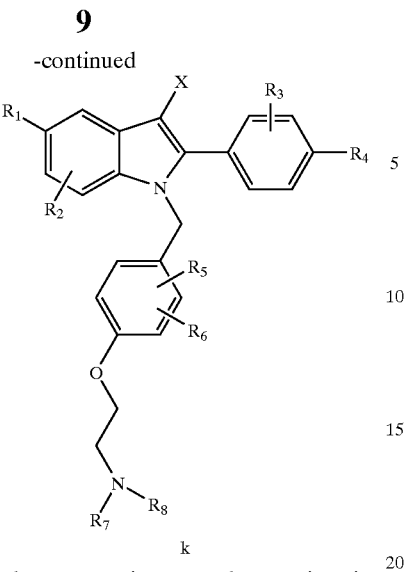
Synthesis of selected representative examples are given in the following schemes:
Scheme 3
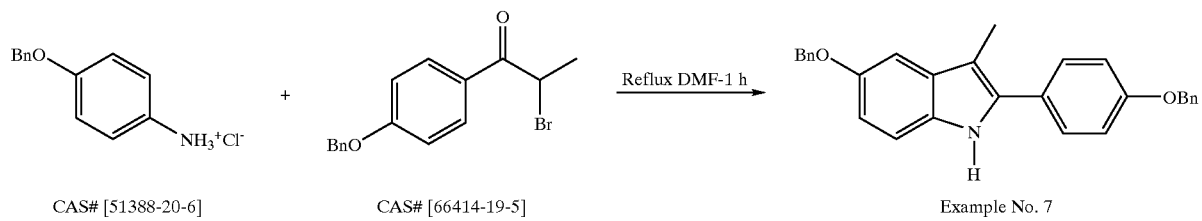
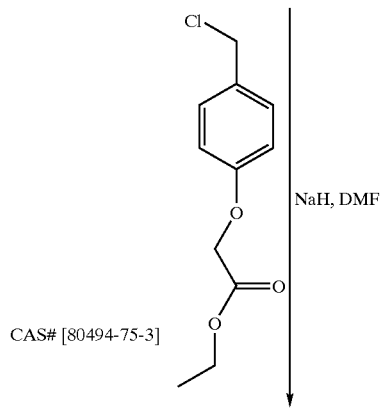

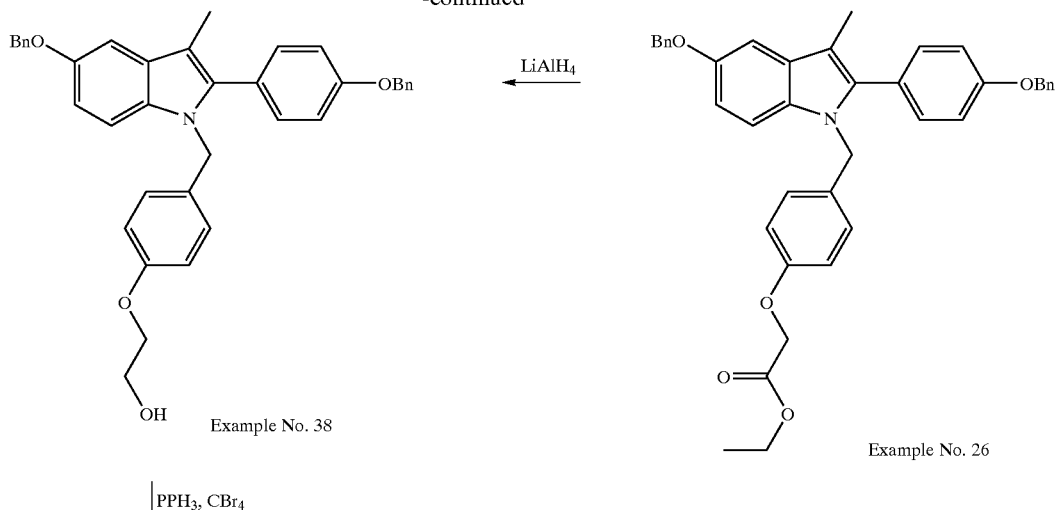
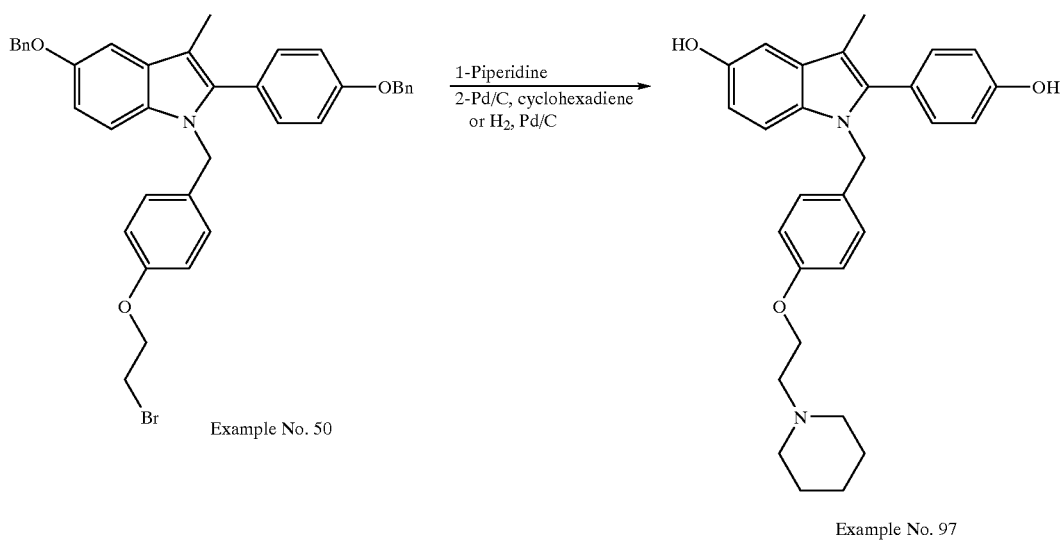
The synthesis of analogues with a 3-carbon chain (example No. 166) between the oxygen and the basic amine can be accomplished as shown in scheme 4.
Scheme 4
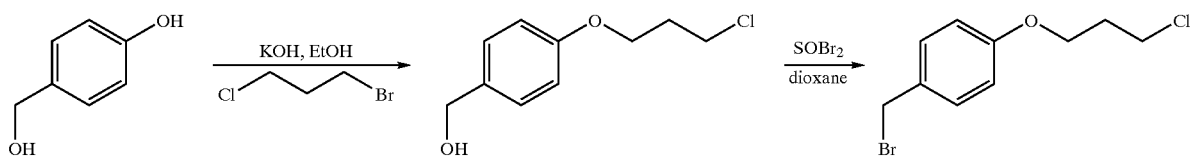

-continued
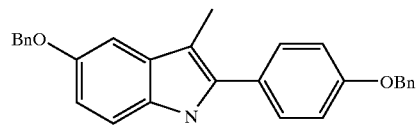
Example No. 7
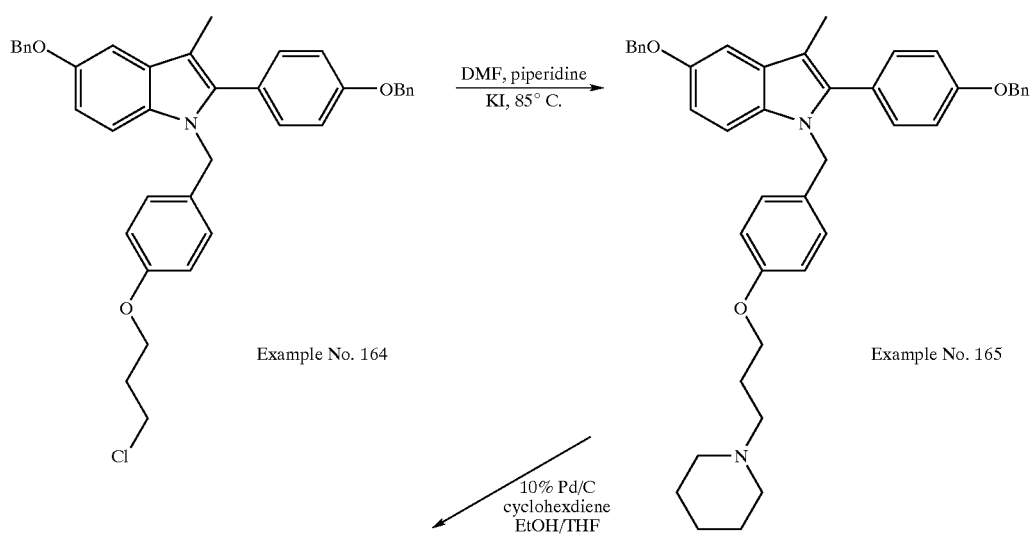
Example No. 164
Example No. 165
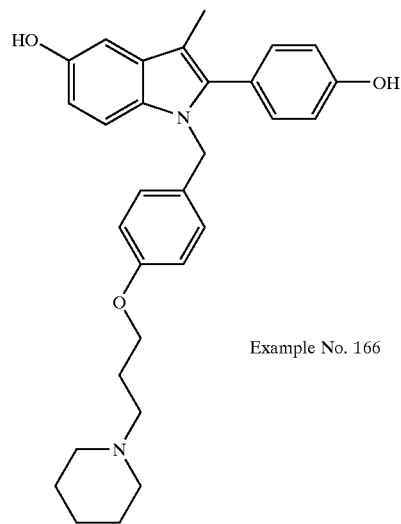
Example No. 166

The synthetic procedure shown in scheme 4 may be used for compounds with two carbon chains analogous to example No. 97 in scheme 3. This is shown in scheme 4a for the synthesis of example No. 127.
Scheme 4a
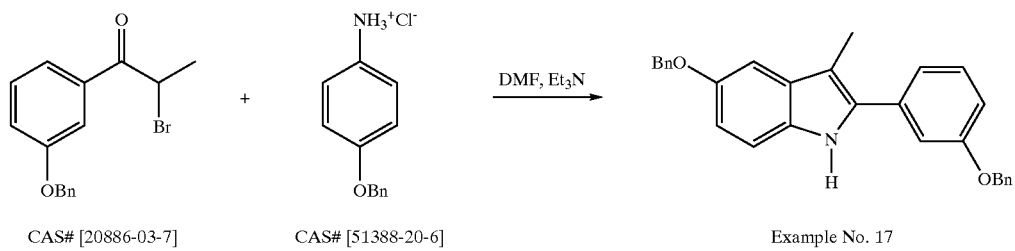
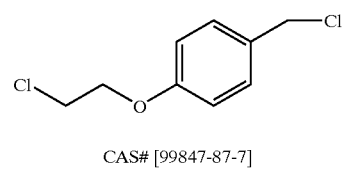
CAS# [99847-87-7]
NaH | DMF
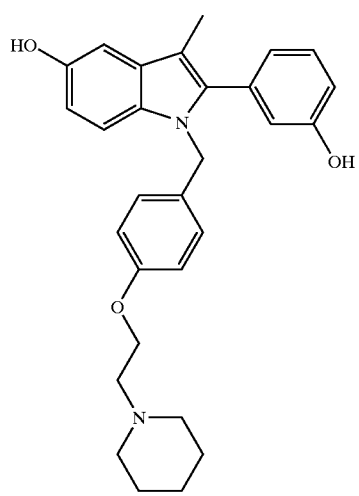
Example No. 127
← Continue as in scheme 4
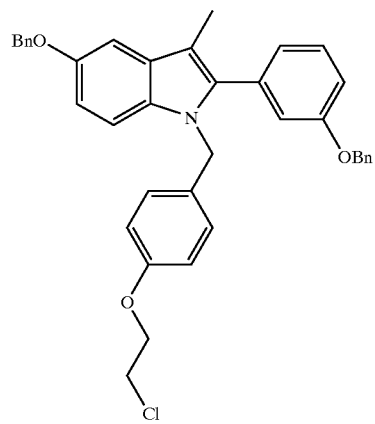
Example No. 58

The synthesis of indoles with alternative substituents (CN, Cl) at the 3-position of the indole both utilize the 3-unsubstituted indole No. 141 for a precursor. The indole is synthesized by the Fisher method utilizing the hydrazone derived from the condensation of 4-benzyloxyacetophenone CAS No. [54696-05-8] and 4-benzyloxyphenylhydrazine CAS No. [51145-58-5]. The hydrazone No. 140 is then cyclized in acetic acid using zinc chloride to afford the desired indole No. 141. This synthesis can be seen in scheme 5.

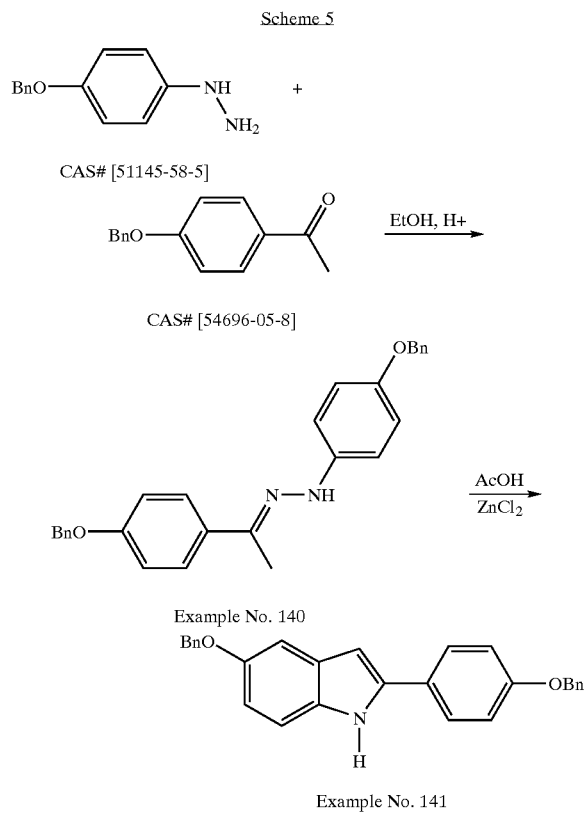

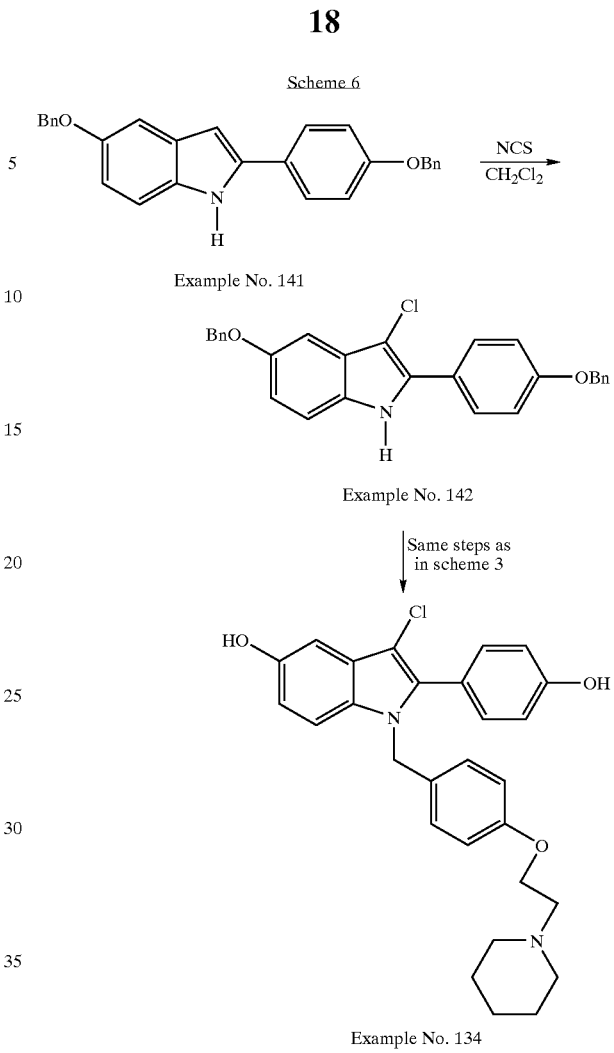

The synthesis of 3-Chloroindole compounds is demonstrated for example No. 134 and shown, infra, in scheme 6. The indole No. 141 from scheme 5 is chlorinated with N-chlorosuccinamide. The 3-Chloroindole No. 142, thus obtained, is taken to the final product in analogous fashion to that shown in scheme 3.

3-Cyano analogues are synthesized form the precursor indole No. 141 as shown in Scheme 7. Reaction of the precursor indole No. 141 with chlorosulfonyl isocyanate followed by addition of triethylamine yields the 3-Cyanoindole No. 155. The side chain is made by conversion of the benzylic alcohol of CAS No. [111728-87-1] to the benzylic bromide No. 156 using thionyl bromide in THF. The indole is alkylated by the side chain in DMF using sodium hydride to give the intermediate No. 157. This can then be taken to the final product No. 138 in an analogous fashion to that shown in scheme 4.

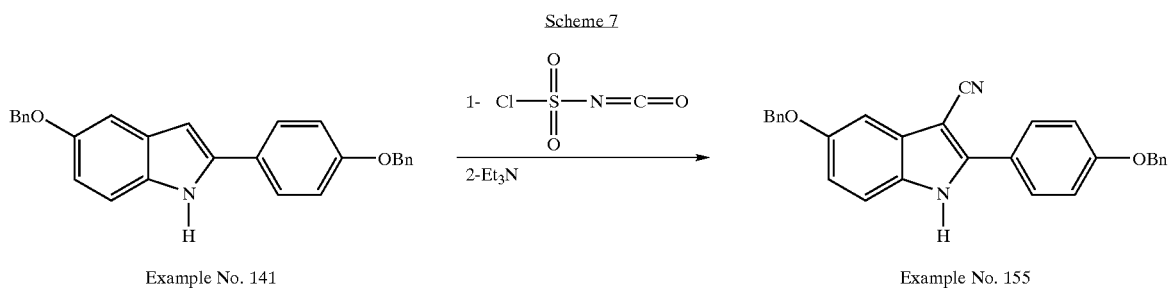

19

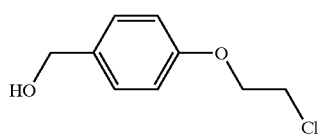

[111728-87-1P]

-continued
1-SOBr₂ / THF →

20

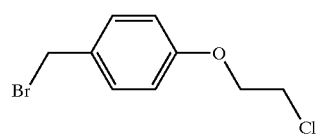

Example No. 156

↓ NaH DMF

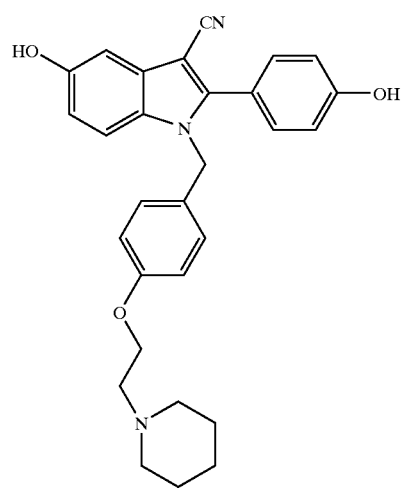

Example No. 138

← Finish as in Scheme 4

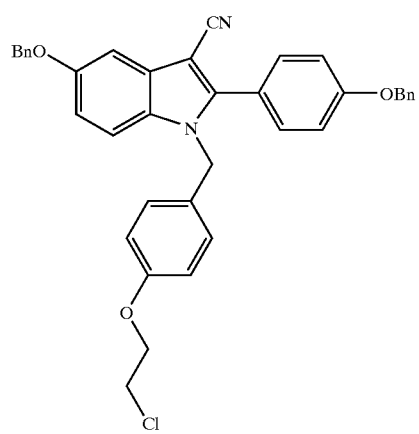

Example No. 157

The compounds of the invention are selective estrogen agonists and display high affinity for the estrogen receptor. Unlike many estrogens, however, many of these compounds do not cause increases in uterine wet weight. These compounds are antiestrogenic in the uterus and can completely antagonize the trophic effects of estrogen agonists in uterine tissue. Due to the tissue selective nature of these compounds, they are useful in treating or preventing in a mammal disease states or syndromes which are caused or associated with an estrogen deficiency (in certain tissues such as bone or cardiovascular) or an excess of estrogen (in the uterus or mammary glands). They may also be used in methods of treatment for diseases or disorders which results from proliferation or abnormal development, actions or growth of endometrial or endometrial-like tissues.

The present compounds have the ability to behave like estrogen agonists by lowering cholesterol and preventing bone loss. These compounds are useful for treating many maladies which result from estrogen effects and estrogen excess or deficiency including osteoporosis, prostatic hypertrophy, male pattern baldness, vaginal and skin atrophy, acne, dysfunctional uterine bleeding, endometrial polyps, benign breast disease, uterine leiomyomas, adenomyosis, ovarian cancer, infertility, breast cancer, endometriosis, endometrial cancer, polycystic ovary syndrome, cardiovascular disease, contraception, Alzheimer's disease, cognitive decline and other CNS disorders, as well as certain cancers including melanoma, prostrate cancer, cancers of the colon, CNS cancers, among others. Additionally, these compounds can be used for contraception in pre-menopausal women, as well as hormone replacement therapy in post-menopausal women or in other estrogen deficiency states where estrogen supplementation would be beneficial. They may also be used in disease states where amenorrhea is advantageous, such as leukemia, endometrial ablations, chronic renal or hepatic disease or coagulation diseases or disorders.

The compounds of this invention may also be used in methods of treatment for and prevention of bone loss, which may result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatments for osteoarthritis, hypocalcemia, hypercalcemia, Paget's disease, osteomalacia, osteohalisteresis, multiple myeloma and other forms of cancer having deleterious effects on bone tissues.

Methods of treating the maladies listed herein are understood to comprise administering to an individual in need of such treatment a pharmaceutically effective amount of one or more of the compounds of this invention or a pharmaceutically acceptable salt thereof. This invention also includes pharmaceutical compositions utilizing one or more of the present compounds, and/or the pharmaceutically acceptable salts thereof, along with one or more pharmaceutically acceptable carriers, excipients, etc.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

Effective administration of these compounds may be given at a dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

Aldrich Sure Seal™ Solvents, anhydrous without further purification, may be used for the reactions described herein and may be obtained from Aldrich Chemical Company. All reactions were carried out under a nitrogen atmosphere. Chromatography was performed using 230–400 mesh silica gel (Merck Grade 60, Aldrich Chemical Company). Thin layer chromatography was performed with Silica Gel 60 $F_{254}$ plates from EM Science. $^1$H NMR spectra were obtained on a Bruker AM-400 or Bruker DPX-300 instrument in DMSO and chemical shifts reported in ppm. Melting points were determined on a Thomas-Hoover apparatus and are uncorrected. IR spectra were recorded on a Perkin-Elmer diffraction grating or Perkin-Elmer 784 spectrophotometers. Mass spectra were recorded on a Kratos MS 50 or Finnigan 8230 mass spectrometers. Elemental analyses were obtained with a Perkin-Elmer 2400 elemental analyzer. Compounds for which CHN are reported are within 0.4% of the theoretical value for the formula given unless expressed otherwise. Compound nomenclature was generally arrived at by use of the Beilstein Autonom™ program.

Synthesis of α-bromo Ketones

Method a

The synthesis of the alpha bromo ketones is conveniantly accomplished by simply dissolving the stating phenyl ketone in ethyl ether (0.05–0.10 M) and at room temperature, 1.1 equivalents of bromine is added in dropwise. The reaction can be monitored by TLC for consumption of starting materials. The reaction is worked up by washing with an aqueous sodium bicarbonate solution followed by a 10% aqueous sodium sulfite solution. The ether layer is washed with brine and dried over magnesium sulfate. Concentration of the reaction mixture typically yields the bromoketones in good yield and purity. The bromoketones were taken "as is" (without purification or characterization) to the next step.

3-Methyl Indoles

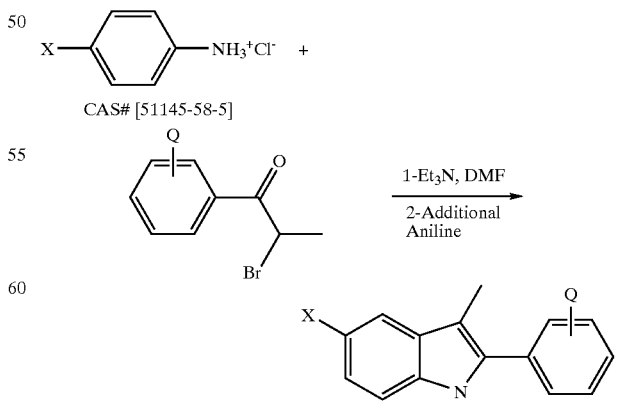

Example Nos. 1–20

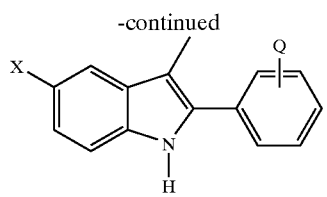

TABLE 1

| Example No. | X | Q |
|---|---|---|
| No. 1 | H | H |
| No. 1a | F | OBn |
| No. 2 | H | 4'-OBn |
| No. 3 | OBn | H |
| No. 4 | OBn | 4'-OMe |
| No. 5 | OMe | 4'-OMe |
| No. 6 | OBn | 4'-OEt |
| No. 7 | OBn | 4'-OBn |
| No. 8 | OBn | 4'-F |
| No. 9 | OBn | 3'-OMe, 4'-OBn |
| No. 10 | OBn | 3', 4'-OCH$_2$O— |
| No. 11 | OBn | 4'-O-iPr |
| No. 12 | OBn | 4'-O-Cp |
| No. 13 | OBn | 4'-CF$_3$ |
| No. 14 | OBn | 4'-CH$_3$ |
| No. 15 | OBn | 4'-Cl |
| No. 16 | OBn | 2'-OMe, 4'-OMe |
| No. 17 | OBn | 3'-OBn |
| No. 18 | OBn | 4'-OBn, 3'-F |
| No. 19 | OBn | 3'-OMe |
| No. 20 | OBn | 4'-OCF$_3$ |

Method 1

Illustrated for Example No. 7

5-Benzyloxy-2-(4-benzyloxy-phenyl)-3-methyl-1H-indole

A flask was charged with 4-benzyloxyaniline hydrochloride CAS No. [51145-58-5]. (45 g, 0.23 mol), 4'-benzyloxy-2-bromophenylpropiophenone CAS No. [66414-19-5] (21 g, 0.066 mol), and 50 mL DMF. The reaction was heated at reflux for 30 minutes and then cooled to rt and then partitioned between 250 mL EtOAc and 100 mL 1N HCl (aq). The EtOAc was washed with NaHCO$_3$ (aq) and brine, then dried over MgSO$_4$. The solution was concentrated and the residue taken up in CH$_2$Cl$_2$ and hexanes added to precipitate out 25 g of a crude solid. The solid was dissolved in CH$_2$Cl$_2$ and evaporated onto silica gel and chromatographed using CH$_2$Cl$_2$/Hexane (1:5) to yield 9.2 g of a tan solid (33%): Mp=150–152° C.; $^1$H NMR (DMSO) 10.88 (s, 1H), 7.56 (d, 2H, J=8.8 Hz), 7.48 (d, 4H, J=7.9 Hz), 7.42–7.29 (m, 6H), 7.21 (d, 1H, J=7.0 Hz), 7.13 (d, 2H, J=8.8 Hz), 7.08 (d, 1H, J=2.2 Hz), 6.94 (dd, 1H, J=8.8, 2.4 Hz), 5.16 (s, 2H), 5.11 (s, 2H), 2.33 (s, 3H); IR (KBr) 3470, 2880, 2820, 1620 cm$^{-1}$; MS eI m/z 419.

Method 2 (Shown in Scheme 8)

Also Illustrated for Example No. 7

Reagents used were same as in method 1 except the additional use of triethylamine in this method. The bromoketone CAS No. [66414-19-5] (50.0 g, 0.16 mol) in 200 mL DMF was treated with the aniline hydrochloride CAS No. [51145-58-5] (44 g, 0.22 mol) and the reaction purged with nitrogen for about 10 minutes. The triethylamine (54.6 mL) was added and the reaction was heated at 120° C. for 2 hours. TLC analysis (EtOAc/hexanes) shows the starting material has dissappeared forming a more polar spot. The reaction mixture is allowed to cool down and an additional 48 g ot the aniline hydrochloride was added. The reaction was heated to 150° C. for 2 hours. An additional 5 grams of the aniline hydrochloride was added and the reaction was heated at 150° C. for an additional 30 minutes. The reaction mixture is allowed to cool to room temperature and then poured into approximately 1.5 liters of water and extracted with 2 liters of ethyl acetate. Solids are dissolved with additional ethyl acetate as neccessary. The ethyl acetate layer is washed with 1 liter of 1 N NaOH solution aq., 1 liter of water, brine, then dried over magnesium sulfate and filtered. The organic layers were concentrated down to yield a crude solid which is stirred with 500 mL of methanol and filtered. This solid is then stirred with 500 mL of ethyl ether and filtered. The solid is stirred alternatively with methanol and ether until it is of whitish color and has a melting point similar to that described for No. 7 in method 1. Reaction yields 36 grams of product.

Physical Data for Indoles

The following 3-methyl indoles (No. 1–No. 20) were synthesized according to the procedure outlined in scheme 2 using method 2 using the appropriately substituted bromoketones (prepared as given above) and anilines (commercially available; Aldrich) as starting materials.

EXAMPLE NO. 1

2-Phenyl-3-methyl-1H-indole

Mp=90–94° C.; $^1$H NMR (DMSO) 11.13 (s, 1H), 7.68–7.64 (m, 2H), 7.54–7.46 (m, 3H), 7.37–7.32 (m, 2H), 7.12–7.06 (m, 1H), 7.03–6.97 (m, 1H), 2.40 (s, 3H); MS eI m/z 207 (M+).

EXAMPLE NO. 1a

5-Flouro-2-(4-benzyloxy-phenyl)-3-methyl-1H-indole

Mp=143–146° C.

EXAMPLE NO. 2

2-(4-Benzyloxy-phenyl)-3-methyl-1H-indole

Mp=118–120° C.; $^1$H NMR (DMSO) 11.03 (s, 1H), 7.57 (dd, 2H, J=2.0 Hz, 6.6 Hz), 7.48–7.46 (m, 3H), 7.44–7.28 (m, 4H), 7.18–7.11 (m, 2H), 7.08–7.03 (m, 1H), 7.0–6.95 (m, 1H), 5.16 (s, 2H), 2.36 (s, 3H); MS eI m/z 313 (M+).

EXAMPLE NO. 3

5-Benzyloxy-2-phenyl-3-methyl-1H-indole

Mp=141–144° C.; $^1$H NMR (DMSO) 10.98 (s, 1H), 7.65–7.61 (m, 2H), 7.51–7.44 (m, 4H), 7.42–7.28 (m, 4H), 7.23 (d, 1H, J=8.8 Hz), 7.10 (d, 1H, J=2.5 Hz), 6.80 (d, 1H, J=6.0 Hz), 5.10 (s, 2H), 2.36 (s, 3H); MS eI m/z 313 (M+).

EXAMPLE NO. 4

5-Benzyloxy-2-(4-methoxy-phenyl)-3-methyl-1H-indole

Mp=158° C.; $^1$H NMR 10.85 (brs, 1H), 7.56 (d, 2H, J=8.8 Hz), 7.48 (d, 2H, J=8.3 Hz), 7.45–7.36 (m, 2H), 7.34–7.28

(m, 1H), 7.21 (d, 1H, J=8.6 Hz), 7.09–7.04 (m, 3H), 6.79 (dd, 1H, J=8.8 Hz), 5.11 (s, 2H), 3.80 (s, 3H), 2.33 (s, 3H); IR (KBr) 3400, 2900, 1610 cm$^{-1}$; MS eI m/z 343 (M+); CHN calcd for $C_{23}H_{21}NO_2+0.25H_2O$.

EXAMPLE NO. 5

5-methoxy-2-(4-methoxy-phenyl)-3-methyl-1H-indole

Mp=139–142° C.; $^1$H NMR (DMSO) 10.85 (s, 1H), 7.57 (d, 2H, J=8.8 Hz), 7.19 (d, 1H, J=8.6 Hz), 7.04 (d, 2H, J=6.8 Hz), 6.95 (d, 1H, J=2.2 Hz), 6.71 (dd, 1H, J=8.5 Hz, J=2.4 Hz), 3.80 (s, 3H), 3.76 (s, 3H), 2.33 (s, 3H); MS eI m/z 267 (M+); CHN calc for $C_{17}H_{17}NO_2$.

EXAMPLE NO. 6

5-Benzyloxy-2-(4-ethoxy-phenyl)-3-methyl-1H-indole

Mp=143–145° C.; $^1$H NMR (DMSO) 10.86 (s, 1H), 7.54 (d, 2H, J=8.5 Hz), 7.46 (d, 2H, J=7.3 Hz), 7.41–7.37 (m, 2H), 7.32–7.30 (m, 1H), 7.20 (d, 1H, J=8.6 Hz), 7.05 (d, 1H), 7.03 (d, 2H, J=8.8 Hz), 6.79 (dd, 1H, J=8.6 Hz, J=2.4 Hz), 5.10 (s, 2H), 4.07 (q, 2H, J=6.8 Hz), 2.32 (s, 3H), 1.34 (t, 3H, J=7.0 Hz); MS eI m/z 357 (M+).

EXAMPLE NO. 8

5-Benzyloxy-2-(4-fluoro-phenyl)-3-methyl)-1H-indole

Mp=132° C.; $^1$H NMR (DMSO) 11.0 (s, 1H), 7.68–7.64 (m, 2H), 7.49–7.47 (m, 2H), 7.41–7.31 (m, 5H), 7.23 (d, 1H, J=8.8 Hz), 7.10 (d, 1H, J=2.4 Hz), 6.82 (dd, 1H, J=8.8, 2.4 Hz), 5.11 (s, 2H), 2.34 (s, 3H); MS EI m/z 331; CHN calcd for $C_{22}H_{18}FNO$.

EXAMPLE NO. 9

5-Benzyloxy-2-(4-benzyloxy-3-methoxy-phenyl)-3-methyl-1H-indole

Mp=155–158° C.; $^1$H NMR (DMSO) 10.88 (s, 1H), 7.50–7.45 (m, 4H), 7.41–7.35 (m, 6H), 7.22–7.20 (m, 2H), 7.14 (s, 2H), 7.08 (d, 1H, J=2.2 Hz), 6.78 (dd, 1H, J=8.5 Hz, J=2.4 Hz), 5.13 (s, 2H), 5.11 (s, 2H), 3.85 (s, 3H), 2.35 (s, 3H); MS eI m/z 449 (M+).

EXAMPLE NO. 10

2-Benzo[1,3]dioxol-5-yl-5-benzyloxy-3-methyl-1H-indole

Mp=142–145° C.; $^1$H NMR (DMSO) 10.86 (s, 1H), 7.48 (d, 2H, J=7.0 Hz), 7.40–7.30 (m, 3H), 7.20 (m, 2H), 7.10–7.05 (m, 3H), 6.78 (dd, 1H, J=8.8 Hz, J=2.4 Hz), 6.06 (s, 2H), 5.10 (s, 2H), 2.31 (s, 3H); MS eI m/z 357 (M+); CHN calc for $C_{23}H_{19}NO_3$.

EXAMPLE NO. 11

5-Benzyloxy-2-(4-isopropoxy-phenyl)-3-methyl)-1H-indole

Mp=136–138° C.; $^1$H NMR (DMSO) 10.86 (s, 1H), 7.55–7.51 (m, 2H), 7.50–7.47 (d, 2H, J=7.3 Hz), 7.40–7.34 (m, 2H), 7.39–7.28 (m, 1H), 7.20 (d, 1H, J=8.7 Hz), 7.06 (d, 1H, J=2.2 Hz), 7.02 (d, 2H, J=8.8 Hz), 6.77 (dd, 1H, J=2.4 Hz, 8.8 Hz), 5.10 (s, 2H), 4.68–4.62 (m, 1H), 2.32 (s, 3H), 1.28 (d, 6H, J=6.0 Hz); MS eI m/z 371 (M+).

EXAMPLE NO. 12

5-Benzyloxy-2-(4-cyclopenyloxy-phenyl)-3-methyl-1H-indole

Mp=161–167° C.; $^1$H NMR (DMSO) 10.85 (s, 1H), 7.53 (d, 2H, J=8.8 Hz), 7.47 (d, 2H, J=8.4 Hz), 7.40–7.36 (m, 2H), 7.33–7.28 (m, 1H), 7.20 (d, 1H, J=8.6 Hz), 7.07 (d, 1H, J=2.4 Hz), 7.01 (d, 2H, J=8.8 Hz), 6.78 (dd, 1H, J=8.6 Hz, 2.2 Hz), 5.10 (s, 2H), 4.88–4.84 (m, 1H), 2.32 (s, 3H), 1.99–1.88 (m, 2H), 1.78–1.69 (m, 4H), 1.64–1.52 (m, 2H); IR (KBr) 3400, 2920, 1600 cm$^{-1}$; MS eI m/z 397 (M+); CHN calcd for $C_{27}H_{27}NO_2+0.25H_2O$.

EXAMPLE NO. 13

5-Benzyloxy-2-(4-triflouromethyl-phenyl)-3-methyl-1H-indole $^1$H NMR (DMSO) 11.0 (br s, 1H), 7.87–7.82 (m, 4H), 7.48 (d, 2H, J=8.8 Hz), 7.44–7.35 (m, 2H), 7.34–7.26 (m, 2H), 7.15 (d, 1H, J=2.2 Hz), 6.87 (dd, 1H, J=8.6 Hz, 2.4 Hz), 5.12 (s, 2H), 2.41 (s, 3H); CHN calcd for $C_{23}H_{18}F_3NO$.

EXAMPLE NO. 14

5-Benzyloxy-2-(4-methyl-phenyl)-3-methyl-1H-indole

Mp=144–146° C.; $^1$H NMR (DMSO) 10.91 (s, 1H), 7.56–7.20 (m, 10H), 7.08 (d, 1H, J=2.4 Hz), 6.80 (dd, 1H, J=2.4 Hz, 8.6 Hz), 5.11 (s, 2H), 2.34 (s, 3H), 2.34 (s, 3H); MS eI m/z 327 (M+).

EXAMPLE NO. 15

5-Benzyloxy-2-(4-chloro-phenyl)-3-methyl-1H-indole

Mp=134–136° C.; $^1$H NMR (DMSO) 11.04 (s, 1H), 7.65 (d, 2H, J=8.3 Hz), 7.53 (d, 2H, J=8.5 Hz), 7.47 (d, 2H, J=6.8 Hz), 7.41–7.37 (m, 2H), 7.31–7.28 (m, 1H), 7.25 (d, 1H, J=8.5 Hz), 7.11 (d, 1H, J=2.4 Hz), 6.82 (dd, 1H, J=8.8 Hz, J=2.4 Hz), 5.11 (s, 2H), 2.35 (s, 3H); IR (KBr) 3380, 1210 cm$^{-1}$, Ms eI m/z 347 (M+); CHN calc for $C_{22}H_{18}ClNO_2$.

EXAMPLE NO. 16

5-Benzyloxy-2-(2,4-dimethoxy-phenyl)-3-methyl-1H-indole

Oil; $^1$H NMR (DMSO) 10.58 (s, 1H), 7.50–7.18 (m, 7H), 7.04 (d, 1H, J=2.4 Hz), 6.76 (dd, 1H, J=2.3 Hz, 8.6 Hz), 6.69–6.62 (m, 2H), 5.11 (s, 2H), 3.82 (s, 3H), 3.78 (s, 3H), 2.12 (s, 3H).

EXAMPLE NO. 17

5-Benzyloxy-2-(3-benzyloxy-phenyl)-3-methyl-1H-indole

Mp=83–86° C.

EXAMPLE NO. 18

5-Benzyloxy-2-(4-benzyloxy-3-fluoro-phenyl)-3-methyl-1H-indole

Mp=135–137° C.; $^1$H NMR (DMSO) 10.94 (s, 1H), 7.50–7.31 (m, 13H), 7.22 (d, 1H, J=8.6 Hz), 7.10 (d, 1H,

J=2.2 Hz), 6.81 (dd, 1H, J=8.6 Hz, 2.2 Hz), 5.23 (s, 2H), 5.11 (s, 2H), 2.34 (s, 3H); MS eI m/z 437 (M+); CHN calcd for $C_{29}H_{24}FNO_2$.

EXAMPLE NO. 19

5-Benzyloxy-2-(3-methoxy-phenyl)-3-methyl-1H-indole

Mp=107–109° C.; $^1$H NMR (DMSO) 11.00 (s, 1H), 7.51–7.48 (m, 2H), 7.43–7.20 (m, 7H), 7.13–7.12 (d, 1H, J=2.1 Hz), 6.93–6.90 (dd, 1H, J=2.3 Hz, J=5.7 Hz), 6.86–6.82 (dd, 1H, J=2.3 Hz, J=6.3 Hz), 5.12 (s, 2H), 3.83 (s, 3H), 2.38 (s, 3H); IR (KBr) 3400, 2900, 1600 cm$^{-1}$; MS eI m/z 343 (M+); CHN calcd for $C_{23}H_{21}NO_2$.

EXAMPLE NO. 20

5-Benzyloxy-3-methyl-2-(4-trifluoromethoxy-phenyl)-1H-indole

Mp=127–128° C.; $^1$H NMR (DMSO) 11.07 (s, 1H), 7.77–7.74 (dd, 2H, J=1.8 Hz, J=5.0 Hz), 7.50–7.48 (d, 4H, J=8.3 Hz), 7.42–7.25 (m, 4H), 7.14–7.13 (d, 1H, J=2.2 Hz), 6.87–6.83 (dd, 1H, J=2.3 Hz, J=6.3 Hz), 5.13 (s, 2H), 2.37 (s, 3H); IR (KBr) 3360, 1600 cm$^{-1}$; MS eI m/z 396 (M+); CHN calcd for $C_{23}H_{18}F_3NO_2$.

3-Methylindole Acetic Acid Ethyl Esters

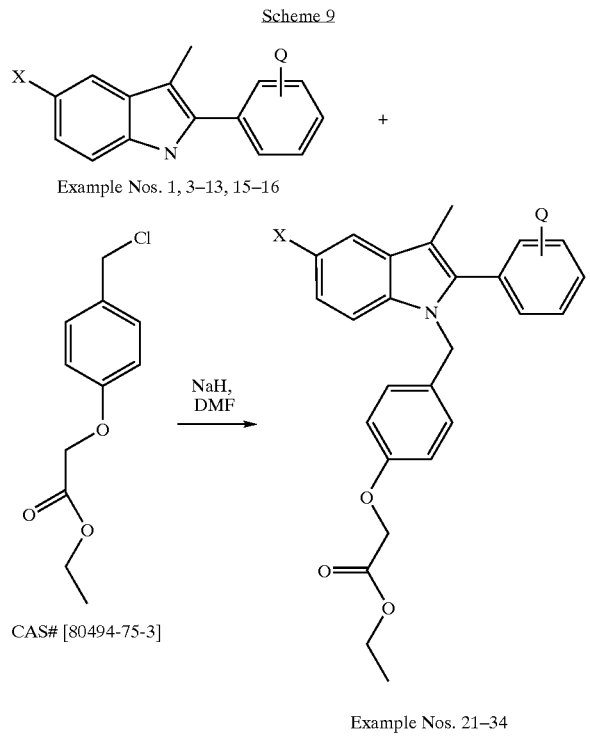

Scheme 9

Example Nos. 1, 3–13, 15–16

CAS# [80494-75-3]

Example Nos. 21–34

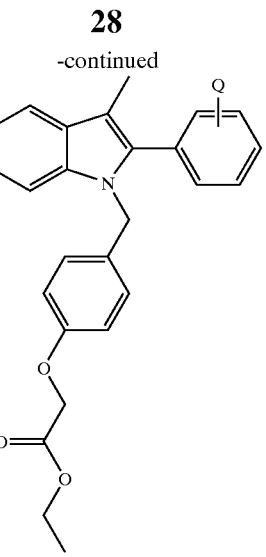

-continued

TABLE 2

| Example No. | X | Q |
|---|---|---|
| No. 21 | H | H |
| No. 22 | OBn | H |
| No. 23 | OBn | 4'-OMe |
| No. 24 | OMe | 4'-OMe |
| No. 25 | OBn | 4'-OEt |
| No. 26 | OBn | 4'-OBn |
| No. 27 | OBn | 4'-F |
| No. 28 | OBn | 3'-OMe, 4'-OBn |
| No. 29 | OBn | 4'-O-iPr |
| No. 30 | OBn | 3', 4'-OCH$_2$O— |
| No. 31 | OBn | 4'-OCp |
| No. 32 | OBn | 4'-CF$_3$ |
| No. 33 | OBn | 4'-Cl |
| No. 34 | OBn | 2'-OMe, 4'-OMe |

Experimental Procedure for 3-Methylindole Acetic Acid Ethyl Esters

Synthesis Method 3

Illustrated for Example No. 26

{4-[5-Benzyloxy-2-(4-benzyloxy-phenyl)-3-methyl-indol-1-ylmethyl]-phenoxy}-acetic acid ethyl ester A solution of 5-Benzyloxy-2-(4-benzyloxy-phenyl)-3-methyl-1H-indole (indole example No. 7) (32 g, 77 mmol) in DMF (0.15 L) was cooled to 0° C. and treated with sodium hydride (2.2 g, 89 mmol). The reaction was stirred for 20 minutes and then the benzyl chloride CAS No. [80494-75-3] (29 g, 127 mmol) was added and the reaction stirred for 18 hours at room temperature. The reaction mixture was poured into water and extracted with ethyl acetate. The ethyl acetate was washed with brine and dried over magnesium sulfate. The ethyl acetate was concentrated and triturated with ether to obtain 21 g of a white solid. The filtrate was concentrated and triturated with ether to give an additional 7 g of white solid for a total yield of 28 g: Mp=129–131° C.; $^1$H NMR (DMSO) 7.47 (d, 4H, J=7.2 Hz), 7.39 (q, 4H, J=7.9 Hz), 7.36–7.32 (m, 1H), 7.29 (d, 2H, J=8.8 Hz), 7.19 (d, 1H, J=9.0 Hz), 7.13–7.09 (m, 4H), 6.80 (dd, 1H, J=8.8, 2.4 Hz), 6.73 (s, 4H), 5.16 (s, 2H), 5.13 (s, 2H), 5.11 (s, 2H), 4.66 (s, 2H), 4.11 (q, 2H, J=7.2 Hz), 2.15 (s, 3H), 1.16 (t, 3H, J=7.2 Hz); MS eI m/z 612.

Physical Data for Indole Ethyl Esters

The following indole alkylation products were prepared according to scheme 9 using method 3 with the appropriately substituted 3-methyl indole selected from (No. 1–No. 16) as the starting material.

EXAMPLE NO. 21

{4-[2-Phenyl-3-methyl-indol-1-ylmethyl]-phenoxy}-acetic acid ethyl ester

Oil; $^1$H NMR (DMSO) 7.57–7.30 (m, 7H), 7.13–7.02 (m, 2H), 6.77–6.70 (n, 4H), 5.22 (s, 2H), 4.65 (s, 2H), 4.09 (q, 2H, J=7.2 Hz), 2.20 (s, 3H), 1.15 (t, 3H, J=7.0 Hz); MS eI m/z 399 (M+).

EXAMPLE NO. 22

{4-[5-Benzyloxy-2-phenyl-3-methyl-indol-1-ylmethyl]-phenoxy}-acetic acid ethyl ester Oil; $^1$H NMR (DMSO) 750–7.40 (m, 10H), 7.22 (d, 1H, J=8.4 Hz), 7.14 (d, 1H, J=2.5 Hz), 6.83 (d, 1H, J=2.5 Hz), 6.72 (s, 4H), 5.18 (s, 2H), 5.11 (s, 2H), 4.65 (s, 2H), 4.10 (q, 2H, J=7.2 Hz), 2.16 (s, 3H), 1.14 (t, 3H, J=7.0 Hz); MS eI m/z 505 (M+).

EXAMPLE NO. 23

{4-[5-Benzyloxy-2-(4-methoxy-phenyl)-3-methyl-indol-1-ylmethyl]-phenoxy}-acetic acid ethyl ester Mp=90–96° C.; $^1$H NMR (DMSO) 7.47 (d, 2H, J=6.8 Hz), 7.41–7.37 (m, 2H), 7.33–7.27 (m, 3H), 7.19 (d, 1H, J=8.8 Hz), 7.12 (d, 1H, J=2.4 Hz), 7.03 (d, 2H, J=8.8 Hz), 6.80 (dd, 1H, J=8.8 Hz, 2.4 Hz), 6.74 (s, 4H), 5.16 (s, 2H), 5.11 (s, 2H), 4.65 (s, 2H), 4.11 (q, 2H, J=7.0 Hz), 3.79 (s, 3H), 2.15 (s, 3H), 1.16 (t, 3H, J=7.0 Hz); IR (KBr) 2990, 2900, 1760, 1610 cm-1; MS FAB m/z 536 (M+H+).

EXAMPLE NO. 24

{4-[5-Methoxy-2-(4-methoxy-phenyl)-3-methyl-indol-1-ylmethyl]-phenoxy}-acetic acid ethyl ester Mp=109–113° C.; $^1$H NMR (DMSO) 7.27 (d, 2H, J=8.8 Hz), 7.17 (d, 1H, J=8.8 Hz), 7.03 (d, 2H, J=8.6 Hz), 6.99 (d, 1H, J=2.5 Hz), 6.78–6.70 (m, 5H), 5.15 (s, 2H), 4.65 (s, 2H), 4.11 (q, 2H, J=7.0 Hz), 3.78 (s, 3H), 3.76 (s, 3H), 2.15 (s, 3H), 1.15 (t, 3H, J=7.1 Hz); MS eI m/z 459 (M+).

EXAMPLE NO. 25

{4-[5-Benzyloxy-2-(4-ethoxy-phenyl)-3-methyl-indol-1-ylmethyl]-phenoxy}-acetic acid ethyl ester Mp=113–115° C.; $^1$H NMR (DMSO) 7.45 (d, 2H, J=7.3 Hz), 7.40–7.25 (m, 5H), 7.17 (d, 1H, J=8.8 Hz), 7.11 (d, 1H, J=2.2 Hz), 7.01 (d, 2H, J=6.8 Hz), 6.78 (dd, 1H, J=8.8 Hz, J=2.4 Hz), 6.73 (s, 4H), 5.15 (s, 2H), 5.10 (s, 2H), 4.65 (s, 2H), 4.15–4.01 (m, 4H), 2.14 (s, 3H), 1.33 (t, 3H, J=5.7 Hz), 1.16 (t, 3H, J=7.1 Hz); MS eI m/z 549 (M+).

EXAMPLE NO. 27

{4-[5-Benzyloxy-2-(4-flouro-phenyl)-3-methyl-indol-1-ylmethyl]-phenoxy}-acetic acid ethyl ester $^1$H NMR (DMSO) 7.50–7.15 (m, 16H), 5.20 (s, 2H), 5.12 (s, 2H), 4.62 (s, 2H), 4.13 (q, 2H, J=7.1 Hz), 2.18 (s, 3H), 1.20 (t, 3H, J=7.1 Hz).

EXAMPLE NO. 28

{4-[5-Benzyloxy-2-(3-methoxy-4-benzyloxy)-3-methyl-indol-1-ylmethyl]-phenoxy}-acetic acid ethyl ester Foam; $^1$H NMR (DMSO) 7.50–7.30 (m, 10H), 7.22 (d, 2H, J=9.1 Hz), 7.13 (d, 2H, J=8.6 Hz), 6.85–6.70 (m, 6H), 5.17 (s, 2H), 5.13 (s, 2H), 5.11 (s, 2H), 4.66 (s, 2H), 4.14 (m, 2H), 3.61 (s, 3H), 2.17 (s, 3H), 1.16 (t, 3H, J=7.0 Hz).

EXAMPLE NO. 29

{4-[5-Benzyloxy-2-(4-isopropoxy-phenyl)-3-methyl-indol-1-ylmethyl]-phenoxy}-acetic acid ethyl ester Oil; $^1$H NMR (DMSO) 7.46 (d, 2H, J=7.7 Hz), 7.42–7.28 (m, 3H), 7.25 (d, 2H, J=8.7 Hz), 7.17 (d, 1H, J=8.7 Hz), 7.11 (d, 1H, J=2.4 Hz), 6.99 (d, 2H, J=8.6 Hz), 6.79 (dd, 1H, J=2.4 Hz, 8.8 Hz), 6.73 (s, 4H), 5.15 (s, 2H), 5.10 (s, 2H), 4.70–4.60 (m, 3H), 4.10 (q, 2H, J=7.0 Hz), 2.15 (s, 3H), 1.27 (d, 6H, J=5.9 Hz), 1.16 (t, 3H, J=7.1 Hz); MS eI m/z 563 (M+).

EXAMPLE NO. 30

{4-[5-Benzyloxy-2-(3,4-methlyenedioxy-benzyloxy)-3-methyl-indol-1-ylmethyl]-phenoxy}-acetic acid ethyl ester Oil; $^1$H NMR (DMSO) 7.45 (d, 2H, J=7.0 Hz), 7.37 (m, 2H), 7.32 (m, 1H), 7.19 (d, 1H, J=8.8 Hz), 7.11 (d, 1H, J=2.2 Hz), 7.00 (d, 1H, J=7.9 Hz), 6.90 (d, 1H, 5.0 Hz), 6.82–6.75 (m, 6H), 6.07 (s, 2H), 5.16 (s, 2H), 5.10 (s, 2H), 4.65 (s, 2H), 4.10 (m, 2H), 2.15 (s, 3H), 1.15 (t, 3H, J=7.0 Hz); MS eI m/z 549 (M+).

EXAMPLE NO. 31

{4-[5-Benzyloxy-2-(4-cyclopentyloxy-phenyl)-3-methyl-indol-1-ylmethyl]-phenoxy}-acetic acid ethyl ester Mp=96–98° C.; $^1$H NMR (DMSO) 7.47 (d, 1H, J=7.2 Hz), 7.40–7.36 (m, 2H), 7.33–7.30 (m, 1H), 7.26 (m, 2H), 7.18 (d, 1H, J=8.8 Hz), 7.11 (d, 1H, J=2.4 Hz), 6.98 (d, 2H, J=8.8 Hz), 6.79 (dd, 1H, J=8.8 Hz, 2.4 Hz), 6.74 (s, 5H), 5.15 (s, 2H), 5.11 (s, 2H), 4.86–4.80 (m, 1H), 4.66 (s, 2H), 4.13 (q, 2H, J=7.2 Hz), 2.15 (s, 3H), 1.98–1.85 (m, 2H), 1.79–1.65 (m, 4H), 1.62–1.55 (m, 2H), 1.16 (t, 3H, J=7.0 Hz); IR (KBr) 2950, 2910, 2890, 1760, 1610 cm$^{-1}$; MS EI m/z 589 (M+); CHN calcd for C: 77.39 H: 6.67 N: 2.38 Found: C: 76.76 H: 6.63 N: 2.27.

EXAMPLE NO. 32

{4-[5-Benzyloxy-3-methyl-2-(4-trifluoromethyl-phenyl)-indol-1-ylmethyl]-phenoxy}-acetic acid ethyl ester Mp=221° C.; $^1$H NMR (DMSO) 7.83 (d, 2H, J=8.1 Hz), 7.60 (d, 2H, J=7.9 Hz), 7.48 (d, 2H, J=8.4 Hz), 7.40–7.36 (m, 4H), 7.18 (d, 1H, J=2.4 Hz), 6.86 (dd, 1H, J=8.8 Hz, 2.4 Hz), 6.72 (s, 4H), 5.21 (s, 2H), 5.12 (s, 2H), 4.65 (s, 2H), 4.11 (q, 2H, J=72 Hz), 2.20 (s, 3H), 1.16 (t, 3H, J=7.0 Hz); IR (KBr) 2920, 1730 cm$^{-1}$; MS eI m/z 573 (M+); CHN calcd for $C_{34}H_{30}F_3NO_4+0.25H_2O$.

EXAMPLE NO. 33

{4-[5-Benzyloxy-2-(4-chlorophenyl)-3-methyl-indol-1-ylmethyl]-phenoxy}-acetic acid ethyl ester Mp=99–101° C.; $^1$H NMR (DMSO) 7.52 (d, 2H, J=8.6 Hz), 7.46 (d, 2H, J=6.8 Hz), 7.42–7.38 (m, 4H), 7.36 (m, 1H), 7.25 (d, 1H, J=9.0 Hz), 7.14 (d, 1H, J=2.4 Hz), 6.83 (dd, 1H, J=8.8 Hz, J=2.5 Hz), 6.72 (s, 4H), 5.18 (s, 2H), 5.11 (s, 2H), 4.65 (s, 2H), 4.11 (q, 2H, J=7.2 Hz), 2.16 (s, 3H), 1.15 (t, 3H, J=7.2 Hz); MS eI m/z 539 (M+); CHN calc for $C_{33}H_{30}ClNO_4$.

EXAMPLE NO. 34

{4-[5-Benzyloxy-2-(2,4-dimethoxy)-3-methyl-indol-1-ylmethyl]-phenoxy}-acetic acid ethyl ester Oil; $^1$H NMR (DMSO) 7.30–6.45 (m, 15H), 4.95 (s, 2H), 4.75–4.65 (m, 2H), 4.50 (s, 2H), 3.97 (q, 2H, J=7.1 Hz), 3.65 (s, 3H), 3.51 (s, 3H), 1.87 (3H), 1.01 (t, 3H, J=7.1 Hz).

3-Methylindole phenylethanols

Scheme 10

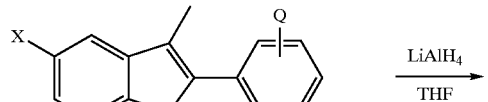

LiAlH$_4$

THF

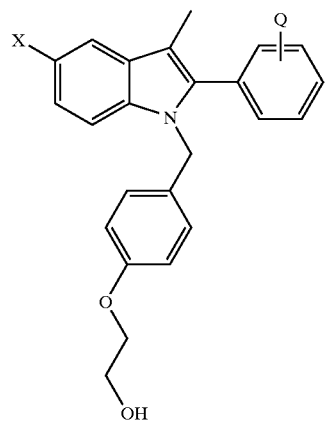

Example Nos. 21, 24–27, 29–34

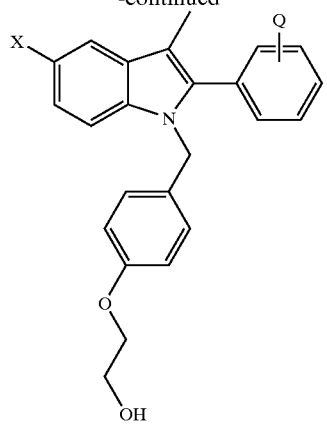

TABLE 3

| Example No. | X | Q |
|---|---|---|
| No. 35 | H | H |
| No. 36 | OMe | 4'-OMe |
| No. 37 | OBn | 4'-OEt |
| No. 38 | OBn | 4'-OBn |
| No. 39 | OBn | 4'-F |
| No. 40 | OBn | 3', 4'-OCH$_2$O— |
| No. 41 | OBn | 4'-O-iPr |
| No. 42 | OBn | 4'-OCp |
| No. 43 | OBn | 4'-CF$_3$ |
| No. 44 | OBn | 4'-CH$_3$ |
| No. 45 | OBn | 4'-Cl |
| No. 46 | OBn | 2'-OMe, 4'-OMe |

Experimental Procedure for 3-Methylindole Phenethanols Synthesis

Method 4

Illustrated for Example No. 38

2-{4-[5-Benzyloxy-2-(4-benzyloxy-phenyl)-3-methyl-indol-1-ylmethyl]-phenoxy}-ethanol A solution of No. 26 from previous step (5.5 g, 8.8 mmol) in THF (50 mL) was cooled to 0° C. and a solution of LiAlH$_4$ (10 mL, 1 M) in THF was added dropwise. After 30 minutes at 0° C. the reaction was carefully quenched with water, and partitioned between EtOAc and 1 N HCl. The EtOAc was dried with MgSO$_4$, concentrated, and chromatogrphed on silica gel EtOAc/hexane (2:3) to yield 4.0 g of No. 38 as a white foam: $^1$H NMR (DMSO) 7.48–7.46 (m, 4H), 7.42–7.27 (m, 8H), 7.20 (d, 1H, J=8.8 Hz), 7.12–7.10 (m, 3H), 6.80 (dd, 1H, J=8.8, 2.4 Hz), 6.73 (s, 4H), 5.15 (s, 2H), 5.13 (s, 2H), 5.11 (s, 2H), 4.80 (t, 1H, J=5.5 Hz), 3.86 (t, 2H, J=4.8 Hz), 3.63 (q, 2H, J=5.3 Hz), 2.15 (s, 3H).

Physical Data for Indole Phenethanols

Following compounds were made according to scheme 10 and method 4 using the appropriately substituted indole ethyl ester selected from No. 21–No. 34

EXAMPLE NO. 35

2-{4-[2-phenyl-3-methyl-indol-1-ylmethyl]-phenoxy}-ethanol

Oil; $^1$H NMR (DMSO) 7.57–7.32 (m, 7H), 7.13–7.02 (m, 2H), 6.74 (s, 4H), 5.21 (s, 2H), 4.80 (s, 1H), 3.86–3.83 (m, 2H), 3.62 (s, 2H), 2.20 (s, 3H); MS eI m/z 357 (M+).

EXAMPLE NO. 36

2-{4-[5-methoxy-2-(4-methoxy-phenyl)-3-methyl-indol-1-ylmethyl]-phenoxy}-ethanol Oil; $^1$H NMR (DMSO) 7.27 (d, 2H, J=8.8 Hz), 7.17 (d, 1H, J=8.8 Hz), 7.03 (d, 2H J=8.6 Hz), 6.99 (d, 1H, J=2.5 Hz), 6.78–6.70 (m, 5H), 5.14 (s, 2H), 4.80 (brs, 1H), 3.85 (t, 2H, J=5.0 Hz), 3.78 (s, 3H), 3.76 (s, 3H), 3.63 (t, 2H, J=5.0 Hz), 2.16 (s, 3H); MS eI m/z 417 (M+).

EXAMPLE NO. 37

2-{4-[5-benzyloxy-2-(4-ethoxy-phenyl)-3-methyl-indol-1-ylmethyl]-phenoxy}-ethanol Foam; $^1$H NMR (DMSO) 7.45 (d, 2H, J=7.3 Hz), 7.40–7.25 (m, 5H), 7.17 (d, 1H, J=8.8 Hz), 7.11 (d, 1H, J=2.2 Hz), 7.01 (d, 2H, J=6.8 Hz), 6.78 (dd, 1H, J=8.8 Hz, J=2.4 Hz), 6.73 (s, 4H), 5.15 (s, 2H), 5.10 (s, 2H), 4.80 (brs, 1H), 4.06 (q, 2H, J=6.8 Hz), 3.85 (t, 2H, J=5.0 Hz), 3.63 (t, 2H, J=4.8 Hz), 2.14 (s, 3H), 1.33 (t, 3H, J=6.9 Hz); MS eI m/z 507 (M+).

EXAMPLE NO. 39

2-{4-[5-benzyloxy-2-(4-flouro-phenyl)-3-methyl-indol-1-ylmethyl]-phenoxy}-ethanol $^1$H NMR (DMSO) 7.40–6.60 (m, 16H), 5.10 (s, 1H), 5.07 (s, 2H), 5.02 (s, 2H), 3.76(t, 2H, J=4.9 Hz), 3.53(t, 2H, J=5.0 Hz), 2.06 (s, 3H).

EXAMPLE NO. 40

2-{4-[5-benzyloxy-2-(3.4-methylenedioxy-phenyl)-3-methtyl-indol-1-ylmethyl]-phenoxy}-ethanol Oil; $^1$H NMR (DMSO) 7.45 (d, 2H, J=7.0 Hz), 7.37 (m, 2H), 7.32 (m, 1H), 7.19 (d, 1H, J=8.8 Hz), 7.11 (d, 1H, J=2.2 Hz), 7.00 (d, 1H, J=7.9 Hz), 6.90 (d, 1H, 5.0 Hz), 6.82–6.75 (m, 6H), 6.07 (s, 2H), 5.16 (s, 2H), 5.10 (s, 2H), 3.86 (t, 2H, J=5.0 Hz), 3.63 (t, 2H, J=5.0 Hz), 2.15 (s, 3H); MS eI m/z 507 (M+).

EXAMPLE NO. 41

2-{4-[5-Benzyloxy-2-(4-isopropoxy-phenyl)-3-methyl-indol-1-ylmethyl]-phenoxy}-ethanol Foam; $^1$H NMR (DMSO) 7.46 (d, 2H, J=7.7 Hz), 7.42–7.28 (m, 3H), 7.25 (d, 2H, J=8.7 Hz), 7.17 (d, 1H, J=8.7 Hz), 7.11 (d, 1H, J=2.4 Hz), 6.99 (d, 2H, J=8.6 Hz), 6.79 (dd, 1H, J=2.4 Hz, 8.8 Hz), 6.73 (s, 4H), 5.14 (s, 2H), 5.10 (s, 2H), 4.80 (bs, 1H), 4.70–4.60 (m, 1H), 3.85 (t, 2H, J=4.8 Hz), 3.63 (t, 2H, J=5.1 Hz), 2.13 (s, 3H), 1.30 (d, 6H, J=5.9 Hz); MS eI m/z 521 (+).

EXAMPLE NO. 42

2-{4-[5-Benzyloxy-2-(4-cyclopentyloxy-phenyl)-3-methyl-indol-1-ylmethyl]-phenoxy}-ethanol Mp=129–131° C.; $^1$H NMR (DMSO) 7.47 (d, 2H, J=7.2 Hz), 7.38 (t, 2H, J=7.2 Hz), 7.33–7.28 (m, 1H), 7.25 (d, 2H, J=8.8 Hz), 7.18 (d, 1H, J=8.8 Hz), 7.11 (d, 1H, J=2.4 Hz), 6.98 (d, 2H, J=8.8 Hz), 6.79 (dd, 1H, J=8.8 Hz, 2.4 Hz), 6.74 (s, 4H), 5.15 (s, 2H), 5.11 (s, 2H), 4.84–4.80 (m, 1H), 4.79 (t, 1H, J=5.7 Hz), 3.86 (t, 2H, J=4.8 Hz), 3.63 (q, 2H, J=5.1 Hz), 2.15 (s, 3H), 1.96–1.87 (m, 2H), 1.77–1.65 (m, 4H), 1.62–1.53 (m, 2H); IR (KBr) 3490 br, 2920, 1620 cm−1; MS eI m/z 547 (M+).

EXAMPLE NO. 43

2-{4-[5-Benzyloxy-2-(4-triflouromethyl-phenyl)-3-methyl-indol-1-ylmethyl]-phenoxy}-ethanol Foam; $^1$H NMR (DMSO) 7.83 (d, 2H, J=8.1 Hz), 7.59 (d, 2H, J=7.9 Hz), 7.47 (d, 2H, J=8.8 Hz), 7.42–7.36 (m, 2H), 7.35–7.29 (m, 2H), 7.18 (d, 1H, J=2.4 Hz), 6.87 (dd, 1H, J=8.1 Hz, 2.4 Hz), 6.77–6.68 (m, 4H), 5.21 (s, 2H), 5.12 (s, 2H), 4.81 (br s, 1H), 3.85 (t, 2H, J=5.1 Hz), 3.63 (t, 2H, J=5.1 Hz), 2.19 (s, 3H); MS eI m/z 531.

EXAMPLE NO. 44

2-{4-[5-Benzyloxy-2-(4-methyl-phenyl)-3-methyl-indol-1-ylmethyl]-phenoxy}-ethanol Oil; $^1$H NMR (DMSO) 7.46 (d, 2H, J=7.2 Hz), 7.45–7.18 (m, 8H), 7.12 (d, 1H, J=2.4 Hz), 6.81 (dd, 1H, J=2.4 Hz, 8.6 Hz), 6.73 (s, 4H), 5.15 (s, 2H), 5.10 (s, 2H), 4.80 (bs, 1H), 3.85 (t, 2H, J=4.8 Hz), 3.63 (t, 2H, J=4.9 Hz), 2.34 (s, 3H), 2.15 (s, 3H); MS eI m/z 477 (M+).

EXAMPLE NO. 45

2-{4-[5-Benzyloxy-2-(4-choro-phenyl)-3-methyl-indol-1-ylmethyl]-phenoxy}-ethanol Mp=110–113° C.; $^1$H NMR (DMSO) 7.52 (d, 2H, J=8.6 Hz), 7.46 (d, 2H, J=6.8 Hz), 7.38 (m, 4H), 7.42–7.37 (m, 1H), 7.25 (d, 1H, J=9.0 Hz), 7.14 (d, 1H, J=2.4 Hz), 6.83 (dd, 1H, J=8.8 Hz, J=2.5 Hz), 6.76–6.70 (m, 4H), 5.17 (s, 2H), 5.11 (s, 2H), 3.85 (t, 2H, J=5.2 Hz), 3.63 (t, 2H, J=5.0 Hz), 2.16 (s, 3H); MS eI m/z 497 (M+).

EXAMPLE NO. 46

2-{4-[5-Benzyloxy-2-(2,4-dimethoxy-phenyl)-3-methyl-indol-1-ylmethyl]-phenoxy}-ethanol Oil; $^1$H NMR (DMSO) 7.46 (d, 2H, J=7.5 Hz), 7.39–7.35 (m, 2H), 7.31–7.28 (m, 1H), 7.16–7.06 (m, 3H), 6.82–6.72 (m, 5H), 6.68 (d, 1H, J=2.2 Hz), 6.61 (dd, 1H, J=2.4 Hz, 8.8 Hz), 5.0 (s, 1H), 4.88 (s, 2H), 4.85 (d, 1H, J=6.3 Hz), 4.69 (d, 1H, J=6.3 Hz), 3.63 (t, 2H, J=6.9 Hz), 3.58 (s, 3H), 3.46 (s, 3H), 3.40 (t, 2H, J=6.9 Hz), 1.80 (s, 3H).

Data for 3-methylindole Phenylethyl Bromides

Scheme 11

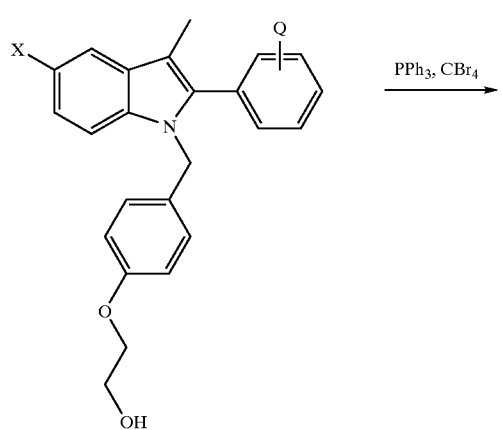

Example Nos. 35–45

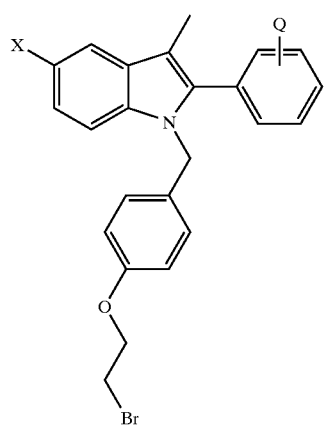

Example Nos. 47–57

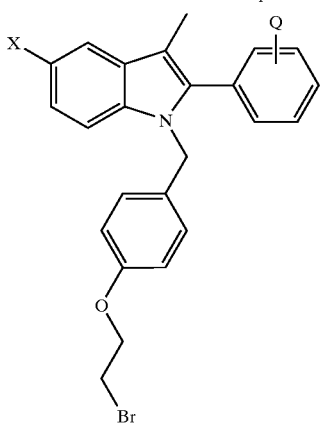

TABLE 4

| Example No. | X | Q |
|---|---|---|
| No. 47 | H | H |
| No. 48 | OMe | 4'-OMe |
| No. 49 | OBn | 4'-OEt |
| No. 50 | OBn | 4'-OBn |
| No. 51 | OBn | 4'-F |
| No. 52 | OBn | 3', 4'-OCH$_2$O— |
| No. 52a | OBn | 3'-OMe, 4'-OBn |

TABLE 4-continued

| Example No. | X | Q |
|---|---|---|
| No. 53 | OBn | 4'-O-iPr |
| No. 54 | OBn | 4'-OCp |
| No. 55 | OBn | 4'-CF$_3$ |
| No. 56 | OBn | 4'-CH$_3$ |
| No. 57 | OBn | 4'-Cl |

Experimental Procedure for 3-Methylindole Phenethyl Bromide

Synthesis

Method 5

Illustrated for Example No. 50

EXAMPLE NO. 50

5-Benzyloxy-2-(4-benzyloxy-phenyl)-1-[4-(2-bromo-ethoxy)-benzyl]-3-methyl-1H-indole To a solution of example No. 38 (3.3 g, 5.8 mmol) in THF (50 mL) was added CBr$_4$ (2.9 g, 8.7 mmol) and PPH$_3$ (2.3 g, 87 mmol). The reaction was stirred at rt for 3 h and then concentrated and chromatographed on silica gel using a gradient elution from EtOAc/hexane (1:4) to EtOAc to give 3.2 g of a white solid: Mp=131–134° C.; $^1$H NMR (DMSO) 7.64–7.30 (m, 10H), 7.29 (d, 2H, J=8.8 Hz), 7.20 (d, 1H, J=8.8 Hz), 7.12–7.09 (m, 3H), 6.80 (dd, 1H, J=8.8, 2.4 Hz), 6.77–6.73 (m, 4H), 5.16 (s, 2H), 5.13 (s, 2H), 5.11 (s, 2H), 4.20 (t, 2H, J=5.3 Hz), 3.73 (t, 2H, J=5.5 Hz), 2.15 (s, 3H); MS FAB 631/633 (M+H$^+$, Br present).

Physical Data for Indole Phenethyl Bromides

The following compounds were made according to scheme 11 as described in Method 5 using the appropriately substituted indole selected from No. 35–No. 45.

EXAMPLE NO. 47

1-[4-(2-bromo-ethoxy)-benzyl]-2-phenyl-3-methyl-1H-indole

Oil; $^1$H NMR (DMSO) 7.57–7.32 (m, 7H), 7.13–7.02 (m, 2H), 6.74 (s, 4H), 5.21 (s, 2H), 4.19 (t, 2H, J=5.2 Hz), 3.71 (t, 2H, J=5.5 Hz), 2.20 (s, 3H); MS eI m/z 419 (M+).

EXAMPLE NO. 48

5-Methoxy-2-(4-methoxy-phenyl)-1-[4-(2-bromo-ethoxy)-benzyl]-3-methyl-1H-indole

Oil; $^1$H NMR (DMSO) 7.27 (d, 2H, J=8.8 Hz), 7.17 (d, 1H, J=8.8 Hz), 7.03 (d, 2H, J=8.6 Hz), 6.99 (d, 1H, J=2.5 Hz), 6.80–6.69 (m, 5H), 5.14 (s, 2H), 4.19 (t, 2H, J=5.4 Hz), 3.78 (s, 3H), 3.76 (s, 3H), 3.72 (t, 2H, J=5.5 Hz), 2.16 (s, 3H); MS eI m/z 479 (M+).

EXAMPLE NO. 49

5-Benzyloxy-2-(4-ethoxy-phenyl)-1-[4-(2-bromo-ethoxy)-benzyl]-3-methyl-1H-indole Mp=118–120° C.; $^1$H NMR (DMSO) 7.45 (d, 2H, J=7.3 Hz), 7.41–7.26 (m, 5H), 7.17 (d, 1H, J=8.8 Hz), 7.11 (d, 1H, J=2.2 Hz), 7.01 (d, 2H, J=6.8 Hz), 6.78 (dd, 1H, J=8.8 Hz, J=2.4 Hz), 6.78–6.74 (m, 4H), 5.15 (s, 2H), 5.10 (s, 2H), 4.22–4.18 (m, 2H), 4.04 (q, 2H, J=6.8 Hz), 3.72 (t, 2H, J=5.5 Hz), 2.14 (s, 3H), 1.33 (t, 3H, J=7.0 Hz); MS eI m/z 569 (M+).

EXAMPLE NO. 51

5-Benzyloxy-1-[4-(2-bromo-ethoxy)-benzyl]-2-(4-fluoro-phenyl)-3-methyl-1H-indole Mp=114–116° C.; $^1$H NMR (DMSO) 7.47 (m, 2H), 7.45–7.20 (m, 8H), 7.14 (d, 1H, J=2.4 Hz), 6.83 (dd, 1H, J=2.7 Hz, 9.0 Hz), 6.80–6.70 (m, 4H), 5.16 (s, 2H), 5.11 (s, 2H), 4.19 (t, 2H, J=5.27 Hz), 3.72 (t, 2H, J=6.4 Hz), 2.15 (s, 3H); MS eI m/z 543 (M+); CHN calc for $C_{31}H_{27}BrFNO_2$.

EXAMPLE NO. 52

2-Benzo[1,3]dioxyl-5-yl-5-benzyloxy-1-[4-(2-bromo-ethoxy)-benzyl]-3-methyl-1H-indole Mp=133–136° C.; $^1$H NMR (DMSO) 7.45 (d, 2H, J=7.0 Hz), 7.41–7.38 (m, 2H), 7.35–7.30 (m, 1H), 7.19 (d, 1H, J=8.8 Hz), 7.11 (d, 1H, J=2.2 Hz), 7.00 (d, 1H, J=7.9 Hz), 6.90 (d, 1H, 1.4 Hz), 6.82–6.78 (m, 2H), 6.77 (s, 4H), 6.07 (s, 2H), 5.16 (s, 2H), 5.10 (s, 2H), 4.20 (t, 2H, J=5.5 Hz), 3.73 (t, 2H, J=5.2 Hz), 2.15 (s, 3H); MS eI m/z 569 (M+).

EXAMPLE NO. 52a

5-Benzyloxy-1-[4-(2-bromo-ethoxy)-benzyl]-2-(3-methoxy-4-benzyloxy-phenyl)-3-methyl-1H-indole Foam; $^1$H NMR (DMSO) 7.47–7.42 (m, 4H), 7.40–7.30 (m, 6H), 7.20 (d, 1H, J=8.8 Hz), 7.12–7.10 (m, 2H), 6.86–6.84 (m, 2H), 6.81 (dd, 1H, J=8.8 Hz, 2.4 Hz), 6.78 (s, 4H), 5.17 (s, 2H), 5.11 (s, 2H), 5.10 (s, 2H), 4.20 (t, 2H, J=5.0 Hz), 3.72 (t, 2H, J=5.4 Hz), 3.63 (s, 3H), 2.17 (s, 3H); MS FAB m/z 662 (M+H+).

EXAMPLE NO. 53

5-Benzyloxy-1-[4-(2-bromo-ethoxy)-benzyl]-2-(4-isopropoxy-phenyl)-3-methyl-1H-indole Mp=125–128° C.; $^1$H NMR (DMSO) 7.46 (d, 2H, J=7.7 Hz), 7.42–7.28 (m, 3H), 7.25 (d, 2H, J=8.7 Hz), 7.17 (d, 1H, J=8.7 Hz), 7.11 (d, 1H, J=2.4 Hz), 6.99 (d, 2H, J=8.6 Hz), 6.79 (dd, 1H, J=2.4 Hz, 8.8 Hz), 6.73 (s, 4H), 5.14 (s, 2H), 5.10 (s, 2H), 4.70–4.60 (m, 1H), 4.19 (t, 2H, J=5.3 Hz), 3.72 (t, 2H, J=4.4 Hz), 2.13 (s, 3H), 1.30 (d, 6H, J=5.9 Hz); MS eI m/z 583 (M+).

EXAMPLE NO. 54

5-Benzyloxy-1-[4-(2-bromo-ethoxy)-benzyl]-2-(4-cyclopentyloxy-phenyl)-3-methyl-1H-indole Mp=110–112° C.; 7.47 (d, 2H, J=7.0 Hz), 7.38 (t, 2H, J=7.0 Hz), 7.35–7.28 (m, 1H), 7.25 (d, 2H, J=8.8 Hz), 7.18 (d, 1H, J=8.8 Hz), 7.11 (d, 1H, J=2.4 Hz), 6.98 (d, 2H, J=8.6 Hz), 6.79 (dd, 1H, J=8.6 Hz, 2.4 Hz), 6.78–6.74 (m, 4H), 5.16 (s, 2H), 5.11 (s, 2H), 4.86–4.83 (m, 1H), 4.20 (t, 2H, J=5.3 Hz), 3.73 (t, 2H, J=5.5 Hz), 2.15 (s, 3H), 2.00–1.87 (m, 2H), 1.79–1.65 (m, 4H), 1.63–1.56 (m, 2H); IR (Kr) 2950, 2910, 1610 cm−1; MS eI m/z 609, 611 (M+, Br present).

EXAMPLE NO. 55

5-Benzyloxy-1-[4-(2-bromo-ethoxy)-benzyl]-3-methyl-2-(4-trifluoromethyl-phenyl)-1H-indole Mp=106–109° C.; $^1$H NMR (DMSO) 7.83 (d, 2H, J=8.1 Hz), 7.60 (d, 2H, J=7.9 Hz), 7.35–7.29 (m, 2H), 7.48 (d, 2H, J=8.6 Hz), 7.39 (d, 2H, J=7.0 Hz), 7.18 (d, 1H, J=2.2 Hz), 6.87 (dd, 1H, J=9.0 Hz, 2.6 Hz), 6.77–6.71 (m, 4H), 5.22 (s, 2H), 5.12 (s, 2H), 4.20 (t, 2H, J=5.3 Hz), 3.72 (t, 2H, J=5.3 Hz), 2.20 (s, 3H); IR (KBr) 2910, 2850, 1620 cm−1; MS eI m/z 595, 593 (M+)

EXAMPLE NO. 56

5-Benzyloxy-1-[4-(2-bromo-ethoxy)-benzyl]-3-methyl-2-(4-methyl-phenyl)-1H-indole Mp=82–95° C.; $^1$H NMR (DMSO) 7.46 (d, 2H, J=7.2 Hz), 7.45–7.18 (m, 8H), 7.12 (d, 1H, J=2.4 Hz), 6.81 (dd, 1H, J=2.4 Hz, 8.6 Hz), 6.73 (s, 4H), 5.15 (s, 2H), 5.10 (s, 2H), 4.19 (t, 2H, J=5.3 Hz), 3.72 (t, 2H, J=4.4 Hz), 2.34 (s, 3H), 2.15 (s, 3H); MS eI m/z 539 (M+).

EXAMPLE NO. 57

5-Benzyloxy-1-[4-(2-bromo-ethoxy)-benzyl]-3-methyl-2-(4-chloro-phenyl)-1H-indole $^1$H NMR (DMSO) 7.52 (d, 2H, J=8.6 Hz), 7.46 (d, 2H, J=6.8 Hz), 7.38 (m, 4H), 7.36 (m, 1H), 7.25 (d, 1H, J=9.0 Hz), 7.14 (d, 1H, J=2.4 Hz), 6.83 (dd, 1H, J=8.8 Hz, J=2.5 Hz), 6.72 (m, 4H), 5.17 (s, 2H), 5.11 (s, 2H), 4.19 (t, 2H, J=5.5 Hz), 3.72 (t, 2H, J=5.5 Hz), 2.16 (s, 3H); MS eI m/z 559 (N+).

Data for Some 3-Methylindole Phenylethyl Chlorides Used as Intermediates

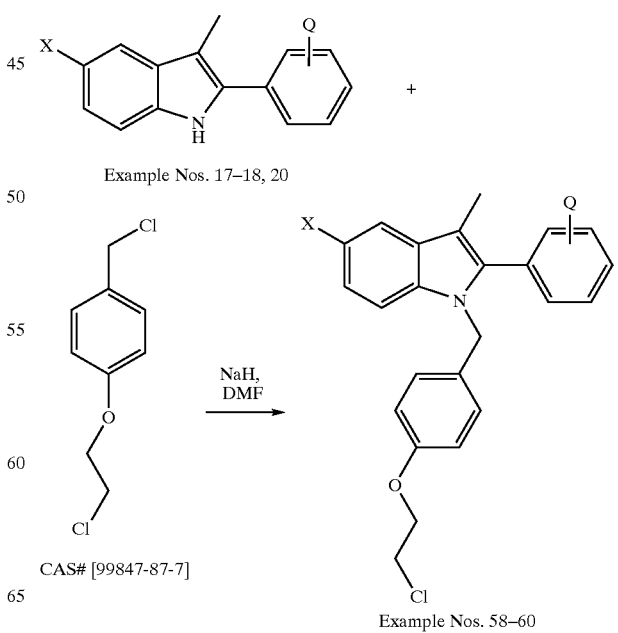

Scheme 12

Example Nos. 17–18, 20

CAS# [99847-87-7]

Example Nos. 58–60

-continued

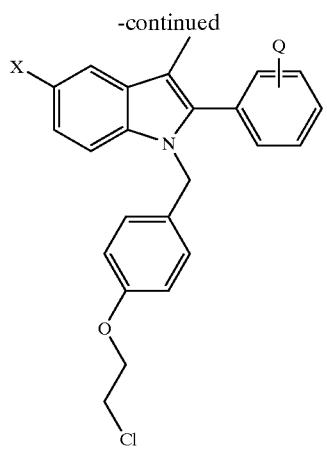

TABLE 5

| Example No. | X | Q |
|---|---|---|
| No. 58 | OBn | 3'-OBn |
| No. 59 | OBn | 3'-F, 4'-OBn |
| No. 60 | OBn | 4'-OCF₃ |

Experimental Procedure for 3-Methylindole Phenethylchloride

Synthesis

Method 5a

Illustrated for Example No. 58

5-Benzyloxy-2-(3-benzyloxy-phenyl)-1-[4-(2-chloro-ethoxy)-benzyl]-3-methyl-1H-indole To a solution of 9.7 g (0.0231 mol) of 5-benzyloxy-3-methyl-2-(3-benzyloxy-phenyl)-1H-indole (indole example No. 17) in 80 mL of dry DMF was added 0.85 g of sodium hydride (60% in mineral oil). After allowing this mixture to stir for 30 minutes (until no more bubbling was indicated), 4.8 g of 1-chloromethyl-4-(2-chloro-ethoxy)-benzene CAS No. [99847-87-7] was added. The reaction mixture was allowed to react at room temperature overnight 200 mL of ethyl acetate were added to the reaction mixture and then washed with water (3×100 mL). The organic solution was collected, washed with saturated brine, removed, dried over magnesium sulfate, filtered and evaporated to dryness in a rotary evaporator. The product was recrystallized in ethyl acetate.

Mp=125–127° C.; $^1$H NMR (DMSO) 7.48–7.46 (d, 2H, J=6.8 Hz), 7.40–7.35 (m, 7H), 7.33–7.28 (m, 2H), 7.23–7.21 (d, 1H, J=8.8 Hz), 7.13–7.12 (d, 1H, J=2.2 Hz), 7.07–7.04 (m, 1H), 6.94–6.92 (d, 2H, J=6.1 Hz), 6.83–6.80 (dd, 1H, J=2.5 Hz, J=6.3 Hz), 6.78–6.72 (m, 4H), 5.14 (s, 2H), 5.11 (s, 2H), 5.04 (s, 2H), 4.13–4.10 (t, 2H, J=5.1 Hz), 3.86–3.84 (t, 2H, J=5.1 Hz), 2.14 (s, 3H); IR 3420, 2900 cm$^{-1}$; MS eI m/z 587 (M+); CHN calcd for $C_{38}H_{34}ClNO_3$.

Physical Data for Indole Phenethyl Chlorides

The following compounds were made according to scheme 12 as described in Method 5a using the appropriately substituted indoles No. 18, No. 20.

EXAMPLE NO. 59

5-Benzyloxy-2-(4-benzyloxy-3-fluoro-phenyl)-1-[4-(2-chloro-ethoxy)-benzyl]-3-methyl-1H-indole Mp=88–91° C.; $^1$H NMR (DMSO) 7.49–7.43 (m, 4H), 7.43–7.25 (m, 7H), 7.26–7.21 (m, 2H), 7.13–7.09 (m, 2H), 6.88–6.72 (m, 5H), 5.21 (s, 2H), 5.18 (s, 2H), 5.11 (s, 2H), 4.13 (t, 2H, J=5.2 Hz), 3.87 (t, 2H, J=5.2 Hz), 2.16 (s, 3H); MS eI m/z 605 (M+); CHN calcd for $C_{38}H_{33}ClFNO_3$.

EXAMPLE NO. 60

5-Benzyloxy-1-[4-(2-chloro-ethoxy)-benzyl]-3-methyl-2-(4-trifluoromethoxy-phenyl)-1H-indole Mp=108–110° C.; $^1$H NMR (DMSO) 7.49–7.48 (m, 6H), 7.40–7.25 (m, 4H), 7.17–7.16 (d, 1H, J=2.9 Hz), 6.88–6.84 (m, 1H), 6.77–6.72 (m, 4H), 5.20 (s, 2H), 5.14–5.13 (d, 2H, J=2.3 Hz), 4.16–4.11 (m, 2H), 3.89–3.84 (m, 2H), 2.19–2.17 (m, 3H); IR 3400, 2900, 1600 cm$^{-1}$; MS eI m/z 566 (M+); CHN calcd for $C_{32}H_{27}ClF_3NO_3+0.25H_2O$.

Aminoethoxy indoles

Scheme 13

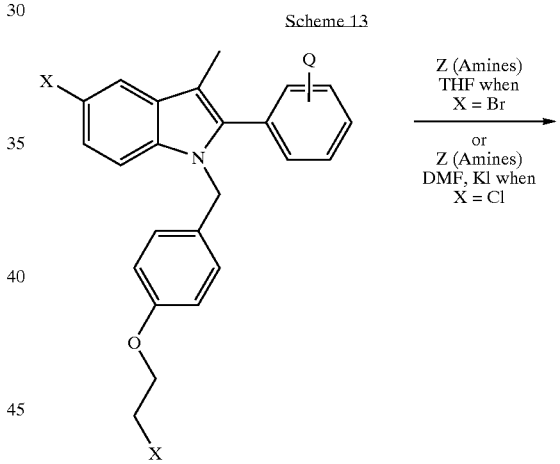

Example Nos. 47–60

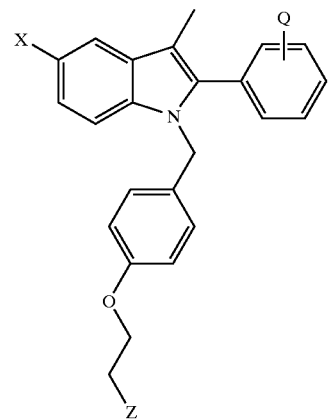

Example Nos. 61–84

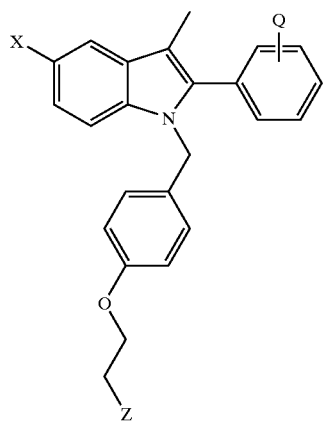

TABLE 6

| Example No. | X | O | Z |
|---|---|---|---|
| No. 61 | OBn | 4'-OEt | piperidine |
| No. 62 | OBn | H | azepane |
| No. 63 | OBn | 4'-OBn | piperidine |
| No. 64 | OBn | 4'-OBn | azepane |
| No. 65 | OBn | 4'-OBn | N(iPr)$_2$ |
| No. 66 | OBn | 4'-OBn | N(Me)(n-Bu) |
| No. 66a | OBn | 4'-OBn | N(Me)$_2$ |
| No. 67 | OBn | 4'-OBn | 2-methylpiperidine |
| No. 68 | OBn | 4'-OBn | 3-methylpiperidine |

TABLE 6-continued

| Example No. | X | O | Z |
|---|---|---|---|
| No. 69 | OBn | 4'-OBn | 4-methylpiperidine |
| No. 70 | OBn | 4'-OBn | 2,6-dimethylpiperidine |
| No. 71 | OBn | 4'-OBn | 3,5-dimethyl bicyclic amine |
| No. 71a | OBn | 4'-OBn | bicyclic amine |
| No. 72 | OBn | 4'-F | azepane |
| No. 72a | OBn | 4'-F | piperidine |
| No. 72b | OBn | 4'-Cl | piperidine |
| No. 73 | OBn | 3',4'-OCH$_2$O— | piperidine |
| No. 74 | OBn | 4'-O-iPr | piperidine |
| No. 75 | OBn | 4'-CH$_3$ | piperidine |
| No. 76 | OBn | 3'-OBn | piperidine |
| No. 77 | OBn | 3'-OBn | azepane |
| No. 78 | OBn | 4'-OBn,3'-F | piperidine |

TABLE 6-continued

| Example No. | X | O | Z |
|---|---|---|---|
| No. 79 | OBn | 4'-OBn,3'-F | azepan-1-yl (7-membered N ring) |
| No. 80 | OBn | 3'-OMe | piperidin-1-yl |
| No. 81 | OBn | 4'-OCF$_3$ | piperidin-1-yl |
| No. 82 | OBn | 4'-OBn | cyclohexyl-NH– |
| No. 83 | OBn | 4'-OBn | piperazin-1-yl |
| No. 84 | OBn | 3'-OMe | azepan-1-yl |

Experimental Procedure for 3-Methyl aminoethoxyindole Synthesis

Method 6

Illustrated for Example No. 63

Substitution of the Bromide

5-Benzyloxy-2-(4-benzyloxy-phenyl)-3-methyl-1-[4-(2-piperidin-1-yl-ethoxy)-benzyl]-1H-indole A solution of example No. 50 (3.2 g, 5.0 mmol) in THF (50 mL) was treated with piperidine (5.0 mL, 50 mmol) and heated to reflux. After 5 hours, the reaction mixture was concentrated and taken up in EtOAc, washed with saturated NaHCO$_3$, dried over MaSO$_4$ and column chromatogaphed on silica gel using a gradient elution of EtOAc/Hexane to EtOAc. The product (2.7 g) was a white solid with a Mp=93–95° C.; $^1$H NMR (DMSO) 7.48–7.46 (m, 4H), 7.42–7.38 (m, 4H), 7.38–7.32 (m, 2H), 7.29 (d, 2H, J=8.8 Hz), 7.19 (d, 1H, J=9.0 Hz), 7.12–7.10 (m, 3H), 6.80 (dd, 1H, J=8.8, 2.4 Hz), 6.73 (s, 4H), 5.15 (s, 2H), 5.13 (s, 2H), 5.11 (s, 2H), 3.93 (t, 2H, J=5.7 Hz), 2.60–2.50 (m, 2H), 2.41–2.30 (m, 4H), 2.15 (s, 3H), 1.47–1.42 (m, 4H), 1.36–1.32 (m, 2H); MS FAB 637 (M+H$^+$).

Alternative Procedure

Method 6a

Substitution of Chlorides

Synthesis Illustrated for Product No. 76

EXAMPLE NO. 76

5-Benzyloxy-2-(3-benzyloxy-phenyl)-3-methyl-1-[4-(2-piperidin-1-yl-ethoxy)-benzyl]-1H-indole To a solution of 1.1 g (0.00953 mol) of 5-benzyloxy-2-(3-benzyloxy-phenyl-1-[4-(2-chloro-ethoxy)-benzyl]-3-methyl-1H-indole (example No. 58) in 10 mL of DMF was added 1.1 mL (0.0112 mol) of piperidine, and 0.93 g (00561 mol) of potassium iodide. The reaction mixture was heated to ~40–50° C. for 4 hours. After cooling the reaction mixture to room temperature, 150 mL of ethyl acetate were added and the mixture was washed with water (3×100 mL). The organic solution was collected, washed with saturated brine, removed, dried over magnesium sulfate, filtered and evaporated to yield 1.0 g of product of the product after purification.

Mp=125–126° C.; $^1$H NMR (DMSO) 7.48–7.45 (d, 2H, J=7.2 Hz), 7.41–7.35 (m, 7H), 7.33–7.28 (m, 2H), 7.23–7.21 (d, 1H, J=9.0 Hz), 7.13–7.12 (d, 1H, J=2.4 Hz), 7.06–7.03 (m, 1H), 6.95–6.91 (m, 2H), 6.83–6.80 (dd, 1H, J=2.4 Hz, J=6.3 Hz), 6.75–6.70 (m, 4H), 5.13 (s, 2H), 5.11 (s, 2H), 5.02 (s, 2H), 3.93–3.90 (t, 2H, J=6.0 Hz), 2.56–2.53 (t, 2H, J=5.9 Hz), 2.49–2.48 (m, 4H), 2.14 (s, 3H), 1.46–1.40 (m, 4H), 1.35–1.31 (m, 2H); IR (KBr) 3400, 2900 cm$^{-1}$; MS eI m/z 636 (M+); CHN calcd for $C_{43}H_{44}N_2O_3$+0.25H$_2$O.

Physical Data for the Amine Substituted Compounds

The following compounds were prepared by scheme 13 using method 6. Except for examples No. 76–No. 84 which were prepared using method 6a.

EXAMPLE NO. 61

5-Benzyloxy-2-(4-ethoxy-phenyl)-3-methyl-1-[4-(2-piperidin-1-yl-ethoxy)-benzyl]-1H-indole Mp 188–191° C.; $^1$H NMR (DMSO) 7.45 (d, 2H, J=7.3 Hz), 7.40–725 (m, 5H), 7.17 (d, 1H, J=8.8 Hz), 7.11 (d, 1H, J=2.2 Hz), 7.01 (d, 2H, J=6.8 Hz), 6.78 (dd, 1H, J=8.8 Hz, J=2.4 Hz), 6.73 (s, 4H), 5.15 (s, 2H), 5.10 (s, 2H), 4.05 (q, 2H, J=6.8 Hz), 3.93 (t, 2H, J=6.0 Hz), 2.55 (t, 2H, J=5.7 Hz), 2.41–2.35 (m, 4H), 2.14 (s, 3H), 1.46–1.40 (m, 4H), 1.38–1.30 (m, 5H); MS eI m/z 574 (M+).

EXAMPLE NO. 62

5-Benzyloxy-2-phenyl-3-methyl-1-[4-(2-azepan-1-yl-ethoxy)-benzyl]-1H-indole

Oil; $^1$H NMR (DMSO) 7.50–7.43 (m, 4H), 7.42–7.37 (m, 5H), 7.33–7.30 (m, 1H), 7.22 (d, 1H, J=8.8 Hz), 7.14 (d, 1H, J=2.4 Hz), 6.81 (d, 1H, J=6.6 Hz), 6.72 (s, 4H), 5.18 (s, 2H), 5.11 (s, 2H), 3.90 (t, 2H, J=6.1 Hz), 2.81–2.75 (m, 2H), 2.68–2.59 (m, 4H), 2.16 (s, 3H), 1.58–1.43 (m, 8H); MS eI m/z 544 (M+).

EXAMPLE NO. 64

5-Benzyloxy-2-(4-benzyloxy-phenyl)-3-methyl-1-[4-(2-azepan-1-yl-ethoxy)-benzyl]-1H-indole Mp=106–107° C.; $^1$H NMR (DMSO) 7.47 (d, 4H, J=8.8 Hz), 7.41–7.36 (m, 4H), 7.36–7.30 (m, 2H), 7.29 (d, 2H, J=8.8 Hz), 7.19 (d, 1H, J=8.8 Hz), 7.14–7.10 (m, 3H), 6.80 (dd, 1H, J=8.8 Hz), 6.73 (s, 4H), 5.15 (s, 2H), 5.13 (s, 2H), 5.11 (s, 2H), 3.90 (t, 2H, J=5.9 Hz), 2.76 (t, 2H, J=5.9 Hz), 2.64–2.56 (m, 4H), 2.15 (s, 3H), 1.58–1.44 (m, 8H); MS FAB m/z 651 (M+H+).

EXAMPLE NO. 65

5-Benzyloxy-2-(4-benzyloxy-phenyl)-3-methyl-1-[4-(2-diisopropylamino-1-yl-ethoxy)-benzyl]-1H-indole Mp=148–150° C.; $^1$H NMR (DMSO) 7.47 (d, 4H, J=8.8 Hz), 7.41–7.36 (m, 4H), 7.36–7.32 (m, 2H), 7.28 (d, 2H, J=8.8 Hz), 7.19 (d, 1H, J=9.0 Hz), 7.13–7.08 (m, 3H), 6.80 (dd, 1H, J=8.8 Hz, 2.4 Hz), 6.76–6.68 (m, 4H), 5.14 (s, 2H), 5.13 (s, 2H), 5.11 (s, 2H), 3.75 (t, 2H, J=7.0 Hz), 2.95 (m, 2H), 2.67 (t, 2H, J=7.0 Hz), 2.15 (s, 3H), 0.93 (d, 12H, J=6.4 Hz); MS FAB m/z 653 (M+H+).

EXAMPLE NO. 66

5-Benzyloxy-2-(4-benzyloxy-phenyl)-3-methyl-1-[4-(2-butyl-methylamino-1-ylethoxy)-benzyl]-1H-indole Mp=101–104° C.; $^1$H NMR (DMSO) 7.45 (d, 4H, J=7.5 Hz), 7.40–7.25 (m, 8H), 7.19 (d, 1H, J=8.8 Hz), 7.12–7.08 (m, 3H), 6.80 (dd, 1H, J=65 Hz, J=24 Hz), 6.72 (s, 4H), 5.14 (s, 2H), 5.13 (s, 2H), 5.10 (s, 2H), 3.91 (t, 2H, J=5.9 Hz), 2.64–2.59 (m, 2H), 2.35–2.29 (m, 2H), 2.17 (s, 3H), 2.14 (s, 3H), 1.40–1.31 (m, 2H), 1.25–1.19 (m, 2H), 0.83 (t, 3H, 7.2 Hz); MS eI m/z 638 (M+).

EXAMPLE NO. 66a

5-Benzyloxy-2-(4-benzyloxy-phenyl)-3-methyl-1-{4-dimethylamino)-ethoxy]-benzyl}-1H-indole Mp=123–124° C.

EXAMPLE NO. 67

5-Benzyloxy-2-(4-benzyloxy-phenyl)-3-methyl-1-{4-[2-(3-methyl-piperidin-1-yl)-ethoxy]-benzyl}-1H-indole Mp=121° C.

EXAMPLE NO. 68

5-Benzyloxy-2-(4-benzyloxy-phenyl)-3-methyl-1-{4-[2-(3-methyl-piperidin-1-yl)-ethoxy]-benzyl}-1H-indole Mp=90° C.

EXAMPLE NO. 69

5-Benzyloxy-2-(4-benzyloxy-phenyl)-3-methyl-1-{4-[2-(4-methyl-piperidin-1-yl)-ethoxy]-benzyl}-1H-indole Mp=98° C.; $^1$H NMR (DMSO) 7.46 (d, 4H, J=7.2 Hz), 7.42–7.36 (m, 4H), 7.36–7.31 (m, 2H), 7.28 (d, 2H, J=8.6 Hz), 7.19 (d, 1H, J=9.0 Hz), 7.12–7.10 (m, 3H), 6.80 (dd, 1H, J=8.8 Hz, 2.4 Hz), 6.73 (s, 4H), 5.15 (s, 2H), 5.13 (s, 2H), 5.11 (s, 2H), 3.93 (t, 2H, J=5.9 Hz), 2.85–2.78 (m, 2H), 2.62–2.56 (m, 2H), 2.15 (s, 3H), 1.97–1.87 (m, 2H), 1.55–1.47 (m, 2H), 1.30–1.20 (m, 1H), 1.15–1.02 (m, 2H), 0.85 (d, 3H, J=6.6 Hz); MS esI m/z 651 (M+1)+.

EXAMPLE NO. 70

5-Benzyloxy-2-(4-benzyloxy-phenyl)-3-methyl-1{4-[2-((cis)-2,6-Dimethyl-piperidin-1-yl)-ethoxy]-benzyl}-1H-indole Mp=106–107° C.; $^1$H NMR (DMSO) 7.46 (d, 4H, J=8.1 Hz), 7.42–7.36 (m, 4H), 7.37–7.31 (m, 2H), 7.29 (d, 2H, J=8.8 Hz), 7.18 (d, 1H, J=8.8 Hz), 7.14–7.09 (m, 3H), 6.80 (dd, 1H, J=8.8 Hz, 2.4 Hz), 6.72 (s, 4H), 5.14 (s, 2H), 5.13 (s, 2H), 5.11 (s, 2H), 3.84 (t, 2H, J=7.0 Hz), 2.84 (t, 2H, J=6.6 Hz), 2.44–2.37 (m, 2H), 2.15 (s, 3H), 1.60–1.43 (m, 3H), 1.32–1.18 (m, 1H), 1.16–1.06 (m, 2H), 1.01 (d, 6H, J=6.2 Hz).

EXAMPLE NO. 71

5-Benzyloxy-2-(4-benzyloxy-phenyl)-3-methyl-{4-[2-(1,3,3-trimethyl-6-aza-bicyclo[3,2,1]oct-6-yl) ethoxy]-benzyl}-1H-indole Mp=107° C.; MS ESI m/z 705 (M+1)+

EXAMPLE NO. 71a (1S,4R)-5-Benzyloxy-2-(4-benzyloxy-phenyl)-3-methyl{4-[2-(2-Aza-bicyclo[2.2.1]hept-2-yl)-ethoxy]-benzyl}-1H-indole The (1S,2R)-2-aza-bicyclo [2.2.1] heptane used to substitute the bromide was prepared according to the procedure outlined in Syn. Comm. 26(3), 577–584 (1996). Mp=95–100° C.; $^1$H NMR (DMSO) 7.32–6.55 (m, 21H), 5.10–4.90 (m, 6H), 3.69 (t, 2H, J=5.9 Hz), 2.65–2.5 (m, 3H), 2.10 (s, 2H), 2.0 (s, 3H), 1.50–1.0 (m, 7H).

EXAMPLE NO. 72

5-Benzyloxy-2-(4-flouro-phenyl)-3-methyl-1-[4-(2-azepan-1-yl-ethoxy)-benzyl]-1H-indole Oil; $^1$H NMR (DMSO) 7.50–7.43 (m, 2H), 7.42–7.33 (m, 4H), 7.32–7.20 (m, 4H), 7.13 (d, 1H, J=2.4 Hz), 6.83 (dd, 1H, J=2.4 Hz, 6.7 Hz), 6.71 (s, 4H), 5.14 (s, 2H), 5.11 (s, 2H), 3.89 (t, 2H, J=5.9 Hz), 3.20 (m, 4H), 2.74 (t, 2H, J=6.0 Hz), 2.15 (s, 3H), 1.60–1.40 (m, 8H); MS eI m/z 562 (M+).

EXAMPLE NO. 72a

5-Benzyloxy-2-(4-flouro-phenyl)-3-methyl-1-[4-(2-piperidin-1-yl-ethoxy)-benzyl]-1H-indole Oil; $^1$H NMR (DMSO) 7.32–6.53 (m, 16H), 5.00 (s, 2H), 4.96 (s, 2H), 3.77 (t, 2H, J=5.8 Hz), 3.22–3.14 (m, 4H), 2.40 (t, 2H, J=5.8 Hz), 2.0 (s, 3H), 1.29–1.17 (m, 6H).

EXAMPLE NO. 72b

5-Benzyloxy-2-(4-chloro-phenyl)-3-methyl-1-[4-(2-piperidin-1-yl-ethoxy)-benzyl]-1H-indole Oil; $^1$H NMR (DMSO) 7.52 (d, 2H, J=8.6 Hz), 7.46 (d, 2H, J=6.8 Hz), 7.41–7.37 (m, 4H), 7.35–7.29 (m, 1H), 7.25 (d, 1H, J=9.0 Hz), 7.14 (d, 1H, J=2.4 Hz), 6.83 (dd, 1H, J=8.8 Hz, 2.5 Hz), 6.72–6.65 (m, 4H), 5.16 (s, 2H), 5.11 (s, 2H), 3.90 (t, 2H, J=5.9 Hz), 2.55 (t, 2H, J=6.0 Hz), 2.41–2.26 (m, 4H), 2.16 (s, 3H), 1.44–1.39 (m, 4H), 1.38–1.29 (m, 2H); MS eI m/z 564 (M+).

EXAMPLE NO. 73

5-Benzyloxy-2-[3,4-methylenedioxy-phenyl]-3-methyl-1-[4-(2-piperidin-1-yl-ethoxy)-benzyl]-1H-indole Foam; $^1$H NMR (DMSO) 7.45 (d, 2H, J=7.0 Hz), 7.41–7.37 (m, 2H), 7.33–7.29 (m, 1H), 7.19 (d, 1H, J=8.8 Hz), 7.11 (d, 1H, J=2.2 Hz), 7.00 (d, 1H, J=7.9 Hz), 6.90 (d, 1H, 1.4 Hz), 6.82–6.78 (m, 2H), 6.74 (s, 4H), 6.07 (s, 2H), 5.16 (s, 2H), 5.10 (s, 2H), 3.93 (t, 2H, J=6.0 Hz), 2.56 (t, 2H, J=6.0 Hz), 2.41–2.35 (m, 4H), 2.15 (s, 3H), 1.48–1.41 (m, 4H), 1.38–1.28 (m, 2H); MS eI m/z 574 (M+).

EXAMPLE NO. 74

5-Benzyloxy-2-[4-isopropoxy-phenyl]-3-methyl-1-[4-(2-piperidin-1-yl-ethoxy)-benzyl]-1H-indole Foam; $^1$H NMR (DMSO) 7.46 (d, 2H, J=7.7 Hz), 7.42–7.28 (m, 3H), 7.25 (d, 2H, J=8.7 Hz), 7.17 (d, 1H, J=8.7 Hz), 7.11 (d, 1H, J=2.4 Hz), 6.99 (d, 2H, J=8.6 Hz), 6.79 (dd, 1H, J=2.4 Hz, 8.8 Hz), 6.73 (s, 4H), 5.14 (s, 2H), 5.10 (s, 2H), 4.70–4.60 (m, 1H), 3.92 (t, 2H, J=5.7 Hz), 2.55 (t, 2H, 5.7 Hz), 2.40–2.30 (bs, 4H), 2.15 (s, 3H), 1.50–1.40 (m, 4H), 1.40–1.30 (m, 2H), 1.28 (d, 6H, J=6.2 Hz); MS eI m/z 588 (M+).

EXAMPLE NO. 75

5-Benzyloxy-2-[4-methyl-phenyl]-3-methyl-1-[4-(2-piperidin-1-yl-ethoxy)-benzyl]-1H-indole Oil; $^1$H NMR (DMSO) 7.46 (d, 2H, J=7.2 Hz), 7.45–7.18 (m, 8H), 7.12 (d, 1H, J=2.4 Hz), 6.81 (dd, 1H, J=2.4 Hz, 8.6 Hz), 6.73 (s, 4H), 5.15 (s, 2H), 5.10 (s, 2H), 3.92 (t, 2H, J=5.9 Hz), 2.55 (t, 2H, J=5.9 Hz), 2.45–2.30 (m, 7H), 2.10 (s, 3H), 1.50–1.40 (m, 4H), 1.48–1.35 (m, 2H); MS eI m/z 544 (M+).

EXAMPLE NO. 77

1-[4-(2-Azepan-1-yl-ethoxy)-benzyl]-5-benzyloxy-2-(3-benzyloxy-phenyl)-3-methyl-1H-indole Mp=103–105° C.; $^1$H NMR (DMSO) 7.47–7.45 (d, 2H, J=8.1 Hz), 7.41–7.35 (m, 7H), 7.32–7.29 (t, 2H, 7.0 Hz), 7.23–7.21 (d, 1H, J=8.7 Hz), 7.13–7.12 (d, 1H, J=2.1 Hz), 7.06–7.03 (m, 1H), 6.95–6.91 (m, 2H, 6.83–6.80 (m, 1H), 6.75–6.73 (m, 4H), 5.13 (s, 2H), 5.11 (s, 2H), 5.02 (s, 2H), 3.90–3.87 (t, 2H, J=6.0 Hz), 2.76–2.73 (t, 2H, J=6.0 Hz), 2.49–2.48 (m, 4H); 2.13 (s, 3H), 1.51 (s, 8H); IR 3400, 2900 cm$^{-1}$; MS eI m/z 650 (M+); CHN calcd for C$_{44}$H$_{46}$N$_2$O$_3$.

EXAMPLE NO. 78

5-Benzyloxy-2-(4-benzyloxy-3-fluoro-phenyl)-3-methyl-1-[4-(2-piperidin-1-yl-ethoxy)-benzyl]-1H-indole Mp 125–128° C.; $^1$H NMR (DMSO) 7.50–7.45 (m, 4H), 7.43–7.28 (m, 7H), 7.26–7.20 (m, 2H), 7.14–7.09 (m, 2H), 6.82 (dd, 1H, J=2.4 Hz, 8.8 Hz), 6.72 (s, 4H), 5.21 (s, 2H), 5.16 (s, 2H), 5.11 (s, 2H), 3.94 (t, 2H, J=5.8 Hz), 2.62–2.56 (m, 2H), 2.41–2.36 (m, 4H), 2.15 (s, 3H), 1.45–1.40 (m, 4H), 1.40–1.31 (m, 2H); MS eI m/z 654 (M+); CHN clcd for C$_{43}$H$_{43}$FN$_2$O$_3$.

EXAMPLE NO. 79

5-Benzyloxy-2-(4-benzyloxy-3-fluoro-phenyl)-3-methyl-1-(4-(2-azepan-1-yl-ethoxy)-benzyl]-1H-indole Mp=122–124° C.; $^1$H NMR (DMSO) 7.50–7.28 (m, 10H), 7.26–7.20 (m, 2H), 7.15–7.10 (m, 2H), 6.88–6.76 (m, 2H), 6.70 (s, 4H), 5.22 (s, 2H), 5.16 (s, 2H), 5.11 (s, 2H), 3.92–3.86 (m, 2H), 2.82–2.65 (m, 2H), 2.65–2.55 (m, 4H), 2.15 (s, 3H), 1.60–1.4 (m, 8H); MS eI m/z 668 (M+); CHN calcd for C$_{44}$H$_{45}$FN$_2$O$_3$.

EXAMPLE NO. 80

5-Benzyloxy-2-(3-methoxy-phenyl-1-[4-(2-piperidin-1-yl-ethoxy)-benzyl]-3-methyl-1H-indole Mp 86–87° C.; $^1$H NMR (DMSO) 7.50–7.49 (m, 2H), 7.46–7.31 (m, 4H), 7.24–7.21 (d, 1H, J=8.8 Hz), 7.15–7.14 (d, 1H, J=2.3 Hz), 7.00–6.93 (m, 2H), 6.88–6.81 (m, 2H), 6.75 (s, 4H), 5.18 (s, 2H), 5.12 (s, 2H), 3.96–3.92 (t, 2H, J=5.9 Hz), 3.71 (s, 3H), 2.59–2.55 (t, 2H, J=5.8 Hz), 2.37 (s, 4H), 2.18 (s, 3H), 1.49–1.42 (m, 4H), 1.37–1.34 (m, 2H); MS eI m/z 561 (M+); CHN calcd for C$_{37}$H$_{40}$N$_2$O$_3$+0.25H$_2$O.

EXAMPLE NO. 81

5-Benzyloxy-3-methyl-1-[4-(2-piperidin-1-yl-ethoxy)-benzyl]-2-(4-trifluoromethoxy-phenyl)-1H-indole Mp=107–108° C.;

$^1$H NMR (DMSO) 7.52–7.45 (m, 6H), 7.41–7.26 (m, 4H), 7.17–7.16 (d, 1H, J=2.3 Hz), 6.87–6.84 (dd, 1H, J=2.3 Hz, J=6.4 Hz), 6.75–6.68 (m, 4H), 5.18 (s, 2H), 5.13 (s, 2H), 3.95–3.91 (t, 2H, J=5.9 Hz), 2.58–2.54 (t, 2H, J=5.9 Hz), 2.38–2.34 (m, 4H), 2.17–2.15 (s, 3H), 1.49–1.42 (m, 4H), 1.35–1.34 (d, 2H, J=4.9 Hz); IR 3400, 2900, 1600 cm$^{-1}$; MS eI m/z 615 (M+); CHN calcd for C$_{37}$H$_{37}$F$_3$N$_2$O$_3$.

EXAMPLE NO. 82

(2-{4-[5-Benzyloxy-2-(4-benzyloxy-phenyl)-3-methyl-indol-1-ylmethyl]-phenoxy}-ethyl)-cyclohexyl-amine Mp=87–90° C.; $^1$H NMR (DMSO) 7.46 (dd, 4H, J=6.9 Hz, 0.6 Hz), 7.42–7.27 (m, 9H), 7.19 (d, 1H, J=9 Hz), 7.14–7.08 (m, 3H), 6.80 (dd, 1H, J=6.4 Hz, 2.4 Hz), 6.75–6.70 (m, 4H), 5.15 (s, 2H), 5.13 (s, 2H), 5.13 (s, 2H), 3.89 (t, 2H, J=5.6), 2.84 (m, 2H), 2.48 (m, 1H), 2.14 (s, 3H), 1.80 (m, 2H), 1.65 (m, 2H), 1.61 (m, 1H), 0.96–1.19 (m, 5H); MS eI m/z 650 (M+); CHN calcd for C$_{44}$H$_{46}$N$_2$O$_4$.

EXAMPLE NO. 83

5-Benzyloxy-2-(4-benzyloxy-phenyl)-3-methyl-1-{4-methylpiperazin-1-yl)-ethoxy]-benzyl}-1H-indole Mp=88–91° C.; $^1$H NMR (DMSO) 7.47 (m, 4H), 7.26–7.42 (m, 8H), 7.19 (d, 1H, J=8.8), 7.10–1.12 (m, 3H), 6.80 (q, 1H, J=6.3 Hz, 2.4 Hz), 6.73 (m, 4H), 5.15 (s, 2H), 5.13 (s, 2H), 5.11 (s, 2H), 3.94 (t, 2H, J=5.9 Hz), 2.59 (t, 2H), 2.42 (m, 4H), 2.29 (m, 4H), 2.15 (s, 3H), 2.12 (s, 3H); MS eI m/z 652 (M+); CHN calcd for C$_{43}$H$_{45}$N$_3$O$_3$.

EXAMPLE NO. 84

1-[4-(3-Azpan-1-yl-ethoxy)-benzyl]-5-benzyloxy-2-(3-methoxy-phenyl)-3-methyl-1H-indole Mp=103–105° C.; $^1$H NMR (DMSO) 7.47–7.45 (d, 2H, J=8.1 Hz), 7.41–7.35 (m, 7H), 7.32–7.29 (t, 2H, 7.0 Hz), 7.23–7.21 (d, 1H, J=8.7 Hz), 7.13–7.12 (d, 1H, J=2.1 Hz), 7.06–7.03 (m, 1H), 6.95–6.91 (m, 2H), 6.83–6.80 (m, 1H), 6.75–6.73 (m, 4H), 5.13 (s, 2H), 5.11 (s, 2H), 5.02 (s, 2H), 3.90–3.87 (t, 2H, J=6.0 Hz), 2.76–2.73 (t, 2H, J=6.0 Hz), 2.49–2.48 (m, 4H), 2.13 (s, 3H), 1.51 (s, 8H); IR 3400, 2900 cm$^{-1}$; MS eI m/z 650 (M+); CHN calcd for $C_{44}H_{46}N_2O_3$.

Data and Procedures for Compounds From Table 11 (ER Receptor Data Table, Infra) of Text

TABLE 7

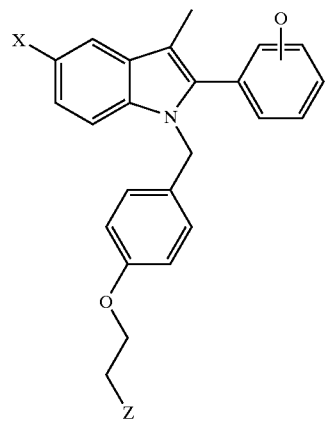

| Example No. | X | O | Z |
|---|---|---|---|
| No. 85 | H | H | piperidine |
| No. 86 | H | 4'-OH | piperidine |
| No. 87 | OH | H | piperidine |
| No. 88 | OMe | 4'-OH | piperidine |
| No. 89 | OH | 4'-OMe | piperidine |
| No. 90 | OMe | 4'-OMe | piperidine |
| No. 91 | OMe | 4'-OMe | azepane |
| No. 92 | OH | 4'-OEt | piperidine |

TABLE 7-continued

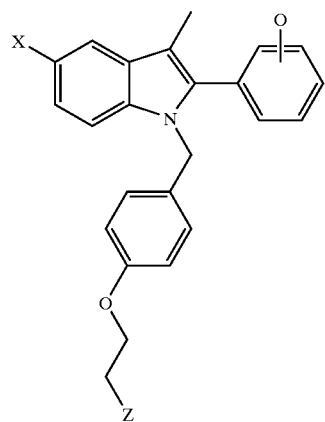

| Example No. | X | O | Z |
|---|---|---|---|
| No. 93 | OH | 4'-OEt | azepane |
| No. 94 | F | 4'-OH | piperidine |
| No. 95 | OH | H | azepane |
| No. 96 | OH | 4'-OH | pyrrolidine |
| No. 97 | OH | 4'-OH | piperidine |
| No. 98 | OH | 4'-OH | azepane |
| No. 99 | OH | 4'-OH | azocane |
| No. 100 | OH | 4'-OH | N(CH3)2 |
| No. 101 | OH | 4'-OH | N(Et)2 |
| No. 102 | OH | 4'-OH | N(Pr)2 |

TABLE 7-continued
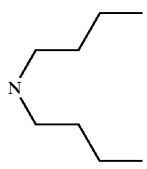
| Example No. | X | O | Z |
|---|---|---|---|
| No. 103 | OH | 4'-OH | 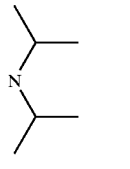 |
| No. 104 | OH | 4'-OH | 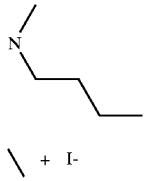 |
| No. 105 | OH | 4'-OH | 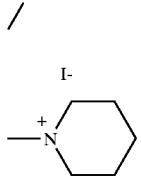 |
| No. 106 | OH | 4'-OH | 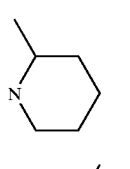 |
| No. 107 | OH | 4'-OH | 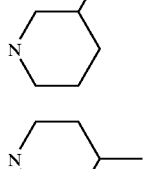 |
| No. 108 | OH | 4'-OH |  |
| No. 109 | OH | 4'-OH | 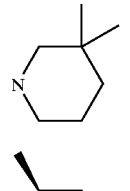 |
| No. 110 | OH | 4'-OH | 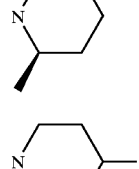 |
TABLE 7-continued
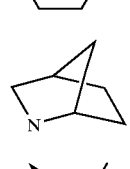
| Example No. | X | O | Z |
|---|---|---|---|
| No. 111 | OH | 4'-OH | 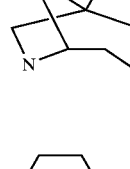 |
| No. 112 | OH | 4'-OH | 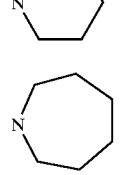 |
| No. 113 | OH | 4'-OH | 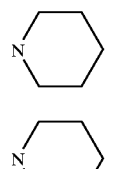 |
| No. 114 | OH | 4'-OH |  |
| No. 115 | OH | 4'-OH | 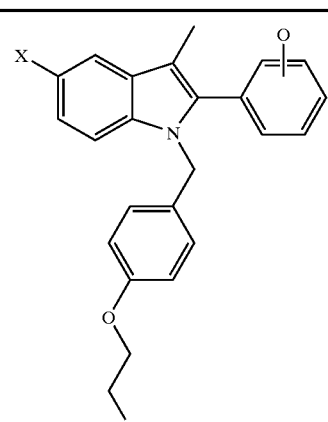 |
| No. 116 | OH | 4'-F | 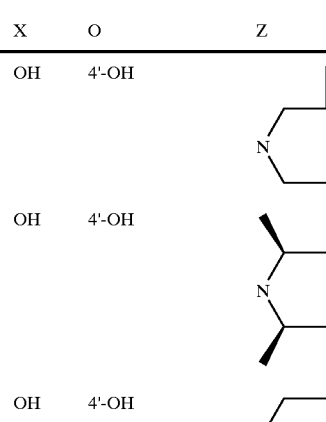 |
| No. 117 | OH | 4'-F | 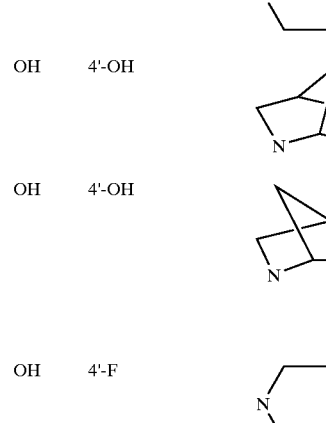 |
| No. 118 | OH | 3'-OMe,4'-OH | 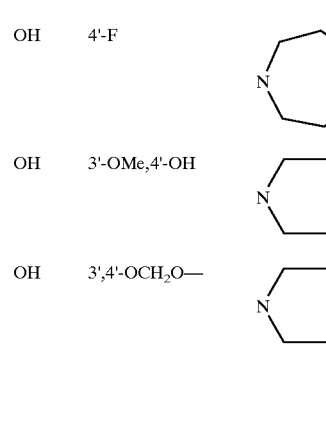 |
| No. 119 | OH | 3',4'-OCH$_2$O— | 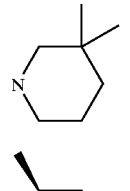 |

TABLE 7-continued

| Example No. | X | O | Z |
|---|---|---|---|
| No. 120 | OH | 4'-O-iPr |  |
| No. 121 | OH | 4'-O-iPr |  |
| No. 122 | OH | 4'-O-Cp |  |
| No. 123 | OH | 4'-CF₃ |  |
| No. 124 | OH | 4'-CH₃ |  |
| No. 125 | OH | 4'-Cl |  |
| No. 126 | OH | 2',4',-Dimethoxy |  |
| No. 127 | OH | 3'-OH |  |
| No. 128 | OH | 3'-OH |  |
| No. 129 | OH | 4'-OH,3'-F |  |

TABLE 7-continued

| Example No. | X | O | Z |
|---|---|---|---|
| No. 130 | OH | 4'-OH,3'-F |  |
| No. 131 | OH | 3'-OMe | |
| No. 132 | OH | 4'-OCF₃ | |

Hydrogenation of Indoles Containing Benzyl Ether(s)

Method 7

Illustrated for Example No. 97

2-(4-Hydroxy-phenyl)-3-methyl-1-[4-(2-piperidin-1-yl-ethoxy)-benzyl]-1H-indol-5-ol A suspension of 10% Pd/C (1.1 g) in EtOH was treated with a solution of No. 63 (2.2 g, 3.4 mmol) in THF/EtOH. Cyclohexadiene (6.0 mL, 63 mmol) was added and the reaction was stirred for 48 hours. The catalyst was filtered through Celite and the reaction mixture was concentrated and chromatographed on silica gel using a gradient elution of MeOH/CH$_2$Cl$_2$ (1:19 to 1:0) to yield 0.8 g of the product as a white solid. Mp=109–113° C.; CHN calc'd for C$_{29}$H$_{32}$N$_2$O$_3$+0.5H$_2$O; $^1$H NMR 9.64 (s, 1H), 8.67 (s, 1H), 7.14 (d, 2H, J=8.6 Hz), 7.05 (d, 1H, J=8.6 Hz), 6.84 (d, 2H, J=8.8 Hz), 6.79 (d, 1H, J=2.2 Hz), 6.74 (s, 4H), 6.56 (dd, 1H, J=8.8, 2.4 Hz), 5.09 (s, 2H), 3.95–3.93 (m, 2H), 2.60–2.51 (m, 2H), 2.39–2.38 (m, 4H), 2.09 (s, 3H), 1.46–1.45 (m, 4H), 1.35–1.34 (m, 2H); IR (KBr) 3350 (br), 2920, 1620, 1510 cm−1; MS (EI) m/z 456.

Alternatively, the compounds may be dissolved in a THF/EtOH solution (or other appropriate solvent) and hydrogenated with H$_2$ and 10% Pd/C using either a balloon or Parr Hydrogenator. Either procedure is effective. In many of the examples, the compounds were made into acid addition salts. The procedure for the preparation of an HCl salt is given below (Method 8).

Method 8

1.0 g of Example No. 97 free base from the hydrogenation procedure above in a large test tube was dissolved in 20 nL of MeOH. This was treated with slow addition of 2.6 mL 1.0 N HCl and then 4.0 mL deionized water. The tube was partially opened to the atmosphere to encourage slow evaporation of the solvents. After about ten minutes, crystals began to appear and after 4 hours the solution was filtered and the solid crystals washed with water. The product was present as 0.42 g of white crystalline plates with a melting point of 184–185° C. The mother liquor yielded an additional crop of 0.30 g of white solid with a melting point of 177–182° C. CHN calc'd for $C_{29}H_{32}N_2O_3+HCL+1H_2O$.

Alternatively, the compounds can be made into quaternary ammonium salts. An example procedure for the synthesis of example No. 107 is given below (Method 9).

Method 9

EXAMPLE NO. 107

2-(4-Hyrdroxy-phenyl)-3-methyl-1-[4-(2-piperidin-1-yl-ethoxy)-benzyl]-1H-indol-5-ol methiodide 0.8 g of example No. 97 was dissolved in 18 mL THF and treated with 2 mL of methyl iodide. The solution was heated to reflux for an hour. The reaction was allowed to come to room temperature and the solids filtered to yield 0.72 g as a crystalline solid. Mp=214–217° C., CHN calcd for $C_{29}H_{32}N_2O_3+CH_3I+0.5H_2O$.

EXAMPLE NO. 106

2-(4-Hydroxy-phenyl)-3-methyl-1-[4-(2-dimethyl-1-yl-ethoxy)-benzyl]-1H-indol-5-ol methiodide was prepared similarly to No. 106 except using No. 100 for starting material: Mp=245–250° C.; $^1$H NMR (DMSO) 9.66 (s, 1H), 8.69 (s, 1H), 7.16 (d, 2H, J=8.4 Hz), 7.05 (d, 1H, J=8.8 Hz), 6.84 (d, 1H, J=8.6 Hz), 6.81–6.75 (m, 6H), 6.56 (dd, 1H, J=2.4 Hz, 8.7 Hz), 5.12 (s, 2H), 4.34 (m, 2H), 3.70 (t, 2H, J=4.6 Hz), 3.11 (s, 9H), 2.09 (s, 3H); IR (KBr) 3250, 1500, 1250; MS eI m/z 416 (M+); CHN calcd for $C_{26}H_{28}N_2O_3+1.09CH_3I+0.8H_2O$.

Physical Data for Final, Deprotected Compounds

The following compounds are either free bases, HCl salts or acetate salts. They were prepared according to the procedure outlined in method 7 using the appropriate benzyl ether for precursor. Where a compound from table 1 does not contain a free phenolic functionality, then it was unnecessary to debenzylate it and method 7 not applied. The physical data for these compounds (No. 85, No. 90–No. 91) is still presented below.

EXAMPLE NO. 85

4-{3-Methyl-1-[4-(2-piperidin-1-yl-ethoxy)-benzyl]-1H-indole} (HCl)

MP=134–137° C.; $^1$H NMR (DMSO) 10.33 (s, 1H), 7.56–7.38 (m, 6H), 7.32 (d, 1H, J=8.1 Hz), 7.14–7.0 (m, 2H), 6.80 (s, 4H), 5.24 (s, 2H), 4.28 (t, 2H, J=5.0 Hz), 3.50–3.40 (m, 4H), 3.0–2.95 (m, 2H), 2.10 (s, 3H), 1.80–1.60 (m, 5H), 1.40–1.35 (m, 1H); IR 3400, 2900, 1510, 1250 cm$^{-1}$; MS (+) FAB m/z 425 [M+H]$^+$; CHN calcd for $C_{29}H_{32}N_2O+1.0HCl+1.0H_2O$.

EXAMPLE NO. 86

4-{3-Methyl-1-[4-(2-piperidin-1-yl-ethoxy)-benzyl]-1H-indol-2-yl}-phenol hydrochloride (HCl)

Mp=192–194° C.; 1H NMR (DMSO), 10.28 (s, 1H), 9.75 (s, 1H), 7.51–7.49 (m, 1H), 7.27 (dd, 1H, J=7.0 Hz, 0.7 Hz), 7.18 (d, 2H, J=7.6 Hz), 7.09–7.02 (m, 2H), 6.86 (d, 2H, J=8.6 Hz), 6.80 (s, 4H), 5.20 (s, 2H), 4.28 (t, 2H, J=4.9 Hz), 3.50–3.35 (m, 4H), 3.0–2.85 (m, 2H), 2.20 (s, 3H), 1.80–1.60 (m, 5H), 1.40–1.30 (m, 1H); IR 3400, 3100, 2600, 1500, 1225 cm$^{-1}$; MS eI m/z 440 (M+); CHN calc for $C_{29}H_{32}N_2O+1HCl$.

EXAMPLE NO. 87

3-Methyl-2-phenyl-1-[4-(2-piperidin-1-yl-ethoxy)-benzyl]-1H-indol-5-ol (HCl)

MP=228–230° C.; $^1$H NMR 10.1 (brs, 1H), 8.76 (s, 1H), 7.55–7.45 (m, 5H), 7.10 (d, 1H, J=8.8 Hz), 6.85–6.80 (m, 5H), 6.61 (d, 1H, J=8.8 Hz), 5.15 (s, 2H), 4.25 (t, 2H, J=4.8 Hz), 3.47–3.35 (m, 4H), 2.96–2.87 (m, 2H), 2.12 (s, 3H), 1.75–1.65 (m, 5H), 1.31–1.28 (m, 1H); MS eI m/z 440 (M+); CHN calcd for $C_{29}H_{32}N_2O_2+1HCL+0.33H_2O$; IR (KBr) 3200, 2500, 1450, 1200 cm$^{-1}$.

EXAMPLE NO. 88

4-{5-Methoxy-3-methyl-1-{4-[2-(piperidin-yl)-ethoxy]-benzyl}-1H-indol-2-yl}-phenol Mpt=87–90° C.; $^1$H NMR (DMSO) 9.67 (s, 1H), 7.16 (d, 2H, J=8.6 Hz), 7.16 (1H buried), 6.98 (d, 1H, J=2.4 Hz), 6.85 (d, 2H, J=8.6 Hz), 6.73 (s, 4H), 6.69 (dd, 1H, J=8.8, 2.4 Hz), 5.13 (s, 2H), 3.94 (t, 2H, J=5.7 Hz), 3.76 (s, 3H), 2.63–2.50 (m, 2H), 2.43–2.31 (m, 4H), 2.15 (s, 3H), 1.49–1.40 (m, 4H), 1.39–1.25 (m, 2H); IR (KBr) 3400 (br), 2920, 1610, 1520 cm$^{-1}$; MS eI m/z 470; CHN calcd for $C_{30}H_{34}N_2O_3+0.1H_2O$.

EXAMPLE NO. 89

2-(4-methoxy-phenyl)-3-methyl-1-{4-[2(piperidin-1-yl)-ethoxy]-benzyl}-1H-indol-5-ol Mp=188–189° C.; $^1$H NMR (DMSO) 8.70 (s, 1H), 7.27 (d, 2H, J=8.6 Hz), 7.06 (d, 1H, J=8.6 Hz), 7.02 (d, 2H, J=8.8 Hz), 6.81 (d, 1H, J=2.2 Hz), 6.73 (s, 4H), 6.58 (dd, 1H, J=8.8, 2.4 Hz), 5.10 (s, 2H), 3.93 (t, 2H, J=5.9 Hz), 3.79 (s, 3H), 2.56 (m, 2H, J=5.9 Hz), 2.41–2.32 (m, 4H), 2.10 (s, 3H), 1.47–1.41 (m, 4H), 1.34–1.31 (m, 2H); MS eI m/z 470; CHN calcd for $C_{30}H_{34}N_2O_3+0.1H_2O$.

EXAMPLE NO. 90

5-Methoxy-2-(4-methoxy-phenyl)-3-methyl-1-[4-(2-piperidin-1-yl-ethoxy)-benzyl]-1H-indole (HCL)

Mp=188–191° C.; $^1$H NMR (DMSO) 10.35 (brs, 1H), 7.27 (d, 2H, J=8.8 Hz), 7.17 (d, 1H, J=8.8 Hz), 7.03 (d, 2H, J=8.6 Hz), 6.99 (d, 1H, J=2.5 Hz), 6.82–6.78 (m, 4H), 6.71 (dd, 1H, J=8.8 Hz, J=2.5 Hz), 5.17 (s, 2H), 4.31–4.22 (m, 2H), 3.79 (s, 3H), 3.76 (s, 3H), 3.43–3.36 (m, 4H), 2.97–2.83 (m, 2H), 2.16 (s, 3H), 1.80–1.59 (m, 5H), 1.41–1.26 (m, 1H); IR (KBr) 2920, 1450, 1250 cm-1; MS eI m/z 484 (M+); CHN calc for $C_{31}H_{36}N_2O_3$+1HCL.

EXAMPLE NO. 91

1-[4-(2Azepan-1-yl-ethoxy)-benzyl-5-methoxy-2-(4-methoxy-phenyl)-3-methyl-1H-indole (HCL)

Mp=161–163° C.; $^1$H NMR (DMSO) 10.65 (brs, 1H), 7.27 (d, 2H, J=8.8 Hz), 7.17 (d, 1H, J=8.8 Hz), 7.03 (d, 2H, J=8.6 Hz), 6.99 (d, 1H, J=2.5 Hz), 6.82–6.77 (m, 4H), 6.71 (dd, 1H, J=8.8 Hz, J=2.5 Hz), 5.17 (s, 2H), 4.27 (m, 2H), 3.79 (s, 3H), 3.76 (s, 3H), 3.44–3.30 (m, 4H), 3.17 (m, 2H), 2.16 (s, 3H), 1.82–1.77 (m, 4H), 1.63–1.48 (m, 4H); MS eI m/z 499 (M+); CHN calc for $C_{32}H_{38}N_2O_3$+1HCl.

EXAMPLE NO. 92

2-(4-Ethoxy-phenyl]-3-methyl-1-[4-(2-piperidin-1-yl-ethoxy)-benzyl]-1H-indol-5-ol Mp=173–175° C.; $^1$H NMR (DMSO) 8.69 (s, 1H), 7.25 (d, 2H, J=8.8 Hz), 7.04 (d, 1H, J=8.8 Hz), 6.99 (dd, 2H, J=6.8 Hz, J=2.0 Hz), 6.80 (d, 1H, J=2.2 Hz), 6.73 (s, 4H), 6.59 (dd, 1H, J=8.5 J=2.2), 5.09 (s, 2H), 4.05 (q, 2H, J=7.03 Hz), 3.93 (t, 2H, J=6.0 Hz), 2.62–2.56 (m, 2H), 2.41–2.36 (m, 4H), 2.09 (s, 3H), 1.45–1.41 (m, 4H), 1.38–1.30 (m, 5H); MS eI m/z 484 (M+); CHN calc for $C_{31}H_{36}N_2O_3$+ 0.25$H_2O$.

EXAMPLE NO. 93

1-[4-(2-Azepan-1-yl-ethoxy)-benzyl]-2-(4-ethoxy-phenyl-3-methyl-1H-indol-5-ol

Mp=133–135° C.; $^1$H NMR (DMSO) 8.69 (s, 1H), 7.25 (d, 2H, J=8.8 Hz), 7.04 (d, 1H, J=8.8 Hz), 6.99 (dd, 2H, J=6.8 Hz, J=2.0 Hz), 6.80 (d, 1H, J=2.2 Hz), 6.73 (s, 4H), 6.59 (dd, 1H, J=8.5 Hz, J=2.2 Hz), 5.09 (s, 2H), 4.05 (q, 2H, J=7.03 Hz), 3.90 (t, 2H, J=6.1 Hz), 2.75 (t, 2H, J=6.0 Hz), 2.62–2.58 (m, 4H), 2.09 (s, 3H), 1.58–1.44 (m, 8H), 1.33 (t, 3H, J=7.0 Hz); IR (KBr) 2930, 1470, 1250 cm$^{-1}$; MS eI m/z 498 (M+); CHN calc for $C_{32}H_{38}N_2O_3$.

EXAMPLE NO. 94

4-{5-Fluoro-3-methyl-1-[4-(2-piperidin-1-yl-ethoxy)-benzyl]-1H-indol-2-yl}-phenol (HCl)

Mp=223–225° C.; $^1$H NMR (DMSO) 10.30 (brs, 1H), 7.27–713 (m, 2H), 7.17 (d, 2H, J=8.6 Hz), 6.88–6.79 (m, 7H), 5.20 (s, 2H), 4.28 (t, 2H, J=5.0 Hz), 3.42–3.35 (m, 4H), 3.00–2.85 (m, 2H), 2.14 (s, 3H), 1.78–1.70 (m, 4H), 1.67–1.59 (m, 1H), 1.40–1.26 (m, 1H); MS eI m/z 458 (M+).

EXAMPLE NO. 95

1-[4-(2-Azepan-1-yl-ethoxy)-benzyl]-3-methyl-2-phenyl-1H-indol5-ol (HCl)

Mp=203–204° C.; $^1$H NMR (DMSO) 10.50 (brs, 1H), 8.80 (s, 1H), 7.50–7.38 (m, 5H); 7.10 (d, 1H, J=8.8 Hz), 6.83–6.77 (m, 5H), 6.60 (d, 1H, J=6.6 Hz), 5.15 (s, 2H), 4.26 (t, 2H, J=5.2 Hz), 3.45–3.35 (m, 4H), 3.21–3.10 (m, 2H), 2.12 (s, 3H), 1.85–1.75 (m, 4H), 1.70–1.51 (m, 4H); MS eI m/z 454 (M+); CHN calc for $C_{30}H_{34}N_2O_2$+1HCl.

EXAMPLE NO. 96

2-(4-Hydroxy-phenyl)-3-methyl-1-[4-(2-pyrollidin-1-yl-ethoxy)-benzyl]-1H-indol-5-ol Mp=105–110° C.; CHN calc'd for $C_{28}H_{30}N_2O_3$+0.4$H_2O$; $^1$H NMR (DMSO) 9.65 (s, 1H), 8.67 (s, 1H), 7.15 (d, 2H, J=8.6 Hz), 7.05 (d, 1H, J=8.6 Hz), 6.84 (d, 2H, J=2H), 6.79 (d, 1H, J=2.4 Hz), 6.56 (dd, 1H, J=8.6, 2.2 Hz), 6.74 (s, 4H), 5.09 (s, 2H), 3.95 (t, 2H, J=5.7 Hz), 3.39–3.23 (m, 4H), 2.80–2.75 (nm, 2H), 2.09 (s, 3H), 1.67–1.64 (m, 4H); IR (KBr) 3410 (br), 1620, 1510 cm$^{-1}$; MS (EI) m/z 442.

EXAMPLE NO. 98

1-[4-(2-Azepan-1-yl-ethoxy)-benzyl]-2-(4-hydroxy-phenyl)-3-methyl-1H-indol-5-ol (HCl)

Mp=168–171° C.; $^1$H NMR (DMSO) 10.11 (br s, 1H), 9.70 (s, 1H), 8.71 (s, 1H); 7.15 (d, 2H, J=8.6 Hz), 7.05 (d, 1H, J=8.8 Hz), 6.85 (d, 2H, J=8.8 Hz), 6.80–6.77 (m, 5H), 6.56 (dd, 1H, J=8.8 Hz, 2.2 Hz), 5.11 (s, 2H), 4.26 (t, 2H, J=4.6 Hz), 3.43–3.30 (m, 4H), 3.22–3.08 (m, 2H), 2.09 (s, 3H), 1.83–1.76 (m, 4H), 1.67–1.48 (m, 4H); IR (KBr) 3500 br, 3250 br, 2900, 1610; MS FAB m/z 471 (M+H+); CHN calcd for $C_{30}H_{34}N_2O_3$+2.5$H_2O$+HCl.

EXAMPLE NO. 98

Acetate Salt

Made by the precipitation of No. 98 free base from acetone and acetic acid. Mp=174–178° C.

EXAMPLE NO. 99

1-[4-(2-Azepan-1-yl-ethoxy)-benzyl]-2-(4-hydroxy-phenyl)-3-methyl-1H-indol-5-ol

Mp=98–102° C.; $^1$H NMR (DMSO) 9.63 (s, 1H), 8.68 (s, 1H), 7.15–7.13 (m, 2H), 7.05 (d, 1H, J=8.5 Hz), 6.83 (dd, 2H, J=2.0 Hz, 6.6 Hz), 6.79 (d, 1H, J=2.2 Hz), 6.73 (s, 4H), 6.55 (dd, 1H, J=2.2 Hz, 8.6 Hz), 5.08 (s, 2H), 3.89 (t, 2H, J=5.7 Hz), 2.74 (t, 2H, J=5.4 Hz), 2.55 (bs, 4H), 2.08 (s, 3H), 1.55 (s, 2H), 1.46 (s, 8H); IR 3400, 2900, 1250 cm$^{-1}$; MS eI m/z 484 (M+); CHN calcd for $C_{31}H_{36}N_2O_3$+0.30$H_2O$.

EXAMPLE NO. 100

2-(4-Hydroxy-phenyl)-3-methyl-1-[4-(2-dimethyl-1-yl-ethoxy)-benzyl]-1H-indol-5-ol Mp=95–105° C.; IR (KBr) 3400 br, 2900, 1610 cm$^{-1}$; MS eI m/z 416 (M+); CHN calcd for $C_{26}H_{23N2}O_3$+0.5$H_2O$.

EXAMPLE NO. 101

2-(4-Hydroxy-phenyl)-3-methyl-1-[4-(2-diethyl-1-yl-ethoxy)-benzyl]-1H-indol-5-ol Mp=100–107° C.; CHN calc'd for $C_{28}H_{32}N_2O_3$+ 0.25$H_2O$; $^1$H NMR (DMSO) 9.64 (s, 1H), 8.67 (s, 1H), 7.14 (d, 2H, J=8.6 Hz), 7.05 (d, 1H, J=8.8 Hz), 6.84 (d, 2H, J=8.6 Hz), 6.79 (d, 1H, 2.2 Hz), 6.74 (s, 4H), 6.56 (dd, 1H, J=8.8, 2.4 Hz), 5.09 (s, 2H), 3.95–3.85 (m, 2H), 2.80–2.60 (m, 2H), 2.58–2.40 (m, 4H), 2.09 (s, 3H), 0.93 (t, 6H, J=7.0 Hz); IR (KBr) 3410 (br), 2950, 1610, 1510 cm$^{-1}$; MS FAB 445 (M+H+).

EXAMPLE NO. 102

1-[4-(2-Dipropylamino-ethoxy)-benzyl]-2-(4-hydroxy-phenyl)-3-methyl-1H-indol-5-ol Mp=83–86° C.; $^1$H NMR (DMSO) 9.64 (s, 1H), 8.67 (s, 1H), 7.14 (d, 2H, J=8.6), 7.04 (d, 1H, J=8.6 Hz), 6.83 (d, 2H, J=8.6 Hz), 6.78 (d, 1H, J=2.2 Hz), 6.72 (m, 4H), 6.55 (dd, 1H, J=2.4 Hz, 8.2 Hz), 5.08 (s, 2H), 3.88 (t, 2H, J=6.0 Hz), 2.80–2.63 (m, 2H), 2.59–2.45 (m, 4H), 2.10 (s, 3H), 1.41–1.30 (m, 4H), 0.79 (t, 6H, J=7.3 Hz); IR 3400, 2900, 1250; MS FAB m/z 473 [M+H+]; CHN calcd for $C_{30}H_{36}N_2O_3+0.20H_2O$.

EXAMPLE NO. 103

1-[4-(2-Dibutylamino-ethoxy)-benzyl]-2-(4-hydroxy-2-phenyl)-3-methyl-1H-indol-5-ol Foam; $^1$H NMR (DMSO) 9.63 (s, 1H), 8.66 (s, 1H), 7.15 (d, 2H, J=8.6 Hz), 7.05 (d, 1H, J=8.8 Hz), 6.83 (d, 2H, J=8.6 Hz), 6.79 (d, 1H, J=4.2 Hz), 6.78–6.71 (m, 4H), 6.55 (dd, 1H, J=8.6 Hz J=2.4 Hz), 5.10 (s, 2H), 3.88 (t, 2H, J=5.5 Hz), 2.68–2.62 (m, 2H), 2.42–2.34 (m, 4H), 2.08 (s, 3H), 1.38–1.19 (m, 8H), 0.82 (t, 6H, J=7.2 Hz); IR (KBr) 3400, 1450 cm$^{-1}$; MS eI m/z 501 (M+).

EXAMPLE NO. 104

1-[4-(2-Diisopropylamino-ethoxy)-benzyl]-2-(4-hydroxy-phenyl)-3-methyl-1H-indol-5-ol Mp=96–102° C.; $^1$H NMR (DMSO) 9.64 (s, 1H), 8.67 (s, 1H), 7.14 (d, 2H, J=8.6 Hz), 7.04 (d, 1H, J=8.6 Hz), 6.83 (d, 2H, J=8.6 Hz), 6.79 (d, 1H, J=2.4 Hz), 6.77–6.69 (m, 4H), 6.56 (dd, 1H, J=8.6 Hz, 2.2 Hz), 508 (s, 2H), 3.75 (t, 2H, J=7.0 Hz), 3.01–2.92 (m, 2H), 2.67 (t, 2H; J=7.0 Hz), 2.09 (s, 3H), 0.93 (d, 12H, 6.6 Hz); IR (KBr) 3400 br, 2940, 1620 cm$^{-1}$; MS FAB m/z 473 (M+H+); CHN calcd for $C_{30}H_{36}N_2O_3+0.5H_2O$.

EXAMPLE NO. 105

1-{4-[2-(Butyl-methyl-amino)-ethoxy]-benzyl}-2-(4-hydroxy-phenyl)-3-methyl-1H-indol-5-ol Mp=102–107° C.; $^1$H NMR (DMSO) 9.60 (s, 1H), 8.67 (s, 1H), 7.14 (d, 2H, J=8.4 Hz), 7.04 (d, 1H, J=8.6 Hz), 6.82 (d, 2H, J=8.8 Hz), 6.78 (d, 1H, J=2.3 Hz), 6.73 (s, 4H), 6.55 (dd, 1H, J=8.8 Hz, J=2.4 Hz), 5.08 (s, 2H), 3.92 (t, 2H, J=6.0 Hz), 2.64–2.59 (m, 2H), 2.38–2.29 (m, 2H), 2.20 (br s, 3H), 2.08 (s, 3H), 1.40–1.31 (m, 2H), 1.25–1.19 (m, 2H), 0.83 (t, 3H, 7.2 Hz); IR 3420, 1460, 1230 cm$^{-1}$; MS eI m/z 638 (M+).

EXAMPLE NO. 108

2-(4-Hydroxy-phenyl)-3-methyl-1-{4-[2-(2-methyl-piperidin-1-yl)-ethoxy]-benzyl}-1H-indol-5-ol Mp=121–123° C.; $^1$H NMR (DMSO) 9.65 (s, 1H), 8.68 (s, 1H), 7.14 (d, 2H, J=8.6 Hz), 7.04 (d, 1H, J=8.8 Hz), 6.84 (d, 2H, J=8.6 Hz), 6.79 (d, 1H, J=2.0 Hz), 6.74 (s, 4H), 6.56 (dd, 1H, J=8.8 Hz, 2.4 Hz), 5.09 (s, 2H), 3.97–3.86 (m, 2H), 2.95–2.73 (m, 2H), 2.62–2.53 (m, 1H), 2.36–2.14 (m, 2H), 2.09 (s, 3H), 1.61–1.30 (m, 4H), 1.28–1.09 (m, 2H), 0.98 (d, 3H, J=5.1 Hz); IR (KBr) 3400, 2920, 2850, 1610 cm$^{-1}$; CHN calcd for $C_{30\ H34}N_2O_3+0.25H_2O$.

EXAMPLE NO. 109

2-(4-Hydroxy-phenyl)-3-methyl-1-{4-[2-(3-methyl-piperidin-1-yl)-ethoxy]-benzyl}-1H-indol-5-ol Mp=121–123° C.; $^1$H NMR (DMSO) 9.64 (s, 1H), 8.67 (s, 1H), 7.14 (dd, 2H, J=8.3 Hz, 1.4 Hz), 7.04 (dd, 1H, J=8.6 Hz, 1.2 Hz), 6.84 (dd, 2H, J=8.6 Hz, 1.7 Hz), 6.79 (s, 1H), 6.79 (s, 4H), 6.56 (d, 1H, J=8.6 Hz), 5.08 (s, 2H), 3.94 (t, 2H, J=5.0 Hz), 2.86–2.71 (m, 2H), 2.63–2.50 (m, 2H), 2.48 (s, 3H), 1.92–1.79 (m, 2H), 1.63–1.35 (m, 5H), 0.79 (d, 3H, J=5.2 Hz); IR (KBr) 3400, 2910, 1625 cm$^{-1}$; CHN calcd for $C_{30}H_{34}N_2O_3+0.25H_2O$.

EXAMPLE NO. 110

2-(4-Hydroxy-phenyl)-3-methyl-1-{4-[2-(4-methyl-piperidin-1-yl)-ethoxy]-benzyl}-1H-indol-5-ol (HCl)

Mp=154–162° C.; $^1$H NMR (DMSO) 10.00 (brs, 1H), 9.71 (s, 1H), 8.71 (s, 1H), 7.15 (d, 2H, J=8.6 Hz), 7.05 (d, 1H, J=8.6 Hz), 6.85 (d, 2H, J=8.6 Hz), 6.83–6.77 (m, 4H), 6.57 (dd, 1H, J=8.6 Hz, 2.2 Hz), 5.11 (s, 2H), 4.27 (t, 2H, J=4.8 Hz), 3.51–3.35 (m, 4H), 3.01–2.87 (m, 2H), 2.09 (s, 3H), 1.74 (d, 2H, J=13.4 Hz), 1.61–1.37 (m, 4H), 0.88 (d, 3H, J=6.4 Hz); IR (KBr) 3410, 2910, 1620 cm$^{-1}$; MS eI m/z 470 (M+H+); CHN calcd for $C_{30}H_{34}N_2O_3+HCl+2H_2O$.

EXAMPLE NO. 111

1-{4-[2-(3,3-Dimethyl-piperidin-1-yl)-ethoxy]-benzyl}-2-(4-hydroxy-phenyl)-3-methyl-1H-indol-5-ol Mp=100° C.; $^1$H NMR (DMSO) 9.65 (s, 1H), 8.67 (s, 1H), 7.15 (d, 2H, J=8.6 Hz), 7.05 (d, 1H, J=8.8 Hz), 6.84 (d, 2H, J=8.6 Hz), 6.79 (d, 1H, J=2.4 Hz), 6.74 (s, 4H), 6.56 (dd, 1H, J=8.8, 2.4 Hz), 5.09 (s, 2H), 3.93 (t, 2H, J=5.7 Hz), 2.60–2.50 (m, 2H), 2.37–2.25 (m, 2H), 2.09 (s, 3H), 210–1.99 (m, 2H), 1.46 (, 2H, J=5.9 Hz), 1.13 (t, 2H, J=6.4 Hz), 0.86 (s, 6H); MS eI m/z 484.

EXAMPLE NO. 112

1-{4-[2-((cis)-2,6-Dimethyl-piperidin-1-yl)-ethoxy]-benzyl}-2-(4-hydroxy-phenyl)-3-methyl-1H-indol-5-ol Mp=114–121° C.; $^1$H NMR (DMSO) 9.62 (s, 1H), 8.64 (s, 1H), 7.11 (d, 2H, J=8.6 Hz), 7.01 (d, 1H, J=8.6 Hz), 6.81 (d, 2H, J=8.8 Hz), 6.76 (d, 1H, J=2.2 Hz), 6.72–6.66 (m, 4H), 6.53 (dd, 1H, J=8.6 Hz, 2.2 Hz), 5.06 (s, 2H), 3.86–3.72 (m, 2H), 2.86–2.76 (m, 2H), 2.43–2.35 (m, 2H), 2.06 (s, 3H), 1.78–1.59 (m, 3H), 1.29–1.17 (m, 1H), 1.12–0.92 (m, 8H); IR (KBr) 3400 br, 2920, 1630 cm-1; MS FAB m/z 485 (M+H+); CHN calcd for CHN, cald for $C_{31}H_{36}N_2O_3+0.1$ acetone+$0.75H_2O$.

EXAMPLE NO. 113

2-(4-Hydroxy-phenyl)-1-{4-[2-(4-hydroxy-piperidin-1-yl)-ethoxy]-benzyl}-3-methyl-1H-indol-5-ol Mp=80–90° C.; $^1$H NMR (DMSO) 9.66 (s, 1H), 8.68 (s, 1H), 7.15 (d, 2H, J=7.6 Hz), 7.04 (d, 1H, J=8.8 Hz), 6.84 (dd, 2H, J=2.0 Hz, 6.6 Hz), 6.78 (d, 1H, 2.2 Hz), 6.73 (s, 4H), 6.55 (dd, 1H, J=2.2 Hz, 8.6 Hz), 5.09 (s, 2H), 4.50 (d, 1H, J=4.2 Hz), 3.92 (t, 2H, J=5.8 Hz), 3.40 (m, 2H), 2.72 (m, 2H), 2.60 (m, 2H), 2.10 (s, 3H), 2.15–2.05 (m, 1H), 1.75–1.63 (m, 2H), 1.42–1.28 (m, 2H); IR (KBr) 3400, 2900, 1250 cm$^{-1}$; MS eI m/z 472 (M+); CHN calcd for $C_{29}H_{32}N_2O_4$+0.11$CH_2Cl_2$.

EXAMPLE NO. 114

(1S,4R)-1-{4-[2-(2-Aza-bicyclo[2,2,1]hept-2-yl)-ethoxy]-benzyl}-2-(4-hydroxy-phenyl)-3-methyl-1H-indnol-5-ol Mp=125–130° C.; $^1$H NMR (DMSO) 9.65 (s, 1H), 8.67 (s, 1H), 7.13 (d, 2H, J=8.6 Hz), 7.04 (d, 1H, J=8.5 Hz), 6.83 (dd, 2H, J=2.0 Hz, 6.6 Hz), 6.78 (d, 1H, J=2.2 Hz), 6.73 (s, 4H), 6.55 (dd, 1H, J=2.2 Hz, 8.6 Hz), 5.08 (s, 2H), 3.95–3.8 (m, 2H), 2.90–2.70 (3H), 2.30–2.20 (m, 2H), 2.10 (s, 3H), 1.70–1.60 (m, 1H), 1.60–1.30 (m, 4H), 1.25–1.15 (m, 2H); IR (KBr) 3400, 2950, 1500; MS (+) FAB m/z 469 [N+H]$^+$; CHN calcd for $C_{30}H_{32}N_2O_3$+0.34EtOAc.

EXAMPLE NO. 115

2-(4-Hydroxy-phenyl)-3-methyl-1-{4-[2-(1,3,3-trimethyl-6-aza-bicyclo[3,2,1]oct-6-yl)-ethoxy]-benzyl}-1H-indol-5-ol Mp=98–100° C.; $^1$H NMR (DMSO) 9.64 (s, 1H), 8.67 (s, 1H), 7.14 (d, 2H, J=8.6 Hz), 7.05 (d, 1H, J=8.6 Hz), 6.84 (d, 2H, J=8.6 Hz), 6.79 (d, 1H, J=2.4 Hz), 6.75–6.69 (m, 4H), 6.56 (dd, 1H, J=8.6 Hz, 2.4 Hz), 5.08 (s, 2H), 3.83 (t, 2H, J=5.9 Hz), 3.12–3.07 (m, 1H), 2.94–2.87 (m, 1H), 2.85 (d, 1H, J=9.2 Hz), 2.78–2.70 (m, 1H), 2.17 (d, 1H, J=9.2 Hz), 2.09 (s, 3H), 1.55–1.42 (m, 2H), 1.29 (q, 2H, J=13.6 Hz), 1.14 (s, 3H), 1.11–1.02 (m, 2H), 0.96 (s, 3H), 0.82 (s, 3H); IR (KBr) 3400 br, 2940, 2900, 1630 cm$^{-1}$; MS ESI m/z 525 (M+H+); CHN calcd for $C_{34}H_{40}N_2O_3$+0.5$H_2O$.

EXAMPLE NO. 116

2-(4-Fluoro-phenyl)-3-methyl-1-[4-(2-piperidin-1-yl-ethoxy)-benzyl]-1H-indol-5-ol (HCl)

Mp 201–203° C.; $^1$H NMR (DMSO) 10.22 (s, 1H), 8.78 (s, 1H), 7.45–7.35 (m, 2H), 7.34–7.25 (m, 2H), 7.11 (d, 1H, J=8.6 Hz), 6.90–6.70 (m, 5H), 6.61 (dd, 1H, J=2.4 Hz, 8.8 Hz), 5.15 (s, 2H), 4.27 (t, 2H, 4.8 Hz), 3.50–3.34 (m, 4H), 3.0–2.85 (m, 2H), 2.10 (s, 3H), 1.80 (m, 5H), 1.40–1.25 (m, 1H); MS eI m/z 458 (M+); CHN calcd for $C_{29}H_{31}FN_2O_2$+1HCl.

EXAMPLE NO. 117

1-[4-(2-Azepan-1-yl-ethoxy)-benzyl]-2-(4-fluoro-phenyl)-3-methyl-1H-indol-5-ol

Mp=181–184° C.; $^1$H NMR (DMSO) 10.68 (s, 1H), 8.80 (s, 1H), 7.50–7.36 (m, 2H), 7.34–7.26 (m, 2H), 7.12 (d, 1H, J=8.8 Hz), 6.86–6.73 (m, 5H), 6.63 (dd, 1H, J=2.2 Hz, 8.5 Hz), 5.13 (s, 2H), 4.29 (t, 2H, J=5.2 Hz), 3.50–3.30 (m, 4H), 3.20–3.08 (m, 2H), 2.11 (s, 3H), 1.90–1.70 (m, 4H), 1.68–1.45 (m, 4H); IR (KBr) 3500, 3100, 2910, 1450, 1250 cm$^{-1}$; MS e/I m/z 472 (M+); CHN calcd for $C_{30}H_{33}FN_2O_2$+1HCl.

EXAMPLE NO. 118

2-(3-Methoxy-4-hydroxy-phenyl)-3-methyl-1-[4-(2-piperidin-1-yl-ethoxy)-benzyl]-1H-indol-5-ol (HCl)

Mp=161–163° C.; $^1$H NMR (DMSO) 10.12 (brs, 1H), 9.25 (s, 1H), 8.71 (s, 1H), 7.05 (d, 1H, J=8.5 Hz), 6.85–6.79 (m, 8H), 6.57 (dd, 1H, J=8.5 Hz, J=2.2 Hz), 5.13 (s, 2H), 4.27 (t, 2H, J=5.0 Hz), 3.64 (s, 3H), 3.44–3.37 (m, 4H), 2.93–2.85 (m, 2H), 2.11 (s, 3H), 1.80–1.60 (m, 5H), 1.40–1.25 (m, 1H); MS eI m/z 486 (M+); CHN calc for $C_{30}H_{34}N2O_4$+1HCL+1$H_2O$; IR (KBr) 3190, 1470, 1230 cm$^{-1}$.

EXAMPLE NO. 119

2-Benzyl[1,3]dioxol-5-yl-3-methyl-1-[4-(2-piperidin-1-yl-ethoxy)benzyl]-1H-indol-5-ol (HCL)

Mp=122–125° C.; $^1$H NMR (DMSO) 9.80 (brs, 1H), 8.73 (s, 1H), 7.07 (d, 1H, J=8.7 Hz), 7.02 (d, 1H, J=8.0 Hz), 6.89 (d, 1H, J=1.7 Hz), 6.80–6.75 (m, 6H), 6.58 (dd, 1H, J=6.4 Hz, J=2.2 Hz), 6.06 (s, 2H), 5.13 (s, 2H), 4.30–4.19 (m, 2H), 3.51–3.30 (m, 4H), 2.99–2.85 (m, 2H), 2.10 (s, 3H), 1.81–1.59 (m, 5H), 1.41–1.26 (m, 1H); MS eI m/z 484 (M); CHN calc for $C_{30}H_{32}N_2O_4$+HCl+0.26$H_2O$.

EXAMPLE NO. 120

2-(4-Isopropoxy-phenyl)-3-methyl-1-[4-(2-piperidin-1-yl-ethoxy)-benzyl]-1H-indol-5-ol (HCl)

Mp=120–125° C.; $^1$H NMR (DMSO) 10.18 (s, 1H), 8:73 (s, 1H), 7.25 (d, 2H, J=8.6 Hz), 7.04 (d, 1H, J=8.8 Hz), 6.99 (d, 2H, J=8.8 Hz), 6.82–6.80 (m, 5H), 6.59 (dd, 1H, J=2.2 Hz, 8.6 Hz), 5.12 (s, 2H), 4.67–4.61 (m, 1H), 4.27 (t, 2H, J=4.8 Hz), 3.50–3.35 (m, 4H), 3.0–2.85 (m, 2H), 2.10 (s, 3H), 1.80–1.60 (m, 5H), 1.40–1.25 (m, 7H); IR (KBr) 3400, 3000, 1500, 1250; MS eI m/z 498 (M+); CHN calcd for $C_{32}H_{38}N_2O_3$+1.0HCl+0.70$H_2O$.

EXAMPLE NO. 121

1-[4-(2-Azepan-1-yl-ethoxy)-benzyl]-2-(4-isopropoxy-phenyl)-3-methyl-1H-indol-5-ol (HCl)

Mp=120–125° C.; $^1$H NMR (DMSO) 10.36 (s, 1H), 8.73 (s, 1H), 7.6–7.23 (m, 2H), 7.05 (d, 1H, J=8.8 Hz), 7.01–6.98 (m, 2H), 6.85–6.75 (m, 5H), 6.57 (dd, 1H, J=2.2 Hz, 8.6 Hz), 5.12 (s, 2H), 4.67–4.61 (m, 1H), 4.27 (t, 2H, J=4.8 Hz), 3.50–3.30 (m, 4H), 3.20–3.10 (m, 2H), 2.10 (s, 3H), 1.85–1.75 (m, 4H), 1.65–1.50 (m, 4H), 1.27 (d, 6H, J=6.1 Hz); IR (KBr) 3400, 1500, 1250: MS eI m/z 512 (M+); Calcd for $C_{33}H_{40}N_2O_3$+1.0HCl+0.5$H_2O$.

EXAMPLE NO. 122

2-(4-Cyclopenyloxy-phenyl)-3-methyl-1-[4-(2-piperidin-1-yl-ethoxy)-benzyl]-1H-indol-5-ol Mp=121–135° C.; $^1$H NMR (DMSO) 9.80 (br s, 1H), 8.72 (s, 1H), 7.24 (d, 2H, J=8.8 Hz), 7.05 (d, 1H, J=8.8 Hz), 6.98 (d, 2H, J=8.8 Hz), 6.83–6.78 (m, 5H), 6.57 (dd, 1H, J=8.8 Hz, 2.4 Hz), 5.13 (s, 2H), 4.86–4.82 (m, 1H), 4.25 (t, 2H, J=4.8 Hz), 3.50–3.38 (m, 4H), 2.92 (q, 2H, J=8.8 Hz), 2.11 (s, 3H), 1.98–1.85 (m, 2H), 1.81–1.56 (m, 11H), 1.41–1.29 (m, 1H); IR (KBr) 3400, 2920, 1620 cm$^{-1}$; MS eI m/z 524 (M+); CHN calcd for $C_{34}H_{40}N_2O_3$+0.5$H_2O$.

EXAMPLE NO. 123

3-Methyl-1-[4-(2-piperidin-1-yl-ethoxy)-benzyl]-2-(4-trifluoromethyl-phenyl)-1H-indol-5-ol Mp=174° C.; $^1$H NMR (DMSO) 8.8 (s, 1H), 7.82 (d, 2H, J=8.1 Hz), 7.59 (d, 2H, J=7.9 Hz), 7.17 (d, 1H, J=8.6 Hz), 6.86 (d, 1H, J=2.4 Hz), 6.75–6.68 (m, 4H), 6.65 (dd, 1H, J=8.8 Hz, 2.4 Hz), 5.16 (s, 2H), 3.93 (t 2H, J=5.7 Hz), 2.62–2.56 (m, 2H), 2.42–2.32 (m, 4H), 2.15 (s, 3H), 1.48–1.40 (m, 4H), 1.39–1.29 (m, 2H); IR (KBr) 3410, 2910, 2850, 1620 cm$^{-1}$; MS eI m/z 508 (M+); CHN calcd for $C_{30}H_{31}F_3N_2O_2$+0.25$H_2O$.

EXAMPLE NO. 124

3-Methyl-1-[4-(2-piperidin-1-yl-ethoxy)-benzyl]-2-p-tolyl-1H-indol-5-ol

Mp=162–164° C.; $^1$H NMR (DMSO) 8.70 (s, 1H), 7.28–7.24 (m, 4H), 7.07 (d, 1H, J=8.4 Hz), 6.81 (d, 1H, J=2.2 Hz), 6.73 (s, 4H), 6.58 (dd, 1H, J=2.4 Hz, 8.8 Hz), 5.11 (s, 2H), 3.92 (t, 2H, J=5.9 Hz), 2.55 (t, 2H, J=5.9 Hz), 2.45–2.30 (m, 7H), 2.10 (s, 3H), 1.50–1.40 (m, 4H), 1.48–1.35 (m, 2H); IR (KBr) 3400, 2900, 1200; MS eI m/z 454 (M+); CHN calcd for $C_{30}H_{34}N_2O_2$.

EXAMPLE NO. 125

2-(4-Chloro-phenyl)-3-methyl-1-[4-(2-piperidin-1-yl-ethoxy)-benzyl]-1H-indol-5-ol (HCL)

Mp=161–164° C.; $^1$H NMR (DMSO) 10.12 (brs, 1H), 8.80 (s, 1H), 7.53 (d, 2H, J=8.3 Hz), 7.36 (d, 2H, J=8.8 Hz), 7.12 (d, 1H, J=8.8 Hz), 6.85–6.75 (m, 5H), 6.63 (dd, 1H, J=8.8 Hz, J=2.4 Hz), 5.14 (s, 2H), 4.29–4.22 (m, 2H), 3.45–3.36 (m, 4H), 2.97–2.84 (m, 2H), 2.11 (s, 3H), 1.83–1.61 (m, 5H), 1.37–1.25 (m, 1H); MS eI m/z 475 (M+); CHN calc for $C_{39}H_{31}ClN_2O_2$+HCL+0.25$H_2O$.

EXAMPLE NO. 126

2-(2,4-Dimethoxy-phenyl)-3-methyl-1-[4-(2-piperidin-1-yl-ethoxy)-benzyl]-1H-indol-5-ol Mp=85–92° C.; $^1$H NMR (DMSO) 8.62 (s, 1H), 7.10 (d, 1H, J=8.4 Hz), 7.01 (d, 1H, J=8.6 Hz), 6.80–6.70 (m, 5H), 6.69 (d, 1H, 2.2 Hz), 6.59 (dd, 1H, J=2.4 Hz, 8.5 Hz), 6.52 (dd, 1H, J=2.4 Hz, 8.8 Hz), 5.02 (d, 1H, J=6.5 Hz), 4.83 (d, 1H, J=6.3 Hz), 4.0–3.90 (m, 2H), 3.80 (s, 3H), 3.67 (s, 3H), 2.65–2.50 (m, 2H), 2.45–2.30 (m, 4H), 2.0 (s, 3H), 1.55–1.40 (m, 4H), 1.39–1.30 (m, 2H); IR (KBr) 3400, 2900, 1520, 1250; MS eI m/z 500 (M+); CHN calcd for $C_{31}H_{36}N_2O_4$+0.05$CH_2Cl_2$.

EXAMPLE NO. 127

2-(3-Hydroxy-phenyl)-3-methyl-1-[4-(2-piperidin-1-yl-ethoxy)-benzyl]-1H-indol-5-ol Mp=115–118° C.; $^1$H NMR (DMSO) 9.57 (s, 1H), 8.71 (s, 1H), 7.27–7.23 (t, 1H, J=8.1 Hz), 7.06–7.04 (d, 1H, J=8.8 Hz), 6.81–6.74 (m, 8H), 659–6.56 (dd, 1H, J=2.3 Hz, J=6.3 Hz), 5.12 (s, 2H), 3.94–3.91 (t, 2H, J=5.9 Hz), 2.57–2.54 (t, 2H, J=5.8 Hz), 2.36 (s, 4H), 2.11 (s, 3H), 1.45–1.41 (m, 4H), 1.34–1.33 (m, 2H); IR (KBr) 3400, 2900 cm$^{-1}$; MS eI m/z 456 (M+); CHN calcd for $C_{29}H_{32}N_2O_3$+1.0$H_2O$.

EXAMPLE NO. 128

1-[4-(2-Azepan-1-yl-ethoxy)-benzyl]-2-(3-hydroxy-phenyl)-3-methyl-1H-indole-5-ol Mp=94–97° C.; $^1$H NMR (DMSO) 9.58 (s, 1H), 8.71 (s, 1H), 7.27–7.23 (t, 1H, J=7.9 Hz), 7.07–7.04 (d, 1H, J=8.7 Hz), 6.81–6.74 (m, 8H), 6.59–6.56 (dd, 1H, J=2.4 Hz, J=6.3 Hz), 5.12 (s, 2H), 3.9 (m, 2H), 2.80 (s, 2H), 2.65 (s, 4H), 2.11 (s, 3H), 1.54–1.50 (m, 8H); IR 3400, 2900 cm$^{-1}$; MS eI m/z 470 (M+); CHN calcd for $C_{30}H_{34}N_2O_3$+0.75$H_2O$+0.23 Ethyl Acetate.

EXAMPLE NO. 129

2-(3-Fluoro-4-hydroxyl-phenyl)-3-methyl-1-[4-(2-piperidin-1-yl-ethoxy)-benzyl]-1H-indol-5-ol Mp=117–119° C.; $^1$H NMR (DMSO) 10.1 (s, 1H), 8.71 (s, 1H), 7.10–6.95 (m, 4H), 6.80 (d, 1H, J=2.2 Hz), 6.74 (s, 4H), 6.59 (dd, 1H, J=2.2 Hz, 8.5 Hz), 5.1 (s, 2H), 3.93 (t, 2H, J=5.9 Hz), 2.56 (t, 2H, J=5.8 Hz), 2.44–2.30 (m, 4H), 2.10 (s, 3H), 1.45–1.40 (m, 4H), 1.36–1.32 (m, 2H); MS eI m/z 475 (M+); CHN calcd for $C_{29}H_{31}FN_2O_3$.

EXAMPLE NO. 130

2-(3-Fluoro-4-hydroxy-phenyl)-3-methyl-1-[4-(azepan-1-yl-ethoxy)-benzyl]-1H-indol-5-ol Mp=88–91° C.; $^1$H NMR (DMSO) 10.10 (s, 1H), 8.71 (s, 1H), 7.12–6.94 (m, 4H), 6.80 (d, 1H, J=2.2 Hz), 6.74 (s, 4H), 6.58 (dd, 1H, J=2.2 Hz, 8.5 Hz), 5.10 (s, 2H), 3.91 (t, 2H, J=5.9 Hz), 2.76 (t, 2H, J=5.9), 2.62–2.60 (m, 4H), 2.10 (s, 3H), 1.70–1.40 (m, 8H); MS eI m/z 488 (M+); CHN calcd for $C_{30}H_{33}FN_2O_3$.

EXAMPLE NO. 131

2-(3-Methoxy-phenyl)-3-methyl-1-[4-(2-piperidin-1-yl-ethoxy)-benzyl]-1H-indole-5-ol Mp=120–123° C.; $^1$H NMR (DMSO) 8.76 (s, 1H), 7.42–7.46 (t, 1H, J=7.9 Hz), 7.12–7.09 (d, 1H, J=8.7 Hz), 6.99–6.92 (m, 2H), 6.86–6.83 (m, 2H), 6.76 (s, 4H), 6.63–6.60 (dd, 1H, J=2.1 Hz, J=6.5 Hz), 5.14 (s, 2H), 3.96–3.92 (t, 2H, J=5.9 Hz), 3.70 (s, 3H), 2.59–2.55 (t, 2H, J=5.9 Hz), 2.37 (s, 4H), 2.14 (s, 3H), 1.49–1.44 (m, 4H), 1.35–1.34 (m, 2H); IR 3400, 2950, 1600 cm$^{-1}$; MS eI m/z 471 (M+); CHN calcd for $C_{30}H_{34}N_2O_3$,

EXAMPLE NO. 132

3-Methyl-1-[4-(2-piperidin-1-yl-ethoxy)-benzyl]-2-(4-trifluoromethoxy-phenyl)-1H-indole-5-ol Mp=122–125° C.; $^1$H NMR (DMSO) 8.80 (s, 1H), 7.51–7.45 (m, 4H), 7.17–7.14 (d, 1H, J=8.7 Hz), 6.85–6.84 (d, 1H, J=2.0 Hz), 6.75–6.69 (m, 4H), 6.66–6.62 (m, 1H), 5.14 (s, 2H), 3.95–3.92 (t, 2H, J=5.8 Hz), 2.59–2.55 (t, 2H, J=5.6 Hz), 2.49–2.38 (m, 4H), 2.13 (s, 3H), 1.47–1.44 (m, 4H), 1.36–1.34 (d, 2H, J=4.8 Hz); IR 3400, 2900, 1600 cm$^{-1}$; MS eI m/z 525 (M+); CHN calcd for $C_{30}H_{31}F_3N_2O_3$+0.25$H_2O$.

Synthetic procedures and physical data for compounds substituted with chloro, ethyl or cyano groups at the 3-position of the indole

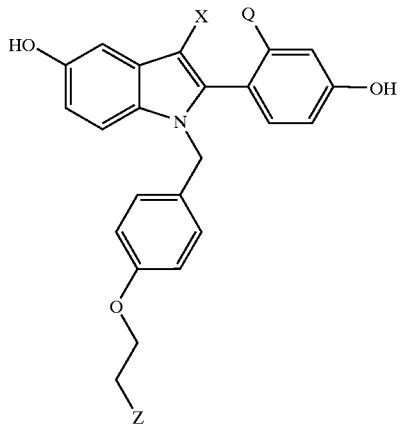

TABLE 8

| Example No. | X | Q | Z |
|---|---|---|---|
| No. 133 | Cl | H | pyrrolidine |
| No. 134 | Cl | H | piperidine |
| No. 135 | Cl | H | azepane |
| No. 136 | Cl | CH₃ | piperidine |
| No. 137 | Et | H | piperidine |
| No. 138 | CN | H | piperidine |
| No. 139 | CN | H | azepane |

Synthesis of 3-chloro Analogues No. 133–No. 136.

Scheme 14

Synthesis of 3-chloroindole

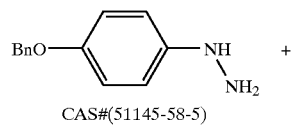
CAS#(51145-58-5)

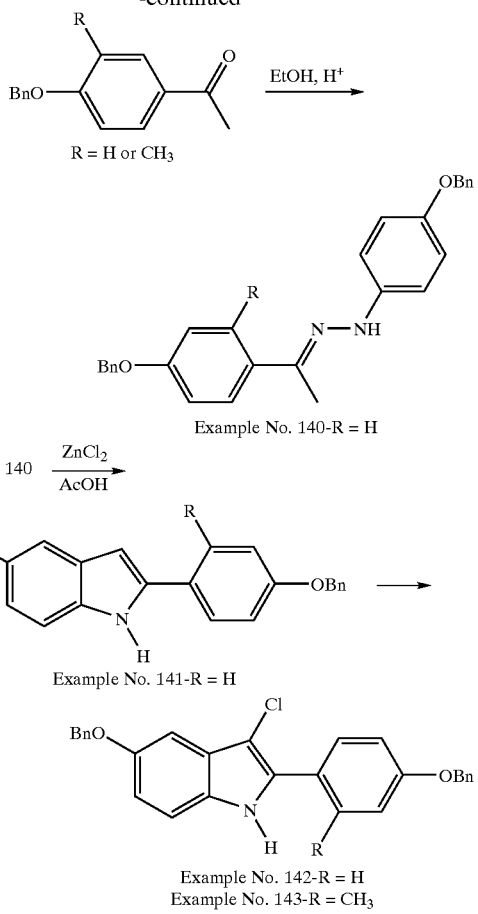

EXAMPLE NO. 140

Formation of Hydrazone

4-Benzyloxyphenylhydrazine CAS No. [51145-58-5] (50.0 g, 233.4 mmol) was mixed with 4-benzyloxyacetophenone CAS No. [54696-05-8] (63.0 g, 280.0 mmol) in pure ethanol (800 mL). A catalytic amount of acetic acid (5 drops) was added. The reaction was heated to reflux for 2.5 hrs. During the course of refluxing, the condensed product solidified out of the hot solution. The reaction was cooled down to rt. The desired product was collected by vacuum filtration as a light yellow solid (85 g, 86%). Mp=165–174° C.; $^1$H NMR (DMSO) 8.91 (s, 1H), 7.68 (d, 2H, J=8.8 Hz), 7.48–7.32 (m, 10H), 7.12 (d, 2H, J=9 Hz), 7.00 (d, 2H, J=8.8 Hz), 6.88 (d, 2H, J=9.0 Hz), 5.11 (s, 2H), 5.01 (s, 2H), 2.17 (s, 3H); MS eI m/z 422 (M+).

EXAMPLE NO. 141

Formation of Indole from Hydrazone: 5-Benzyloxy-2-(4-benzyloxy-phenyl)-1H-indole A flask was charged with N-(4Benzyloxy-phenyl)-N'-[1-(4-benzyloxy-phenyl)-ethylidene]-hydrazine (No. 140) (10.0 g, 23.7 mmol), ZnCl₂ (8.06 g, 59.17 mmol), acetic acid (70 mL). The reaction flask was heated to 105° C. for no more than 20 min. During the heating period, the reaction was monitored carefully by TLC for the disappearance of the starting material. The progress of the reaction could be shown as the product solidified out of the solution while heating. The reaction was then cooled to rt and more product crashed out was observed. The reaction content was poured into a separatory funnel containing ether (100 mL) and $H_2O$ (200 mL), which was shaken vigorously. The insoluble residue as the desired product stayed in the ether layer which was collected by vacuum filtration The product was further purified by triration in ether to give a light gray solid (4.4 g, 46%)

Mp=202–204° C.; $^1$H NMR (DMSO) 11.24 (s, 1H), 7.73 (d, 2H, J=8.8 Hz), 7.48–7.41 (m, 4H), 7.45–7.27 (m, 6H), 7.25 (d, 1H, J=8.6 Hz), 7.12–7.04 (m, 3H), 6.77 (dd, 1H, J=2.4 Hz, 8.6 Hz), 6.65 (d, 1H, J=1.5 Hz), 5.14 (s, 2H), 5.08 (s, 2H); IR 3420, 3000, 1625 cm$^{-1}$; MS eI m/z 405 (M+); CHN calcd for $C_{28}H_{23}NO_2+0.40H_2O$.

EXAMPLE NO. 142

Chlorination of Indole to Render 5-Benzyloxy-3-chloro-2-(4-benzyloxy-phenyl)-1H-indole A flask was charged with 5-Benzyloxy-2-(4-benzyloxy-phenyl)-1H-indole No. 141 (8.0 g, 20.0 mmole) and $CH_2Cl_2$ (50 ml). The reacton was cooled to 0° C. and n-chlorosuccinimide(2.9 g, 22 mmole) was added. The reaction was stirred at 0° C. for 20 min. The reaction was then washed with 10% sodium sulfite solution, dried over $MgSO_4$, and concentrated. To the resulting brown solid was added MeOH and the mixture was stirred for 15 min. The solid was filtered to give 6.8 g of a tan solid (78%). Mp=157–160° C.; $^1$H NMR (DMSO) 11.5 (s, 1H), 7.80 (d, 2H, J=7.0 Hz), 7.42–7.28 (m, 11H), 7.17 (d, 2H, J=8.7 Hz), 7.01 (d, 1H, J=2.2 Hz), 6.88 (dd 1H, J=8.8 Hz, J=2.4 Hz), 5.17 (s, 2H), 5.13 (s, 2H); MS eI m/z 439 (M+).

EXAMPLE NO. 143

5-Benzyloxy-3-chloro-2-(2-methyl-4-benzyloxy-phenyl)-1H-indole

This indole synthesized analogously to indole No. 142 immediately preceding: Mp=$^1$H NMR (DMSO) 11:34 (s, 1H), 7.48–7.44 (m, 4H), 7.42–7.24 (m, 8H), 7.02 (dd, 2H, J=9.3 Hz, J=2.4 Hz), 6.95(dd, 1H, J=8.4 Hz, J=2.6 Hz), 6.88 (dd, 1H, J=8.8 Hz, J=2.4 Hz), 5.16 (s, 2H), 5.14 (s, 2H), 2.23 (s, 3H); MS eI m/z 453 (M+).

EXAMPLE NO. 144

Alkylation of Indole to Give {4-[5-Benzyloxy-2-(4-benzyloxy-phenyl)-3-chloro-indol-1-ylmethyl]-phenoxyl}-asetic acid ethyl ester This procedure was performed analogously to that outlined for the synthesis of 3-methyl indole acetic acid ethyl esters outlined in method 3.

Mp=90–94° C.; $^1$H NMR (DMSO) 7.45 (d, 4H, J=7.8 Hz), 7.41–7.26 (m, 9H), 7.14 (d, 2H, J=8.7 Hz), 7.04 (d, 1H, J=2.4 Hz), 6.91 (dd, 1H, J=9.0 Hz, J=2.5 Hz), 6.80–6.74 (m, 4H), 5.24 (s, 2H), 5.15 (s, 2H), 5.14 (s, 2H), 4.66 (s, 2H), 4.12 (q, 2H, J=7.2 Hz), 1.16 (t, 3H, J=7.5 Hz); MS eI m/z 631 (M+).

EXAMPLE NO. 145

Reduction of No. 144 to Render No. 145 2-{4-[5-Benzyloxy-2-(4-benzyloxy-phenyl-3-chloro-indol-1-ylmethyl]-phenoxy}-ethanol This reaction was performed analogously to that outlined for the synthesis of 3-methyl indoles outlined in method 4. Compound was not purified or characterized, but used as obtained for the next step.

EXAMPLE NO. 146

Bromination of No. 145 to Render Benzyloxy-2-(4-benzyloxy-phenyl)-1-[4-(2-bromo-ethoxy)-benzyl]-3-chloro-1H-indole This reaction was performed analogously to that outlined for the synthesis of 3-methyl indoles outlined in method 5. Mp=155–158° C.; $^1$H NMR (DMSO) 7.45 (d, 4H, J=7.8 Hz), 7.41–7.25 (m, 9H), 7.14 (d, 2H, J=8.7 Hz), 7.04 (d, 1H, J=2.4 Hz); 6.91 (dd, 1H, J=9.0 Hz, J=2.5 Hz), 6.74 (s, 4H), 5.24 (s, 2H), 5.15 (s, 2H), 5.14 (s, 2H), 4.20 (t, 2H, J=5.3 Hz), 3.74 (t 2H, J=5.3 Hz); MS eI m/z 651 (M+).

EXAMPLE NO. 147

Substitution of No. 146 with Piperidin to Render 5-Benzyloxy-2-(4-benzyloxy-phenyl)3-chloro-1-[4-(2-piperidin-1-yl-ethoxy)-benzyl]-1H-indole This reaction performed analogously to that outlined for the synthesis of 3-methyl indoles outlined in method 6, using piperidin to substitute the bromide.

Mp 96–98° C.; $^1$H NMR (DMSO) 7.45 (d, 4H, J=7.8 Hz), 7.40–7.30 (m, 9H), 7.14 (d, 2H, J=8.7 Hz), 7.04 (d, 1H, J=2.4 Hz), 6.91(dd, 1H, J=9.0 Hz, J=2.5 Hz), 6.74 (s, 4H), 5.24 (s, 2H), 5.15 (s, 2H), 5.14 (s, 2H), 3.93 (t, 2H, J=6.0 Hz), 2.56 (t, 2H, J=6.0 Hz), 2.41–2.32 (m, 4H), 1.48–1.39 (m, 4H), 1.38–1.31 (m, 2H).

EXAMPLE NO. 148

5-Benzyloxy-2-(4-benzyloxy-phenyl)-3-chloro-1-[4-(2-azepan-1-yl-ethoxy)-benzyl]-1H-indole Reaction performed the same as above except the substituting amine used was hexamethyleneamine.

Mp=94–97° C.; $^1$H NMR (DMSO) 7.45 (d, 4H, J=7.8 Hz), 7.42–7.30 (m, 9H), 7.14 (d 2H, J=8.7 Hz), 7.04 (d, 1H, J=2.4 Hz), 6.91 (dd, 1H, J=9.0 Hz, J=2.5 Hz), 6.74 (s, 4H), 5.24 (s, 2H), 5.15 (s, 2H), 5.14 (s, 2H), 3.93 (t, 2H, J=6.0 Hz), 2.75 (t, 2H, J=6.0 Hz), 2.63–2.59 (m, 4H), 1.58–1.44 (m, 8H); MS eI m/z 671 (M+).

EXAMPLE NO. 149

5-Benzyloxy-2-(2-methyl-4-benzyloxy-phenyl)-3-chloro-1-[4-(2-piperidin-1-yl-ethoxy)-benzyl]-1H-indole Reactions to make this compound analogous to those used to make No. 147. Oil; $^1$H NMR (DMSO) 7.50–7.29 (m, 11H), 7.17 (d, 1H, J=8.4 Hz), 7.05 (d, 1H, J=2.4 Hz), 7.02 (d, 1H, J=2.4 Hz), 6.93–6.85 (m, 2H), 6.75–6.65 (m, 4H), 5.14 (s, 2H), 5.13 (s, 2H), 5.07 (m, 2H), 3.92 (t, 2H, J=5.9 Hz), 2.55 (t, 2H, J=5.9 Hz), 2.42–2.29 (m, 4H), 1.94 (s, 3H), 1.44–1.40 (m, 4H), 1.38–1.34 (m, 2H).

EXAMPLE NO. 133

3-Chloro-2-(4-hydroxy-phenyl)-1-[4-(2-pyrrolidin-1-yl-ethoxy)-benzyl]-1H-indol-5-ol (Hcl)

Synthesized as described for example No. 134.

Mp=233–235° C.; $^1$H NMR (DMSO) 10.50 (s, 1H), 9.88 (s, 1H), 9.01 (s, 1H), 7.30–7.20 (m, 3H), 6.90–6.80 (m, 7H), 6.68 (dd, 1H, J=2.4 Hz, 8.8 Hz), 5.20 (s, 2H), 4.22 (t, 2H, J=4.8 Hz), 3.47 (t, 2H, J=4.8 Hz), 3.10 (m, 4H), 1.90 (s, 4H); IR (KBr) 3400, 1625, 1475, 825 cm$^{-1}$; MS eI m/z 462 (M+); CHN calcd for $C_{27}H_{27}ClN_2O_3$+1HCl+0.75$H_2O$.

EXAMPLE NO. 134

Removal or Benzyl Ethers to Render 3-Chloro-2-(4-hydroxy-phenyl)-1-[4-(2-piperidin-1-yl-ethoxy)-benzyl]-1H-inldol-5-ol (HCl)

Benzyl ethers were removed analogously to that procedure outlined for 3-methyl indoles outlined in method 7. This compound was then converted to the hydrochloride salt as described previously in method 8; Mp=207–209° C.; $^1$H NMR (DMSO) 10.10 (bs, 1H), 9.86 (s, 1H), 9.07 (s, 1H), 7.26 (d, 2H, J=8.6 Hz), 7.22 (d, 1H, J=8.8 Hz), 6.87 (d, 2H, J=8.6 Hz), 6.81–6.78 (m, 5H), 6.65 (dd, 1H, J=8.8 Hz, J=2.2 Hz), 5.20 (s, 2H), 4.27 (t, 2H, J=5.0 Hz), 3.44–3.37 (m, 4H), 3.00–2.85 (m, 2H), 1.81–1.60 (m, 5H), 1.41–1.26 (m, 1H); IR (KBr) 3350, 1470, 1250 cm−1; MS eI m/z 476 (M+); CHN calc for $C_{28}H_{29}ClN_2O_3$+HCL+1.5$H_2O$.

EXAMPLE NO. 135

3-Chloro-2-(4-hydroxy-phenyl)-1-[4-(2-azepan-1-yl-ethoxy)-benzyl]-1H-indol-5-ol (Hcl)

Synthesized as described for No. 134.

Mp=196–198° C.; $^1$H NMR (DMSO) 10.10(brs, 1H), 9.86 (s, 1H), 9.07 (s, 1H), 7.26 (d, 2H, J=8.8 Hz), 7.22 (d, 1H, J=9.0 Hz), 6.87 (d, 2H, J=8.6 Hz), 6.84–6.78 (m, 5H), 6.65 (dd, 1H, J=8.8 Hz, J=2.2 Hz), 5.20 (s, 2H), 4.27 (t, 2H, J=5.0 Hz), 3.45–3.30 (m, 4H), 3.21–3.10 (m, 2H), 1.82–1.76 (m, 4H), 1.65–1.46 (m, 4H); MS eI m/z 491 (M+); CHN calc for $C_{29}H_{31}ClN_2O_3$+1HCl+0.37$H_2O$; IR (KBr) 3400, 3200, 1450, 1125

EXAMPLE NO. 136

3-Chloro-2-(4-hydroxy-2-methyl-phenyl)-1-[4-(2-piperidin-1-yl-ethoxy)-benzyl]-1H-indol-5-ol Synthesized as described for No. 134 except the compound was not converted into a salt.

Foam; $^1$H NMR (DMSO) 9.64 (s, 1H), 9.01 (s, 1H), 7.25 (d, 1H, J=8.8 Hz), 7.03 (d, 1H, J=8.1 Hz), 6.79 (d, 1H, J=2.4 Hz), 6.78–6.65 (m, 7H), 5.06–4.92 (m, 2H), 3.94 (t, 2H, J=5.9 Hz), 2.62–2.57 (m, 2H), 2.42–2.32 (m, 4H), 1.90 (s, 3H), 1.48–1.40 (m, 4H) 1.40–1.32 (m, 2H); MS eI m/z 490 (M+); IR (KBr) 3430, 2900, 1450 cm$^{-1}$; CHN calc for $C_{29}H_{31}ClN_2O_3$+1.0$H_2O$.

Synthesis of 3-ethylindole Analogue No. 137

This compound was synthesized in exact analogy to the example given for 3-methylindoles, supra, using methods a and 2–8. The only difference is that the starting material used is 4-(benzyloxy)-Butyrophenone CAS No. [26945-71-1] instead of 4'-(benzyloxy)-Propiophenone. Data for intermediates is as follows.

EXAMPLE NO. 150

5-Benzyloxy-2-(4-benzyloxy-2-phenyl)-3-ethyl-1H-indole

Mp=101–108° C.; MS eI m/z 433 (M+).

EXAMPLE NO. 151

{4-[5-Benzyloxy-2-(4-benzyloxy-phenyl)-3-ethyl-indnol-1-ylmethyl]-phenoxy}-acetic acid ethyl ester Mp=72–75° C.; MS eI m/z 625 (M+).

EXAMPLE NO. 152

2-{4-[5-Benzyloxy-2-(4-benzyloxy-phenyl)-3-ethyl-indol-1-ylmethyl]-phenoxy}-ethanol Mp=105–113° C.; MS eI m/z 583 (M+).

EXAMPLE NO. 153

Benzyloxy-7-(4-benzyloxy-phenyl)-1-[4-(2-bromo-ethoxy)-benzyl]-3-ethyl-1H-indole Mp=140° C. (decomp.); MS eI m/z 647, 645 (M+, Br present).

EXAMPLE NO. 154

5-Benzyloxy-2-(4-benzyloxy-phenyl)-3-ethyl-1-[4-(2-piperidin-1-yl-ethoxy)-benzyl]-1H-indole Mp=92–96° C.; $^1$H NMR (DMSO) 7.47 (d, 4H, J=7.2 Hz), 7.42–7.39 (m, 4H), 7.36–7.30 (m, 2H), 7.27 (d, 2H, J=8.6 Hz), 7.18 (d, 1H, J=8.8 Hz), 7.14 (d, 1H, J=2.4 Hz), 7.10 (d, 2H, J=8.8 Hz), 6.79 (dd, 1H, J=8.8 Hz, 2.2 Hz), 6.73 (s, 4H), 5.13 (s, 2H), 5.11 (s, 4H), 3.93 (t, 2H, J=5.9 Hz), 2.62–2.53 (m, 4H), 2.40–2.33 (m, 4H), 1.49–1.42 (m, 4H), 1.37–1.30 (m, 2H), 1.10 (t, 3H, J=7.2 Hz); MS eI m/z 650 (M+H+).

EXAMPLE NO. 137

2-(4-Hydroxy-phenyl)-3-ethyl-1-[4-(2-piperidin-1-yl-ethoxy)-benzyl]-1H-indol-5-ol (HCl)

Mp=160–164° C.; $^1$H NMR (DMSO) 9.78 (br s, 1H), 9.69 (s, 1H), 8.69 (s, 1H), 7.14 (d, 2H, J=8.6 Hz), 7.05 (d, 1H, J=8.6 Hz), 6.87–6.78 (m, 7H), 6.56 (dd, 1H, J=8.8 Hz, 2.4 Hz), 5.08 (s, 2H), 4.25 (t, 2H, J=4.4 Hz), 3.45–3.38 (m, 5H), 3.00–2.86 (m, 2H), 2.57–2.50 (m, 2H), 1.83–1.59 (m, 5H), 1.41–1.28 (m, 1H), 1.10 (t, 2H, J=7.5 Hz); IR (KBr) 3400 br, 3200 br, 2920, 1610 cm$^{-1}$; MS eI m/z 470 (M+); CHN calcd for $C_{30}H_{34}N_2O_3$+HCl+1.5$H_2O$.

Scheme 15

Synthesis of 3-cyanoindole Analogues

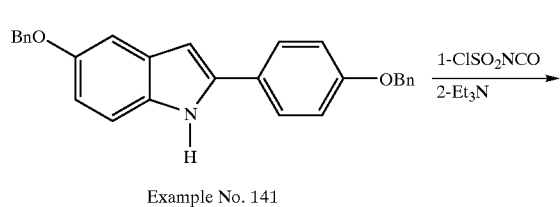

Example No. 141

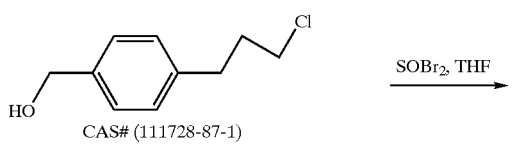

CAS# (111728-87-1)

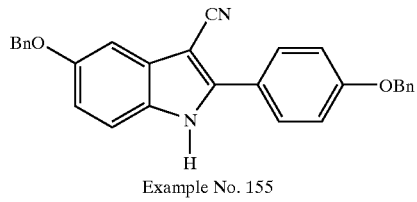

Example No. 155

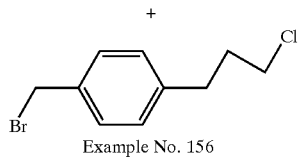

Example No. 156

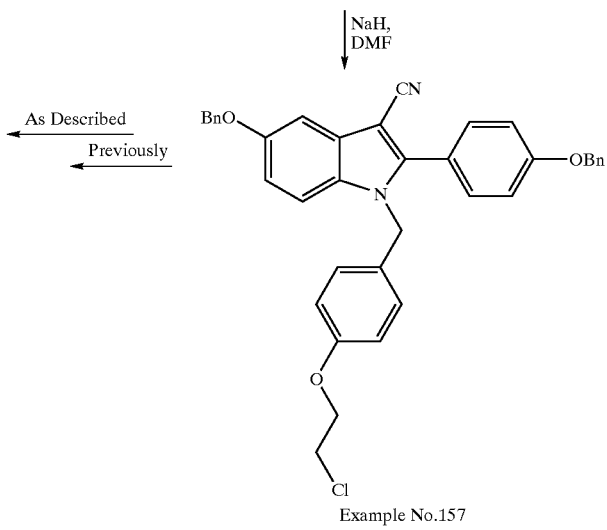

Example No.157

EXAMPLE NO. 155

5-Benzyloxy-3-cyano-2-(4-benzyloxy-phenyl)-1H-indole

In a reaction flask 5-Benzyloxy-2-(4-benzyloxy-phenyl)-1H-indole No. 141 (5.90 g, 14.6 mmol) was mixed with $CH_2Cl_2$ (90 mL) was cooled down to 0° C. (the starting material did not completely dissolve in $CH_2Cl_2$). While stirring vigorously, a solution of chlorosulfonyl isocyanate (2.26 g, 16.0 mmol) in $CH_2Cl_2$ (25 mL) was added dropwise over a period of 45 min. The reaction was run at 0° C. for 2 hrs while detected by TLC for the formation of the insoluble N-chlorosulfonylamide intermediate. After this period, $Et_3N$ (1.47 g, 14.6 mL) in $CH_2Cl_2$ (25 mL) was added dropwise over 45 min at 0° C. The insoluble residue became soluble in the reaction solvent as the $Et_3N$ addition was approaching completion. The reaction was let go for the additional 1 hr at 0° C. and 2 hrs at rt. The progress of the reaction could be observed by the insoluble solid formation of the product as the reaction time went on. The solvent was stripped down and the solid residue purified by trituration with methanol to yield (4.0 g, 63.8%). Mp=238–242° C.; $^1$H NMR (DMSO) 12.31 (s, 1H), 7.88 (d, 2H, J=8.8 Hz), 7.48 (d, 4H, J=7.25 Hz), 7.55–7.30 (m, 7H), 7.23 (d, 2H, J=8.8 Hz), 7.14 (d, 1H, J=2.4 Hz), 6.97 (dd, 1H, J=2.2 Hz, 8.8 Hz), 5.20 (s, 2H), 5.17 (s, 2H); MS eI m/z 430 (M+).

EXAMPLE NO. 156

4-(2-Chloroethoxy)benzylbromide

To 4-(2-Chloroethoxy)benzytalcohol CAS No. [111728-87-1] (6.4 g, 34.31 mmol) in dioxane (100 mL) at 0° C. was added slowly thionylbromide (7.13 g, 34.31 mmol). The reaction was run at 0° C. after 5 min. The reaction mixture was diluted with ether (200 mL) and washed with $H_2O$ (1×30 mL) then $NaHCO_3$ (2×25 mL), and brine (30 mL). The organic extract was dried over $MgSO_4$ and concentrated. The crude product was purified by silica gel chromatography (15% EtOAc/Hex) to yield 5.0 g (58%) of the desired product Mp=64–66° C.; $^1$H NMR (DMSO) 7.37 (d, 2H, J=8.8 Hz), 6.93 (d, 2H, J=8.8 Hz), 4.68 (s, 2H), 4.24 (t, 2H, J=5.05 Hz), 3.93 (t, 2H, J=5.27 Hz); MS eI m/z 248 (M+).

EXAMPLE NO. 157

Benzyloxy-2-(4-benzyloxy-phenyl)-1-[4-(2-chloroethoxy)-benzyl]-3-cyano-1H-indole In a reaction flask the 3-cyano indole starting material No. 155 (2.86 g, 6.64 mmol) was dissolved in DMF (25 mL) at 0° C. was added NaH (191.2 mg, 8 mmol) slowly. The reaction was stirred at 0° C. for 20 min. In a separate reaction flask containing (2-Chloroethoxy)benzylbromide No. 156 (1.81 g, 7.28 mmol) in DMF (15 mL) at 0° C., the above prepared indole anion solution taken up by syringe was added slowly. The reaction was stirred at 0° C. for 20 min and promoted to rt for 1 h. The reaction was quenched with a few drops of $H_2O$. The reaction mixture was partitioned between EtOAc (2×100 mL) and $H_2O$ (80 mL). The organic extract was washed with brine (80 mL), dried over $MgSO_4$, and concentrated. The crude product was purified by trituration with ether to give the product as a white solid (2.80 g, 70.4%). Mp=160–162° C.; $^1$H NMR (DMSO) 7.53–7.28 (m, 13H), 7.23 (m, 3H), 6.97 (dd, 1H, J=2.4 Hz, 9.0 Hz), 6.86–6.78 (m, 4H), 5.37 (s, 2H), 5.18 (s, 4H), 4.15 (t, 2H, J=4.8 Hz), 3.87 (t, 2H, J=5.3 Hz); MS eI m/z 598 (M+).

EXAMPLE NO.'s 158 AND 159

Substitution of the chloro group with piperidin and hexamethyleneamine was performed analogously to the procedure outlined in method 6 using No. 157 as a starting material, supra.

EXAMPLE NO. 158

5-Benzyloxy-2-(4-benzyloxy-phenyl)-3-cyano-1-[4-(2-piperidin-1-yl-ethoxy)-benzyl]-1H-indole Mp=148–150° C.; $^1$H NMR (DMSO) 7.54–7.30 (m, 13H), 7.25–7.18 (m, 3H), 6.98 (dd, 1H, J=2.4 Hz, 9.0 Hz), 6.84–6.74 (m, 4H), 5.35 (s, 2H), 5.17 (s, 4H), 3.94 (t, 2H, 5.9 Hz), 2.55 (t, 2H, 5.7 Hz), 2.35 (bs, 4H), 1.50–1.40 (m, 4H), 1.38–1.25 (m, 2H); IR 3400, 2910, 2250, 1250 cm$^{-1}$; MS FAB 648 [M+H]+.

EXAMPLE NO. 159

5-Benzyloxy-2-benzyloxy-phenyl)-3-cyano-1-[4-(2-azepan-1-yl-ethoxy)-benzyl]-1H-indole $^1$H NMR (DMSO) 8.60 (br s, 1H), 7.60–7.28 (m, 12H), 7.25–7.16 (m, 3H), 6.97 (dd, 1H, J=2.4 Hz, 9.0 Hz), 6.88–6.75 (m, 4H), 5.35 (s, 2H), 5.17 (s, 4H), 3.92 (t, 2H, J=6.2 Hz), 308–3.00 (m, 2H), 2.77 (t, 2H, J=5.9 Hz), 2.63 (t, 4H, J=4.8 Hz), 1.78–1.68 (m, 2H), 1.60–1.40 (m, 4H); MS eI m/z 661 (M+).

EXAMPLE NO. 138 AND NO. 139

Benzyl ethers were removed by hydrogen transfer using 1,4 cyclohexadiene and 10% Pd/C as described in method 7. Compounds were convened into their respective hydrochloride salts as described in method 8.

EXAMPLE NO. 138

5-Hydroxy-2-(4-Hydroxy-phenyl)-1-[4-(2-piperidin-1-yl-ethoxy-benzyl]-1H-indole-3-carbonitrile (HCl)

Mp=173–175° C.; $^1$H NMR (DMSO) 10.40 (s, 1H), 10.12 (s, 1H), 9.40 (s, 1H), 7.38 (m, 2H), 7.30 (d, 1H, J=8.8 Hz), 7.02–6.90 (m, 3H), 6.88 (s, 4H), 6.75 (dd, 1H, J=2.4 Hz, 9 Hz), 5.33 (s, 2H), 4.30 (t, 2H, J=4.8 Hz), 3.51–3.38 (m, 4H), 2.92 (m, 2H), 1.85–1.73 (m, 4H), 1.68–1.59 (m, 1H), 1.26–1.21 (m, 1H); IR 3400, 2200, 1250 cm$^{-1}$; MS eI m/z 467 (M+), CHN calcd for $C_{29}H_{29}N_3O_3$+1.0HCl+1.0$H_2O$.

EXAMPLE NO. 139

1-[4-(2-Azepan-1-yl-ethoxy)-benzyl]-5-hydroxy-2-(4-hydroxy-phenyl)-1H-indole-3-carbonitrile (HCl)

Mp=160–163° C.; $^1$H NMR (DMSO) 10.22 (s, 1H), 10.08 (s, 1H), 9.35 (s, 1H), 7.40–7.37 (m, 2H), 7.30 (d, 1H, 8.8 Hz), 7.0–6.90 (m, 3H), 6.87 (s, 4H), 6.74 (dd, 1H, J=2.41 Hz, 9 Hz), 5.33 (s, 2H), 4.27 (t, 2H, J=5.0 Hz), 3.50–3.30 (m, 4H), 3.20 (m, 2H), 1.85–1.70 (m, 4H), 1.65–1.50 (m, 4H); IR 3300, 2200, 1250 cm$^{-1}$; MS eI m/z 481 (M+); CHN calc for $C_{30}H_{31}N_3O_3$+1HCl+1$H_2O$.

Esters of Indole No.'s 97 and 98

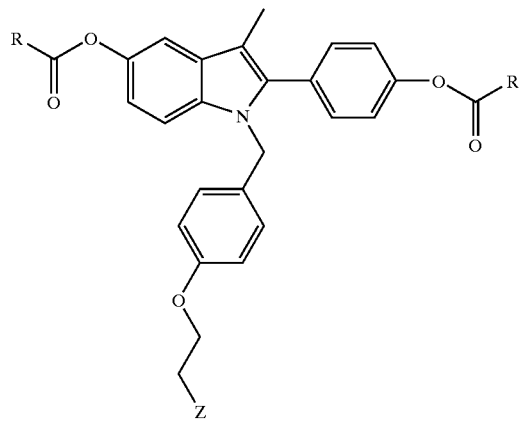

TABLE 9

| Example No. | R | Z |
|---|---|---|
| No. 160 | Et | azepane |
| No. 161 | t-Bu | azepane |
| No. 162 | t-Bu | piperidine |

Method 9

EXAMPLE NO. 162

Di-pivalate ester of 2-(4-Hydroxy-phenyl)-3-methyl-1-[4-(2-piperidin-1-yl-ethoxy)-benzyl]-1H-indol-5-ol Example No. 97 free base was used as the starting material for this synthesis. No. 97 (1.0 g, 2.5 mmol) in 20 mL $CH_2Cl_2$ was treated with diisopropylethylamine (0.7 g, 6.3 mmol) and cataltic DMAP. The reaction was cooled to 0° C. and treated with pivaloyl chloride (0.7 mL, 5.6 mmol) and allowed to come to rt and stirred overnight. The reaction was worked up by diluting with $CH_2Cl_2$ and washing with water and brine. After drying over $MgSO_4$ the solution was concentrated and chromatographed on silica gel (MeOH/$CH_2Cl_2$, 1:19) to yield the desired material as an orange foam (1.08 g). This material was then taken up in 15 mL ethyl acetate and treated with 2.5 mL of a 1 M HCl/Et$_2$O solution. Hexane was added until the solution turned cloudy. The product precipitated out as the HCl Salt. This material was recrystallized from ethyl acetate/hexane to yield 0.42 g of pure No. 162: Mp=182–185° C.; CHN calcd for C$_{39}$H$_{48}$N$_2$O$_5$+HCl+0.25H$_2$O.

EXAMPLE NO. 160

Di-propionate of 1-[4-(2-Azepan-1-yl-ethoxy)-benzyl]-2-(4-hydroxy-phenyl)-3-methyl-1H-indol-5-ol (HCl)

Compound was prepared analogously to example No. 162 except the starting material used was example No. 98 and the acylating agent used was propionyl chloride: Mp=170.5–172° C.; CHN calcd for C$_{36}$H$_{42}$N$_2$O$_5$+HCl+0.75H$_2$O; MS FAB 605 (M+Na)+.

EXAMPLE NO. 161

Di-pivalate of 1-[4-(2-Azepan-1-yl-ethoxy)-benzyl]-2-(4-hydroxy-phenyl)-3-methyl-1H-indol-5-ol (HCl)

Compound was prepared analogously to example No. 162 except the staring material used was example No. 98: Mp=143–151° C.; CHN calcd for C$_{40}$H$_{50}$N$_2$O$_5$+HCl+0.75H$_2$O.

Experimental for Example No. 166

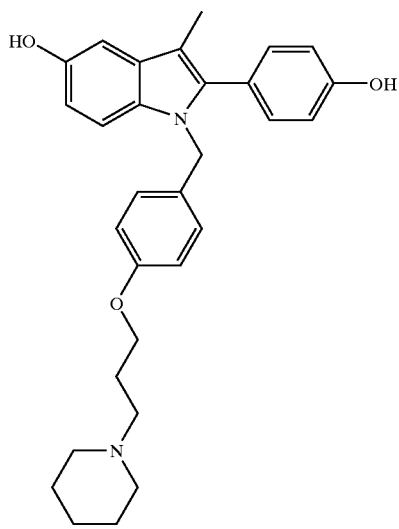

Scheme 16
Synthesis of No. 166

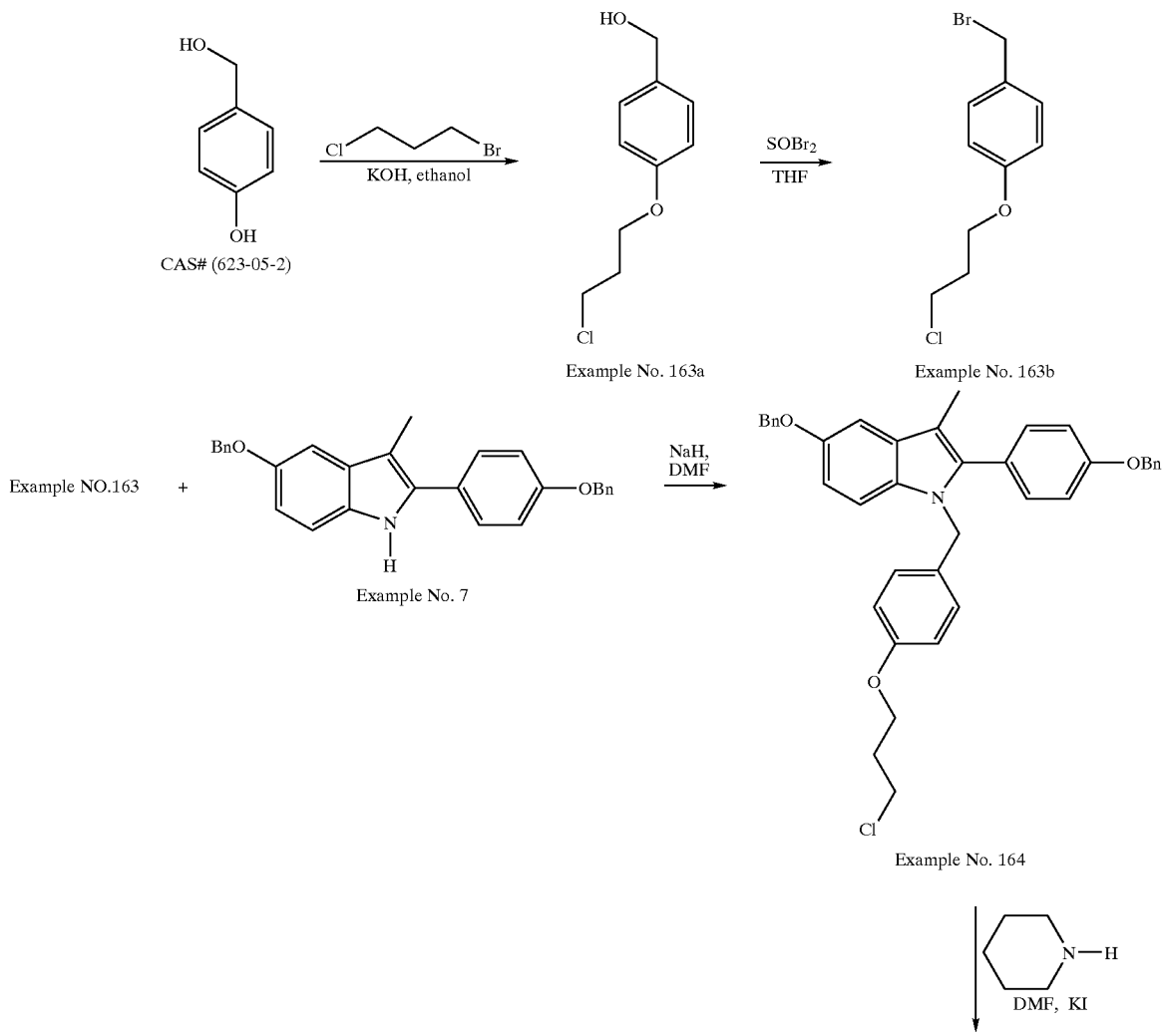

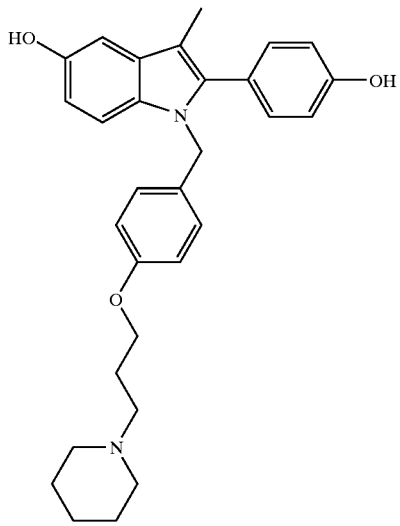

Example No. 166

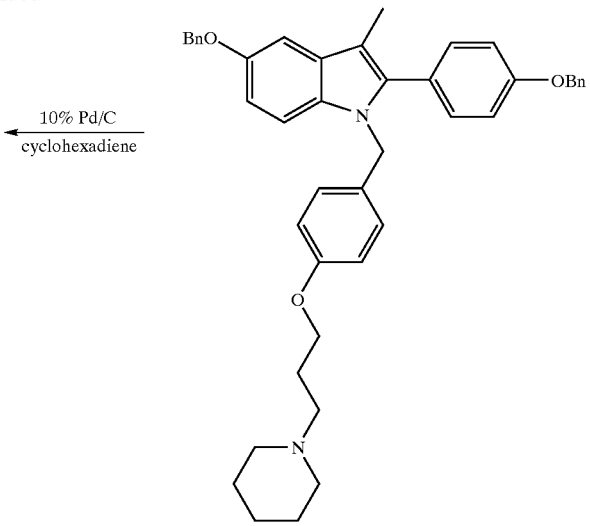

Example No. 165

EXAMPLE NO. 166
2-(4-Hydroxy-phenyl)-3-methyl-1-{4-[3-(piperidin-1-yl)-propoxy]-benzyl}-1H-indol-5-ol The title compound was prepared according to Scheme 16 and the steps provided below:

Method 11
EXAMPLE NO. 163a
4-(3-chloropropoxy)-benzyl alcohol

A solution of 4-hydroxy benzyl alcohol CAS No. [623–05–2] (10 g, 80.5 mmol) in ethanol (70 mL) was treated with 1,3 bromochloro propane (16.0 g, 100 mmol) and potassium hydroxide (5.0 g, 89 mmol) was refluxed for 2 hours. The solution was cooled and filtered and then the filtrate concentrated. The concentrate was taken up in ether and washed with water, brine and dried over magnesium sulfate. The material was chromatographed on silica gel using ethyl acetate/hexanes (3:7) to yield 11.6 g of the product as a white solid: Mp=65° C.; $^1$H NNR (DMSO) 7.21 (d, 2H, J=8.8 Hz), 6.88 (d, 2H, J=8.8 Hz), 5.03 (t, 1H, J=5.7 Hz), 4.40 (d, 2H, J=5.5 Hz), 4.05 (t, 2H, J=6.1 Hz), 3.77 (t, 2H, J=6.4 Hz); MS eI m/z 200.

Method 12
EXAMPLE NO. 163b
4-(3-chloropropoxy)-benzyl bromide

A solution consisting of 4-(3-chloropropoxy)-benzyl alcohol No. 162 (10.6 g, 52.8 mmol) in dioxane (0.125 l) was cooled to 0° C. and treated with a dropwise addition of thionyl bromide (12.0 g, 58.0 mmol). After 10 minutes the reaction was complete. The dioxane was diluted with ethyl ether and washed with water, brine, and then dried over MgSO$_4$. The material was concentrated down to yield 15 g of an oil: $^1$H NMR (DMSO) 7.36 (d, 2H, J=8.8 Hz), 6.92 (d, 2H, J=8.6 Hz), 4.68 (s, 2H), 4.08 (t, 2H, J=5.9 Hz), 3.77 (t, 2H, J=6.4 Hz); MS (FAB) 266 (M+H$^+$).

Method 13
EXAMPLE NO. 164
5-Benzyloxy-2-(4-benzyloxy-phenyl)-1-[4-(3-chloro-propoxy)-benzyl]-3-methyl-1H-indole A solution consisting of 5-Benzyloxy-2-(4-benzyoxy-phenyl)-3-metyl-1H-indole No. 7 (65 g, 15.5 mmol) in DMF (60 mL) was cooled to 0° C. and treated with addition of sodium hydride (0.68 g, 17.0 mmol) and stirred for 20 minutes. A solution of 4-(3-chloropropoxy)-benzyl bromide No. 163 in DMF (10 mL) was then added slowly. The reaction was allowed to come to rt and stirred for 2 hours. The reaction was poured into water and extracted with ethyl acetate. The ethyl acetate was washed with water, brine and dried over magnesium sulfate and concentrated The concentrate was treated with methanol and 5 g of the desired product precipitated as a white solid with a melting point of 130–132° C.

Method 14
EXAMPLE NO. 165
5-Benzyloxy-2-(4-benzyloxy-phenyl)-1-[4-(3-piperidin-1-yl-propoxy)-benzyl]-3-methyl-1H-indole A solution of 5-Benzyloxy-2-(4-benzyloxy-phenyl)-1-[4-(3-chloro-propoxy)-benzyl]-3-methyl-1H-indole No. 164 (3 g, 5.1 mmol), potassium iodide (2.5 g, 15.3 mmol) and piperidin (3.0 mL, 30.6 mmol) were heated in DMF (30 mL) at 100° C. for 18 hours. The reaction was worked up by pouring into water and extracting with ethyl acetate. The organic layer was washed with water, brine and dried over magnesium sulfate. The solution was concentrated to an oil and the product precipitated out by adding methanol. The product was obtained as a white solid: Mp=104–106° C.; $^1$H NMR (DMSO) 7.47 (d, 4H, J=7.5 Hz), 7.38 (q, 4H, J=7.9 Hz), 7.36–7.30 (m, 1H), 7.28 (d, 2H, J=8.3 Hz), 7.19 (d, 1H, J=8.8 Hz), 7.12–7.10 (m, 4H), 6.80 (dd, 1H, J=8.8, 2.0 Hz), 6.72 (s, 4H), 5.14 (s, 2H), 5.13 (s, 2H), 5.11 (s, 2H), 3.86 (t, 2H, J=6.4 Hz), 2.35–2.20 (m, 6H), 2.14 (s, 3H), 1.78–1.75 (m, 2H), 1.47–1.42 (m, 4H), 1.40–1.31 (m, 2H); MS eI m/z 650.

Method 15
EXAMPLE NO. 166
2-(4-Hydroxy-phenyl)-3-methyl-1-{4-[3-piperidin-1-yl)-propoxy]-benzyl}-1H-indol-5-ol A solution of 5-Benzyloxy-2-(4-benzyloxy-phenyl)-1-[4-(3-piperidin-1-yl-propoxy)-benzyl]-3-methyl-1H-indole No. 165 (235 g) in tetrahydrofuran (25 mL) and ethanol (25 mL) was added to 2.3 g of 10% palladium on carbon. Cyclohexadiene (10 mL) was added and the reaction allowed to stir at room temperature for 18 hours. The catalyst was filtered through celite and the reaction mixture was concentrated and chromatographed on silica gel using dichloromethane/methanol (4:1) to elute the product (0.8 g) as a white foam: Mp=125–130° C.; $^1$H NMR 9.68 (s, 1H), 8.70 (s, 1H), 7.15 (d, 2H, J=8.6 Hz), 7.05 (d, 1H, J=8.8 Hz), 6.85 (d, 2H, J=8.6 Hz), 6.80 (d, 1H, J=2.4 Hz), 6.74 (d, 4H, J=2.6 Hz), 6.57 (dd, 1H, J=8.6, 2.2 Hz), 5.09 (s, 2H), 3.88 (t, 2H, J=6.4 Hz), 3.60–3.15 (m, 2H), 2.62–2.38 (m, 4H), 2.09 (s, 3H), 1.92–1.78 (m, 2H), 1.55–1.43 (m, 4H), 1.42–1.30 (m, 2H); IR (KBr) 3400 (br), 2900, 1620, 1515 cm−1; MS eI m/z 470.

Synthesis of No. 167 and No. 168
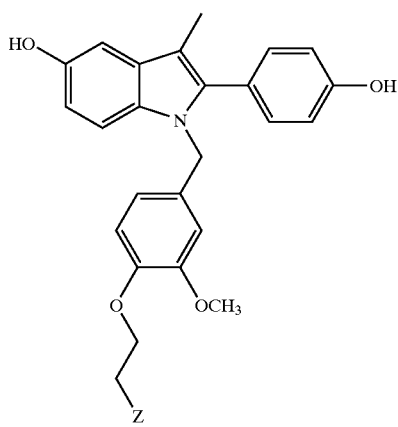
TABLE 10
| Example No. | Z |
|---|---|
| No. 167 | piperidine |
| No. 168 | azepane |
Scheme 17
Synthetic scheme for example No. 167 and No. 168
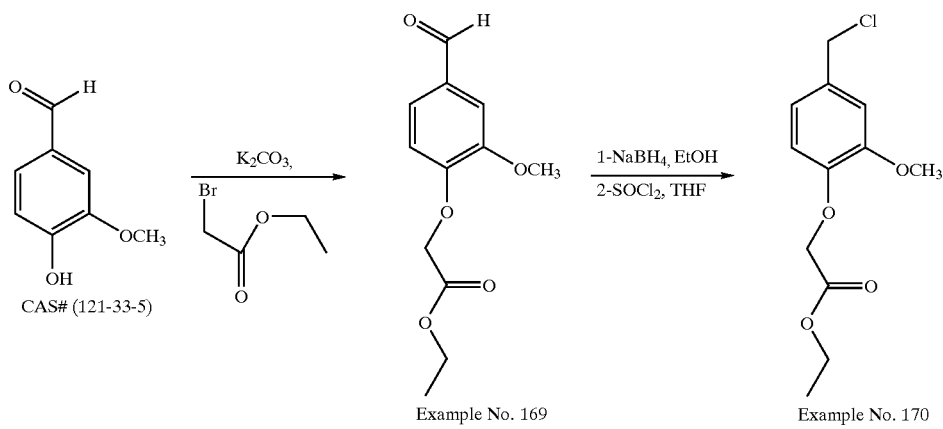
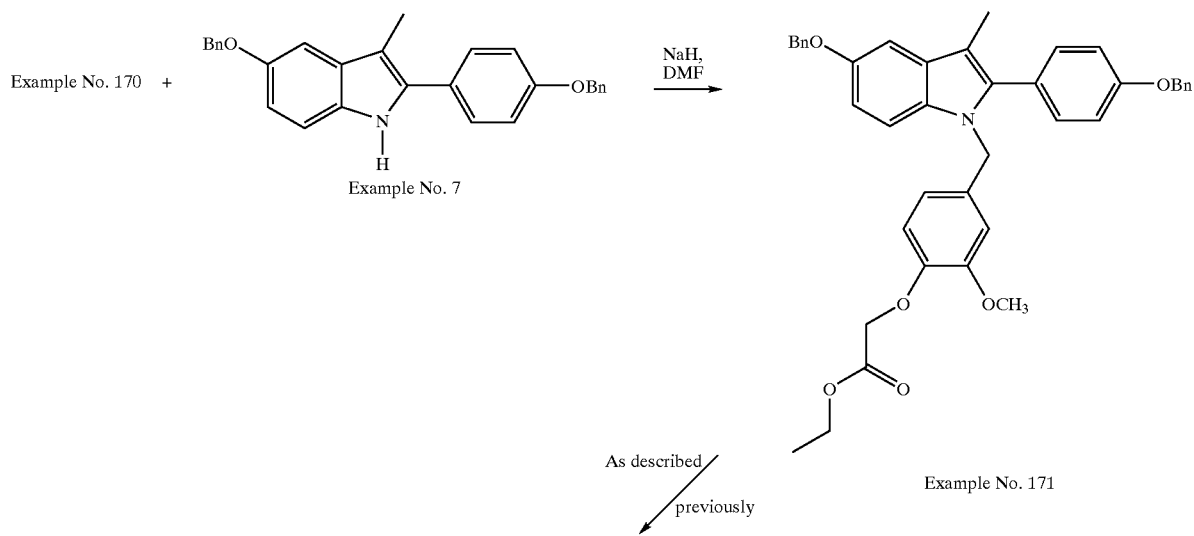

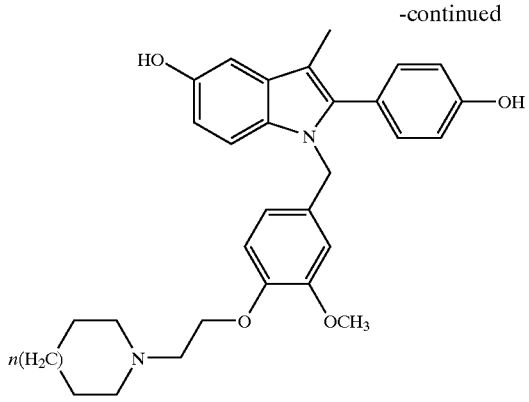

Example No. 167, n = 1
Example No. 168, n = 2

Synthesis of Example No. 167

2-(4-Hydroxy-phenyl)-1-[3-methoxy-4-(2-piperidin-1-yl-ethoxy)-benzyl]-3-methyl-1H-indol-5-ol

EXAMPLE NO. 169

(4-Formyl-2-methoxy-phenoxy)-acetic acid ethyl ester

A flask containing vanillin (20 g, 0.13 mol), ethyl bromoacetate (28.4 g, 0.17 mol) and potassium carbonate (32.7 g. 0.24 mol) and acetone 200 mL were heated to reflux for 3 hours. The reaction was allowed to come to rt. The acetone was stripped off and the residue partitioned between water and ethyl acetate. The ethyl acetate was washed with brine and dried over magnesium sulfate. The organic layer was concentrated and the solid triturated with hexanes to yield 28.4 grams of example No. 169.

Mp+=56–59°C.; $^1$H NMR (DMSO) 9.83 (s, 1H), 7.50 (dd, 1H, J=2.0 Hz, 8.3 Hz), 7.42 (d, 1H, J=1.7 Hz), 7.07 (d, 1H, J=8.4 Hz), 4.91 (s, 2H), 4.16 (q, 2H, J=7.2 Hz), 3.84 (s, 3H), 1.20 (t, 3H, J=7.1 Hz); MS eI m/z 238 (M+); CHN calcd for $C_{12}H_{14}O_5$.

EXAMPLE NO. 170

(4-Chloromethyl-2-methoxy-phenoxy)-acetic acid ethyl ester

A solution of example No. 169 (28.8 g, 0.119 mol) in 600 mL of EtOH/THF(1:1) was treated with sodium borohydride (2.25 g, 0.06 mol) at 0° C. and stirred for 45 minutes. The solvents were evaporated and the reaction mixture diluted with ethyl acetate and washed with 1N HCl solution. The product thus obtained (14.2 g, 0.059 mol) as an oil was dissolved in 140 mL of THF and cooled to 0° C. This solution was then treated with dropwise addition of thionyl chloride (7.38 g, 0.062 mol) at )° C. After 1 hour the reaction was poured into 400 mL of water and extracted with ether. The ether layer was washed with a sodium bicarbonate solution and dried over magnesium sulfate. This was concentrated and chromatographed by silica gel chromatography using ethyl acetate/hexanes (1:9). The product was obtained as 10.5 g of a white solid. Mp=64–66° C.; $^1$H NMR (DMSO) 7.06 (d, 1H, J=2.0 Hz), 6.91 (dd, 1H, J=2.0 Hz, 2.2 Hz), 6.83 (d, 1H, J=2.1 Hz), 4.75 (s, 2H), 4.70 (s, 2H), 4.13 (q, 2H, J=7.2 Hz), 3.77 (s, 3H), 1.19 (t, 3H, J=7.1 Hz); MS eI m/z 258 (M+); CHN calcd for $C_{12}H_{15}ClO_4$.

EXAMPLE NO. 171

{2-Methoxy-4-[5-benzyloxy-2-(4-benzyloxy-phenyl)-3-methyl-indol-1-ylmethyl]-phenoxy}-acetic acid ethyl ester Alkylation of the indole No. 7 was performed as described previously in Method No. 3 using example No. 170 as the electrophile.

Mp=120–123° C.; $^1$H NMR (DMSO) 7.48–7.20 (m, 13H), 7.18–7.10 (m, 3H), 6.80 (dd, 1H, J=2.5 Hz, 8.8 Hz), 6.64 (d, 1H, J=8.4 Hz), 6.52 (d, 1H, J=2.0 Hz), 6.24 (dd, 1H, J=1.9 Hz, 8.1 Hz), 5.13 (s, 4H), 5.10 (s, 2H), 4.61 (s, 2H), 4.10 (q, 2H, J=7.0 Hz) 3.58 (s, 3H), 2.15 (s, 3H), 1.15 (t, 3H, J=7.0 Hz); MS eI m/z 641 (M+).

EXAMPLE NO. 172

2-{2-Methoxy-4-[5-benzyloxy-2-(4-benzyloxy-phenyl)-3-methyl-indol-1-ylmethyl]-phenoxy}-ethanol Reduction of the ester No. 171 was performed as described previously in Method 4.

Mp=86–90° C.; $^1$H NMR (DMSO) 7.48–7.20 (m, 13H), 7.18–7.10 (m, 3H), 6.80 (dd, 1H, J=2.5 Hz, 8.8 Hz), 6.64 (d, 1H, J=8.4 Hz), 6.52 (d, 1H, J=2.0 Hz), 6.24 (dd, 1H, J=1.9 Hz, 8.1 Hz), 5.13 (s, 4H), 5.10 (s, 2H), 4.76 (t, 1H, J=5.5 Hz), 3.83 (t, 2H, J=5.1 Hz), 3.63 (q, 2H, J=5.3 Hz), 3.56 (s, 3H), 2.15 (s, 3H); MS eI m/z 599 (M+).

EXAMPLE NO. 173

5-Benzyloxy-2-(4-benzyloxy-phenyl)-1-[3-methoxy-4-(2-bromo-ethoxy)-benzyl]-3-methyl-1H-indole Conversion of the alcohol of example No. 172 to the bromide was performed analogously to that described in Method 5.

Mp=150–152° C.; $^1$H NMR (DMSO) 7.48–7.20 (m, 13H), 7.18–7.10 (m, 3H), 6.80 (dd, 1H, J=2.5 Hz, 8.8 Hz), 6.64 (d, 1H, J=8.4 Hz), 6.52 (d, 1H, J=2.0 Hz), 6.24 (dd, 1H,

J=1.9 Hz, 8.1 Hz), 5.13 (s, 4H), 5.10 (s, 2H), 4.15 (t, 2H, J=5.3 Hz), 3.70 (t, 2H, J=5.7 Hz), 3.58 (s, 3H), 2.15 (s, 3H); MS eI m/z 661 (M+).

EXAMPLE NO. 174

5-Benzyloxy-2-(4-benzyloxy-phenyl)-3-methyl-1-[3-Methoxy-4-(2-piperidin-1-yl-ethoxy)-benzyl]-1H-indole Substitution of the bromide with piperidine was performed as described previously in Method 6.

$^1$H NMR (DMSO) 7.48–7.20 (m, 13H), 7.18–7.10 (m, 3H), 6.80 (dd, 1H, J=2.5 Hz, 8.8 Hz), 6.64 (d, 1H, J=8.4 Hz), 6.52 (d, 1H, J=2.0 Hz), 6.24 (dd, 1H, J=1.9 Hz, 8.1 Hz), 5.13 (s, 4H), 5.10 (s, 2H), 3.90 (t, 2H, J=5.7 Hz), 3.55 (s, 3H), 2.62–2.50 (bs, 2H), 2.45–2.30 (bs, 4H), 2.15 (s, 3H), 1.50–1.40 (m, 4H), 1.40–1.35 (m, 2H); MS FAB m/z 667 (M+H+).

EXAMPLE NO. 175

5-Benzyloxy-2-(4-benzyloxy-phenyl)-3-methyl-1-[2-Methoxy-4-(2-azepan-1-yl-ethoxy)-benzyl]-1H-indole Reaction performed exactly as for No. 174 except hexamethyleneamine was used to displace the bromide in place of piperidine.

Foam; $^1$H NMR (DMSO) 7.48–7.20 (m, 13H), 7.18–7.10 (m, 3H), 6.80 (dd, 1H, J=2.5 Hz, 8.8 Hz), 6.64 (d, 1H, J=8.4 Hz), 6.52 (d, 1H, J=2.0 Hz), 6.24 (dd, 1H, J=1.9 Hz, 8.1 Hz), 5.13 (s, 4H), 5.10 (s, 2H), 3.90 (t, 2H, J=5.7 Hz), 3.55 (s, 3H), 2.85–2.70 (bs, 2H), 2.70–2.55 (s, 4H), 2.10 (s, 3H), 1.60–1.15 (m, 8H); MS FAB m/z 681 (M+H+).

EXAMPLE NO. 167

2-(4-Hydroxy-phenyl)-1-[3-methoxy-4-(2-piperidin-1-yl-ethoxy)-benzyl]-3-methyl-1H-indol-5-ol Compound No. 173 was hydrogenated by transfer hydrogenation as described previously in Method 7. Compound was isolated as the hydrochloride salt by dissolving in ether and treading with 1.2 equivalents of 1N ether/HCl solution (this is a variation of method 8).

Mp=123–127° C.; $^1$H NMR (DMSO) 10.20 (bs, 1H), 9.72 (s, 1H), 8.71 (s, 1H), 7.17 (d, 2H, J=8.6 Hz); 7.11 (d, 1H, J=8.8 Hz), 6.87 (d, 2H, J=8.6 Hz), 6.79 (m, 2H), 6.57 (dd, 1H, J=2.4 Hz, 8.8 Hz), 6.55 (d, 1H, J=1.7 Hz), 6.33 (dd, 1H, J=1.7 Hz, 8.1 Hz), 5.11 (s, 2H), 4.23 (t, 2H, J=4.8 Hz), 3.60 (s, 3H), 3.45 (m, 2H), 3.35 (m, 2H), 2.95 (m, 2H), 2.10 (s, 3H), 1.70 (m, 5H), 1.35 (m, 1H); IR 3500, 1500, 1275 cm$^{-1}$; MS (+) FAB m/z 487 (M+H)$^+$; CHN calcd for $C_{30}H_{34}N_2O_4$+1HCl+1.0H$_2$O.

EXAMPLE NO. 168

2-(4-Hydroxy-phenyl)-1-[3-methoxy-4-(2-azepan-1-yl-ethoxy)-benzyl]-3-methyl-1H-indol-5-ol Prepared in the same way as that described for example No. 167.

Mp=142–146° C.; $^1$H NMR (DMSO) 10.36 (s, 1H), 9.72 (s, 1H), 8.71 (s, 1H), 7.18 (d, 2H, J=8.3 Hz), 7.11 (d, 1H, J=8.6 Hz), 6.87 (d, 2H, J=8.3 Hz), 6.82 (d, 1H, J=8.1 Hz), 6.79 (d, 1H, J=2.2 Hz), 6.57 (dd, 1H, J=2.2 Hz, 8.6 Hz), 6.55 (d, 1H, J=1.8 Hz), 6.33 (dd, 1H, J=1.5 Hz 8.1 Hz), 5.11 (s, 2H), 4.24 (t, 2H, J=4.6 Hz), 3.60 (s, 3H), 3.40 (m, 4H), 3.20 (m, 2H), 2.10 (s, 3H); 1.75 (m, 4H), 1.55 (m, 4H); IR (KBr) 3300, 1500, 1270, 1200 cm$^{-1}$; MS (+) FAB m/z 501 (M+H)$^+$; CHN calcd for $C_{31}H_{36}N_2O_4$+1.0HCl+0.12CH$_3$OH.

Biological Data

Method 16

In Vitro Estrogen Receptor Binding Assay

Receptor Preparation

CHO cells overexpressing the estrogen receptor were grown in 150 mm$^2$ dishes in DMEM+10% dextran coated charcoal, stripped fetal bovine serum. The plates were washed twice with PBS and once with 10 mM Tris-HCl, pH 7.4, 1 mM EDTA. Cells were harvested by scraping the surface and then the cell suspension was placed on ice. Cells were disrupted with a hand-held motorized tissue grinder using two, 10-second bursts. The crude preparation was centrifuged at 12,000 g for 20 minutes followed by a 60 minute spin at 100,000 g to produce a ribosome free cytosol. The cytosol was then frozen and stored at –80° C. Protein concentration of the cytosol was estimated using the BCA assay with reference standard protein.

Bindings Assay Conditions

The competition assay was performed in a 96-well plate (polystyrene*) which binds <2.0% of the total input [$^3$H]-17β-estradiol and each data point was gathered in triplicate. 100 uG/100 uL of the receptor preparation was aliquoted per well. A saturating dose of 2.5 nM [$^3$H] 17β-estradiol+ competitor (or buffer) in a 50 uL volume was added in the preliminary competition when 100× and 500× competitor were evaluated, only 0.8 nM [$^3$H] 17β-estradiol was used. The plate was incubated at room temperature for 2.5 h. At the end of this incubation period 150 uL of ice-cold dextran coated charcoal (5% activated charcoal coated with 0.05% 69K dextran) was added to each well and the plate was immediately centrifuged at 99 g for 5 minutes at 4° C. 200 uL of the supernatant solution was then removed for scintillation counting. Samples were counted to 2% or 10 minutes, whichever occurs first. Because polystyrene absorbs a small amount of [$^3$H] 17β-estradiol, wells containing radioactivity and cytosol, but not processed with charcoal were included to quantitate amounts of available isotope. Also, wells containing radioactivity but no cytosol were processed with charcoal to estimate unremovable DPM of [$^3$H] 17β-estradiol. Corning No. 25880-96, 96-well plates were used because they have proven to bind the least amount of estradiol.

Analysis of Results

Counts per minute (CPM) of radioactivity were automatically converted to disintegrated per minute (DPM) by the Beckman LS 7500 Scintillation Counter using a set of quenched standards to generate a H No. for each sample. To calculate the % of estradiol binding in the presence of 100 or fold 500 fold competitor the following formula was applied:

((DPM sample-DPM not removed by charcoal/(DPM estradiol-DPM not removed by charcoal))×100%=% of estradiol binding For the generation of $IC_{50}$ curves, % binding is plotted vs compound. $IC_{50}$'s are generated for compounds that show >30% competition at. 500× competitor concentration. For a description of these methods, see Hulme, E. C., ed. 1992. Receptor-Ligand Interactions: A Pracical Approach. IRL Press, New York(see especially chapter 8).

TABLE 11

Estrogen Receptor Binding

| Example No. | X | O | Z | Receptor Binding IC50's uM |
|---|---|---|---|---|
| No. 85 | H | H |  | 0.45 |
| No. 86 | H | 4'-OH |  | 0.12 |
| No. 87 | OH | H |  | 0.030 |
| No. 88 | OMe | 4'-OH |  | 0.35 |
| No. 89 | OH | 4'-OMe |  | 0.30 |
| No. 90 | OMe | 4'-OMe |  | 0.60 |
| No. 91 | OMe | 4'-OMe |  | 0.52 |
| No. 92 | OH | 4'-OEt |  | 0.062 |

TABLE 11-continued

Estrogen Receptor Binding

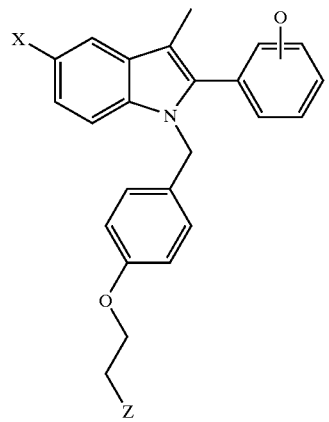

| Example No. | X | O | Z | Receptor Binding IC50's uM |
|---|---|---|---|---|
| No. 93 | OH | 4'-OEt | 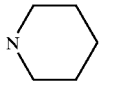 | 0.090 |
| No. 94 | F | 4'-OH | 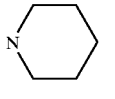 | 0.20 |
| No. 97 | OH | 4'-OH |  | 0.060 |
| No. 98 | OH | 4'-OH |  | 0.050 |
| No. 99 | OH | 4'-OH | 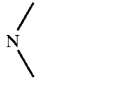 | 0.03 |
| No. 100 | OH | 4'-OH | 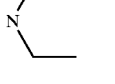 | 0.06 |
| No. 101 | OH | 4'-OH | 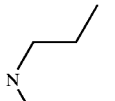 | 0.04 |
| No. 102 | OH | 4'-OH |  | 0.08 |

TABLE 11-continued

Estrogen Receptor Binding

| Example No. | X | O | Z | Receptor Binding IC50's uM |
|---|---|---|---|---|
| No. 103 | OH | 4'-OH | N(butyl)(butyl) | 0.2 |
| No. 104 | OH | 4'-OH | N(iPr)(iPr) | 0.1 |
| No. 105 | OH | 4'-OH | N(Me)(butyl) | 0.028 |
| No. 106 | OH | 4'-OH | N(Me)2(Me)+ I- | 0.1 |
| No. 107 | OH | 4'-OH | N-methylpiperidinium I- | 0.06 |
| No. 108 | OH | 4'-OH | 2-methylpiperidine | 0.02 |
| No. 109 | OH | 4'-OH | 3-methylpiperidine | 0.17 |
| No. 110 | OH | 4'-OH | 4-methylpiperidine | 0.037 |
| No. 111 | OH | 4'-OH | 3,3-dimethylpiperidine | 0.015 |
| No. 112 | OH | 4'-OH | 2,6-dimethylpiperidine | 0.07 |
| No. 113 | OH | 4'-OH | 4-hydroxypiperidine | 0.047 |
| No. 114 | OH | 4'-OH | azabicyclic | 0.001 |
| No. 115 | OH | 4'-OH | trimethyl-azabicyclic | 0.15 |
| No. 116 | OH | 4'-Fl | piperidine | 0.04 |

TABLE 11-continued

Estrogen Receptor Binding

| Example No. | X | O | Z | Receptor Binding IC50's uM |
|---|---|---|---|---|
| No. 117 | OH | 4'-Fl | azepane (7-ring N) | 0.10 |
| No. 118 | OH | 3'-OMe,4'-OH | piperidine | N/A |
| No. 119 | OH | 3',4'-OCH₂O— | piperidine | 0.070 |
| No. 120 | OH | 4'-O-iPr | piperidine | 0.10 |
| No. 121 | OH | 4'-O-iPr | azepane | 0.080 |
| No. 122 | OH | 4'-O-Cp | piperidine | 0.080 |
| No. 123 | OH | 4'-CF₃ | piperidine | 0.17 |
| No. 124 | OH | 4'-CH₃ | piperidine | 0.11 |
| No. 125 | OH | 4'-Cl | piperidine | 0.11 |
| No. 126 | OH | 2',4',-Dimethoxy | piperidine | N/A |
| No. 127 | OH | 3'-OH | piperidine | 0.019 |
| No. 128 | OH | 3'-OH | azepane | 0.009 |
| No. 129 | OH | 4'-OH,3'-Fl | piperidine | 0.0055 |
| No. 130 | OH | 4'-OH,3'-Fl | azepane | 0.013 |
| No. 131 | OH | 3'-OMe | piperidine | 0.12 |
| No. 132 | OH | 4'-OCF₃ | piperidine | 0.05 |

TABLE 12

Estrogen Receptor Binding

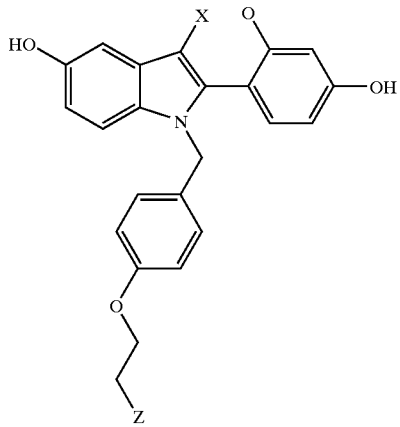

| Example No. | X | O | Z | Receptor Binding IC50's uM |
|---|---|---|---|---|
| No. 133 | Cl | H | pyrrolidine | 0.004 |
| No. 134 | Cl | H | piperidine | 0.024 |
| No. 135 | Cl | H | azepane | 0.029 |
| No. 136 | Cl | CH$_3$ | piperidine | 0.013 |
| No. 137 | Et | H | piperidine | 0.15 |
| No. 138 | CN | H | piperidine | 0.011 |

TABLE 12-continued

Estrogen Receptor Binding

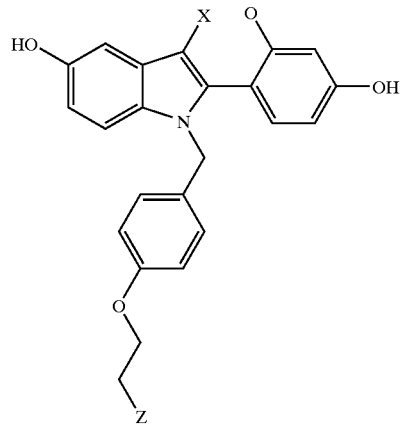

| Example No. | X | O | Z | Receptor Binding IC50's uM |
|---|---|---|---|---|
| No. 139 | CN | H | azepane | 0.023 |

TABLE 13

Estrogen Receptor Binding

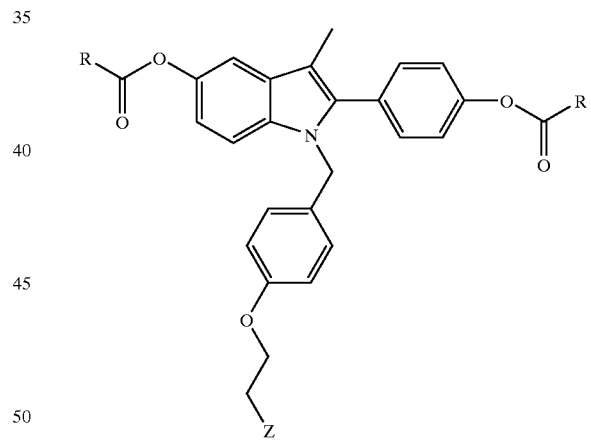

| Example No. | R | Z | Receptor Binding IC50's uM |
|---|---|---|---|
| No. 160 | Et | azepane | N/A |
| No. 161 | t-Bu | azepane | N/A |
| No. 162 | t-Bu | piperidine | Does not Bind |

TABLE 14

Estrogen Receptor Binding

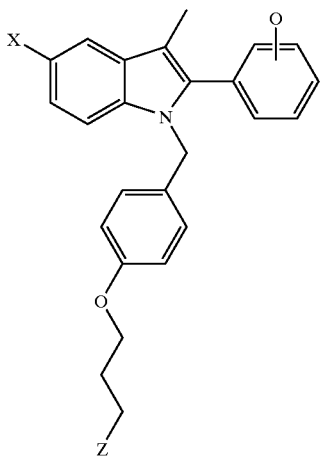

| Example No. | X | O | Z | Receptor Binding IC50's uM |
|---|---|---|---|---|
| No. 166 | OH | 4'-OH | piperidine | 0.099 |

TABLE 15

Estrogen Receptor Binding

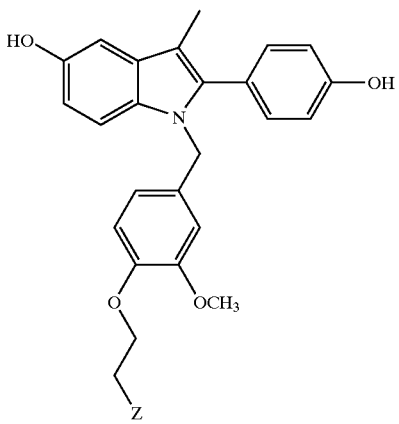

| Example No. | Z | Receptor Binding IC50's uM |
|---|---|---|
| No. 167 | piperidine | 0.08 |
| No. 168 | azepane | 0.057 |

Ishikawa Cell Alkaline Phosphatase Assay (Cell Maintenance and Treatment

Ishikawa cells were maintained in DMEM/F12 (50%:50%) containing phenol red+10% fetal bovine serum and the medium was supplemented with 2 mM Glutamax, 1% Pen/Strap and 1 mM sodium pyruvate. Five days prior to the beginning of each experiment (treatment of cells) the medium was changed to phenol red-free DMEM/F12+10% dextran coated charcoal stripped serum. On the day before treatment, cells were harvested using 0.5% trypsin/EDTA and plated at a density of $5 \times 10^4$ cells/well in 96-well tissue culture plates. Test compounds were dosed at $10^{-6}$, $10^{-7}$ and $10^{-8}$M in addition to $10^{-6}$ M (compound)+$10^{-9}$ M 17β-estradiol to evaluate the ability of the compounds to function as antiestrogens. Cells were treated for 48 h prior to assay. Each 96-well plate contained a 17βestradiol control. Sample population for at each dose was n=8.

Alkaline Phosphatase Assay:

At the end of 48 h the media is aspirated and cells are washed three times with phosphate buffered saline (PBS). 50 μL of lysis buffer (0.1 M Tris-HCl, pH 9.8, 0.2% Triton X-100) is added to each well. Plates are placed at −80° C. for a minimum of 15 minutes. Plates are thawed at 37° C. followed by the addition of 150 μL of 0.1 M Tris-HCl, pH 9.8, containing 4 mM para-nitrophenylphosphate (pNPP) to each well (final concentration, 3 mM pNPP).

Absorbance and slope calculations were made using the KineticCalc Application program (Bio-Tek Instruments, Inc., Winooski, Vt.). Results are expressed as the mean +/− S.D. of the rate of enzyme reaction (slope) averaged over the linear portion of the kinetic reaction curve (optical density readings every 5 minutes for 30 minutes absorbance reading). Results for compounds are summarized as percent of response related to 1 nM 17β-estradiol.

Various compounds were assayed for estrogenic activity by the a phosphatase method and corresponding ED50 values (95% C.I.) were calculated The four listed in the following were used as as reference standards:

| | |
|---|---|
| 17β-estradiol | 0.03 nM |
| 17α-estradiol | 1.42 nM |
| estriol | 0.13 nM |
| estrone | 0.36 nM |

A description of these methods is described by Holinka, C. F., Hata, H., Kuramoto, H, and Gurpide, E. (1986) Effects of steroid hormones and antisteroids on alkaline phosphatase activity in human endometria cancer cells (Ishikawa Line). Cancer Research, 46:2771–2774, and by Littlefield, B. A., Gurpide, E., Markiewicz, L., McKinley, B. and Hochberg, R. B. (1990) A simple and sensitive microtiter plate estrogen bioassay based on stimulation alkaline phosphatase in Ishikawa cells;. Estrogen action of D5 adrenal steroids. Endocrinology. 6:2757–2762.

Ishikawa Alkaline Phosphatase Assay

| Compound | % Activation |
|---|---|
| 17β-estradiol | 100% activity |
| tamoxifen | 0% activity (45% with 1 nM 17β-estradiol) |
| raloxifene | 5% activity (5% with 1 nM 17β-estradiol) |
| Example No. 98 | 1% activity (1% with 1 nM 17β-estradiol) |

Method No. 18

2× VIT ERE Infection Assay

Cell Maintenance and Treatment

Chinese Hamster Ovary cells (CHO) which had been stably transfected with the human estrogen receptor were maintained in DMEM+10% fetal bovine serum (FBS). 48 h prior to treatment the growth medium was replaced with DMEM lacking phenol red+10% dextran coated charcoal stripped FBS (treatment medium). Cells were plated at a density of 5000 cells/well in 96-well plates containing 200 μL of medium/well.

Calcium Phosphate Transfection

Reporter DNA (Promega plasmid pGL2 containing two tandem copies of the vitellogenin ERE in front of the minimal thymidine kinase promoter driving the luciferase gene) was combined with the B-galactosidase expression plasmid pCH110 (Pharmacia) and carrier DNA (pTZ18U) in the following ratio:

10 uG of reporter DNA
5 uG of pCH110DNA
5 uG of pTZ18U
20 uG of DNA/1 mL of transfection solution The DNA (20 uG) was dissolved in 500 uL of 250 mm sterile CaCl2 and added dropwise to 500 uL of 2× HeBS (0.28 M NaCl, 50 mM HEPES, 1.5 mM $Na_2HPO_4$, pH 7.05) and incubated at room temperature for 20 minutes. 20 uL of this mixture was added to each well of cells and remained on the cells for 16 h. At the end of this incubation the precipitate was removed, the cells were washed with media, fresh treatment media was replaced and the cells were treated with either vehicle, 1 nM 17β-estradiol, 1 uM compound or 1 uM compound+1 nM 17β-estradiol (tests for estrogen antagonism). Each treatment condition was performed on 8 wells (n=8) which were incubated for 24 h prior to the luciferase assay.

Luciferase Assay

After 24 h exposure to compounds, the media was removed and each well washed with 2× with 125 uL of PBS lacking $Mg^{++}$ and $Ca^{++}$. After removing the PBS, 25 uL of Promega lysis buffer was added to each well and allowed to stand at room temperature for 15 min, followed by 15 min at −80° C. and 15 min at 37° C. 20 uL of lysate was transferred to an opaque 96 well plate for luciferase activity evaluation and the remaining lysate (5 uL) was used for the B-galactosidase activity evaluation (normalize transfection). The luciferan substrate (Promega) was added in 100 uL aliquots to each well automatically by the luminometer and the light produced (relative light units) was read 10 seconds after addition.

Infection Luciferase Assay (Standards)

| Compound | % Activation |
|---|---|
| 17β-estradiol | 100% activity |
| estriol | 38% activity |
| tamoxifen | 0% activity (10% with 1 nM 17β-estradiol) |
| raloxifene | 0% activity (0% with 1 nM 17β-estradiol) |

B-Galactosidase Assay

To the remaining 5 uL of lysate 45 uL of PBS was added. Then 50 uL of Promega B-galactosidase 2× assay buffer was added, mixed well and incubated at 37° C. for 1 hour. A plate containing a standard curve (0.1 to 1.5 milliunits in triplicate) was set up for each experimental run. The plates were analyzed on a Molecular Devices spectrophotometric plate reader at 410 nm. The optical densities for the unknown were converted to milliunits of activity by mathematical extrapolation from the standard curve.

Analysis of Results

The luciferase data was generated as relative light units (RLUs) accumulated during a 10 second measurement and automatically transferred to a JMP (SAS Inc) file where background RLUs were subtracted. The B-galactosidase values were automatically imported into the file and these values were divided into the RLUs to normalize the data. The mean and standard deviations were determined from a n=8 for each treatment. Compounds activity was compared to 17β-estradiol for each plate. Percentage of activity as compared to 17β-estradiol was calculated using the formula %=((Esradiol-control)/(compound value))×100. These techniques are described by Tzukerman, M. T., Esty, A., Santiso-Mere, D., Danielian, P., Parker, M. G., Stein, R. B., Pike, J. W. and McDonnel, D. P. (1994). Human estrogen receptor transactivational capacity was determined by both cellular and promoter context and mediated by two functionary distinct intramolecular regions (see Molecular Endocrinology, 8:21–30).

TABLE 16

Infection Luciferase Activity

| Example No. | 1 uM | 1 uM + 17β estradiol |
|---|---|---|
| No. 85 | −2 | 43 |
| No. 86 | −5 | 2 |
| No. 87 | 0 | 0 |
| No. 88 | 4 | 44 |
| No. 89 | 16 | 18 |
| No. 90 | 3 | 58 |
| No. 91 | −3 | 56 |
| No. 92 | −4 | −2 |
| No. 93 | −3 | −2 |
| No. 94 | −5 | 15 |
| No. 95 | −4 | −4 |
| No. 96 | 12 | 8 |
| No. 97 | −4 | −5 |
| No. 98 | 5 | 5 |
| No. 99 | 5 | 6 |
| No. 100 | 9 | 10 |
| No. 101 | 14 | 9 |
| No. 102 | 9 | 10 |
| No. 103 | 13 | 10 |
| No. 104 | 7 | 7 |
| No. 105 | 5 | 5 |
| No. 106 | 10 | 81 |

TABLE 16-continued

Infection Luciferase Activity

| Example No. | 1 uM | 1 uM + 17β estradiol |
|---|---|---|
| No. 107 | −1 | 54 |
| No. 108 | 11 | 10 |
| No. 109 | 6 | 5 |
| No. 110 | 8 | 10 |
| No. 111 | 25 | 23 |
| No. 112 | 10 | 10 |
| No. 113 | 14 | 16 |
| No. 114 | 1 | −1 |
| No. 115 | 11 | 10 |
| No. 116 | −1 | 1 |
| No. 117 | 0 | 1 |
| No. 118 | N/A | N/A |
| No. 119 | −1 | −1 |
| No. 120 | −1 | 1 |
| No. 121 | 0 | 1 |
| No. 122 | 1 | 5 |
| No. 123 | −1 | 1 |
| No. 124 | −2 | −2 |
| No. 125 | −3 | −2 |
| No. 126 | −1 | 0 |
| No. 127 | −3 | −4 |
| No. 132 | −5 | −2 |
| No. 133 | 7 | 9 |
| No. 134 | 9 | 5 |
| No. 135 | 7 | 3 |
| No. 136 | 16 | 10 |
| No. 137 | 6 | 8 |
| No. 138 | −2 | −1 |
| No. 139 | −12 | −13 |
| No. 160 | N/A | N/A |
| No. 161 | N/A | N/A |
| No. 162 | −14 | −13 |
| No. 166 | 25 | 23 |
| No. 167 | 4 | 10 |
| No. 168 | 3 | 7 |

Method No. 19

Rat Uterotrophic/Antiuterotrophic Bioassay

The estrogenic and antiestrogenic properties of the compounds were determined in an immature rat uterotrophic assay (4 day) that (as described previously by L. J. Black and R. L. Goode, Life Sciences, 26, 1453 (1980)). Immature Sprague-Dawley rats (female, 18 days old) were tested in groups of six. The animals were treated by daily ip injection with 10 uG compound, 100 uG compound, (100 uG compound+1 uG 17βestradiol) to check antiestrogenicity, and 1 uG 17β-estradiol, with 50% DMSO/50% saline as the injection vehicle. On day 4 the animals were sacrificed by $CO_2$ asphyxiation and their uteri were removed and stripped of excess lipid, any fluid removed and the wet weight determined. A small section of one horn was submitted for histology and the remainder used to isolate total RNA in order to evaluate complement component 3 gene expression.

TABLE 17

3 Day Rat Immature Uterine Assay

| Example No. | Uterine wt mg 100 uG cmpd | Uterine wt mg 100 uG cmpd + 1 uG 17β-estradiol | Uterine wt mg 1 uG 17β-estradiol | Uterine wt mg Vehicle |
|---|---|---|---|---|
| Tamoxifen | 71.4 mg | N/A | 98.2 mg | 42.7 mg |
| No. 85 | 41.1 mg | 92.4 mg | 94.4 mg | 26.6 mg |
| No. 94 | 28.1 mg | 93.7 mg | 88.5 mg | 22.3 mg |
| No. 97 | 27.4 mg | 24.3 mg | 63.2 mg | 30.7 mg |
| No. 98 | 29.4 mg | 27.9 mg | 94.1 mg | 35.9 mg |
| No. 100 | 59.9 mg | 68.7 mg | 91.9 mg | 23.4 mg |
| No. 101 | 65.1 mg | 71.0 mg | 113.7 mg | 27.7 mg |
| No. 122 | 46.7 mg | 38.7 mg | 103.4 mg | 30.3 mg |
| No. 123 | 39.2 mg | 61.4 mg | 94.4 mg | 26.1 mg |
| No. 138 | 28.4 mg | 37.9 mg | 93.9 mg | 24.6 mg |
| No. 139 | 30.4 mg | 45.0 mg | 82.1 mg | 20.5 mg |
| No. 168 | 43.2 mg | 81.7 mg | 98.9 mg | 25.5 mg |

Method No. 20

6-Week Ovariectomized Rat Model

Female Sprague Dawley CD rats, ovx or sham ovx, were obtained 1 day after surgery from Taconic Farm (weight range 240–275 g). They were housed 3 or 4 rats/cage in a room 14/10 (ligh/dark) schedule and provided with food (Purina 500 rat chow) and water ad libirum. Treatment for all studies began 1 day after the animals arrival and dosed 5 or 7 days per week as indicated for 6 weeks. A group of age matched sham operated rats not receiving any treatment served as an intact, estrogen replete control group for each study. All treatments were prepared in 1% tween 80 in normal saline at defined concentrations so that the treatment volume was 0.1 mL/100 g body weight. 17-beta estradiol was dissolved in corn oil (20 uG/mL) and delivered subcutaneously, 0.1 mL/rat. All dosages were adjusted at three week intervals according to group mean body weight measurements.

Five weeks after the initiation of treatment and one week prior to the termination of the study, each rat was evaluated for bone mineral density (BMD). The BMD's of the proximal tibiae (PT) and fourth lumbar vertabrae (L4) were measured in anesthetized rats using a dual energy X-ray absorptiometer (Eclipse XR-26, Norland Corp. Ft. Atkins, Wis.). The dual energy X-ray absorptiometer (DXA) measurements for each rat were performed as follows: Fifteen minutes prior to DXA measurements, the rat was anesthetized with an intraperitoneal injection of 100 mg/kg ketamine (Bristol Laboratories, Syracuse, N.Y.) and 0.75 mg/kg acepromazine (Aveco, Ft.Dodge, Iowa). The rat was placed on an acrylic table under the DXA scanner perpendicular to its path; the limbs were extended and secured with paper tape to the surface of the table. A preliminary scan was performed at a scan speed of 50 mm/second with a scan resolution of 1.5 mm×1.5 mm to determine the region of interest in PT and L4. Small subject software was employed at a scan speed of 10 mm/second with resolution of 0.5 mm×0.5 mm for final BMD measurements. The software allows the operator to define a 1.5 cm wide area to cover the total length of L4. The BMDs for respective sites were computed by the software as a function of the attenuation of the dual beam (46.8 KeV and 80 KeV) X-ray generated by the source underneath the subject and the detector travelling along the defined area above the subject. The data for BMD values (expressed in g/cm2) and individual scans were stored for statistical analysis.

One week after BMD evaluation the rats were sacrificed by carbon dioxide suffocation and blood collected for cholesterol determination. The uteri were removed and the weights taken. Total cholesterol is determined using a Boehringer-Mannheim Hitachi 911 clinical analyzer using the Cholesterol/HP kit. Statirstics were compared using one-way analysis of variance with Dunnet's test.

TABLE 18

6-Week Ovariectomized Rat Study Of Example No. 98

| Treatment | BMD (mg/cm$^2$)[a,b] | | Δ Body Weight (g)[a,c] | Uterine Weight (mg)[a,c] | Cholesterol (mg/dl)[a,c] |
|---|---|---|---|---|---|
| | Proximal Tibia | $L_i$ | | | |
| Study[d] | | | | | |
| Sham (Intact) | 0.211** ± 0.003 | 0.183* ± 0.003 | 43.0* ± 6.0 | 426.4** ± 25.0 | 71.6** ± 5.0 |
| Vehicle (Ovx) | 0.189 ± 0.004 | 0.169 ± 0.004 | 62.7 ± 8.2 | 118.2 ± 7.8 | 87.2 ± 3.0 |
| Example No. 98 | | | | | |
| 0.3 mg/kg, p.o. | 0.210** ± 0.003 | 0.173 ± 0.003 | 46.8 ± 6.6 | 149.3 ± 4.4 | 59.0** ± 2.2 |
| Raloxifene 3 mg/kg, p.o. | 0.207** ± 0.006 | 0.170 ± 0.003 | 25.3** ± 5.4 | 191.6** ± 9.3 | 55.0** ± 2.4 |
| 17β-Estradiol 2 μg/rat, s.c. | 0.224** ± 0.004 | 0.169 ± 0.004 | 33.1** ± 4.9 | 426.0** ± 18.4 | 95.5 ± 3.9 |

[a]Mean ± SEM
[b]Following 5 weeks of treatment
[c]Following 6 weeks of treatment
[d]Daily treatment x7 days/week x6 weeks
*p < 0.05 vs corresponding Vehicle value
**p < 0.01 vs corresponding Vehicle value

What is claimed:

1. A method of treating or inhibiting osteoarthritis in a mammal in need thereof, which comprises administering to said mammal an effective amount of a compound of formula I or II, having the structures

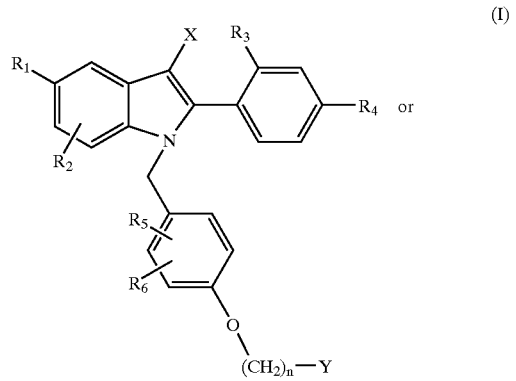

(I)

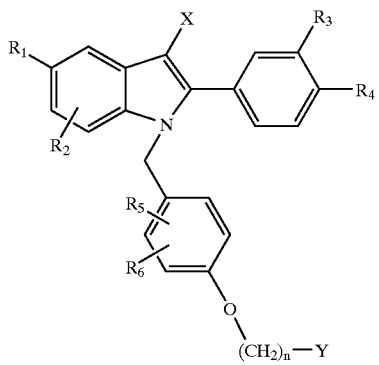

(II)

wherein:
$R_1$ is selected from H, OH or the $C_1$–$C_{12}$ esters (straight chain or branched) or $C_1$–$C_{12}$ (straight chain or branched or cyclic) alkyl ethers thereof, or halogens; or $C_1$–$C_4$ halogenated ethers including triflouromethyl ether and trichloromethyl ether;

$R_2$, $R_3$, $R_4$, $R_5$, and $R_6$ are independently selected from H, OH or the $C_1$–$C_{12}$ esters (straight chain or branched) or $C_1$–$C_{12}$ alkyl ethers (straight chain or branched or cyclic) thereof, halogens, or $C_1$–$C_4$ halogenated ethers including triflouromethyl ether and trichloromethyl ether, cyano, $C_1$–$C_6$ alkyl (straight chain or branched), or trifluoromethyl, with the proviso that, when $R_1$ is H, $R_2$ is not OH;

X is selected from H, $C_1$–$C_6$ alkyl, cyano, nitro, trifluoromethyl, halogen;

n is 2 or 3;

Y is selected from:
a) the moiety:

wherein $R_7$ and $R_8$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —CF$_3$, or —OCF$_3$;

b) a five-membered saturated, unsaturated or partially unsaturated heterocycle containing up to two heteroatoms selected from the group consisting of —O—, —NH—, —N($C_1C_4$ alkyl)—, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —CO$_2$H—, —CN—, —CONHR$_1$—, —NH$_2$—, $C_1$–$C_4$ alkylamino, di($C_1$–$C_4$)alkylamino, —NHSO$_2$R$_1$—, —NHCOR$_1$—, —NO$_2$, and phenyl optionally substituted with 1–3 ($C_1$–$C_4$)alkyl;

c) a six-membered saturated, unsaturated or partially unsaturated heterocycle containing up to two heteroatoms selected from the group consisting of —O—, —NH—, —N($C_1C_4$ alkyl)—, —N=, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl;

d) a seven-membered saturated, unsaturated or partially unsaturated heterocycle containing up to two heteroatoms selected from the group consisting of —O—, —NH—, —N(C$_1$C$_4$ alkyl)—, —N=, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl; or e) a bicyclic heterocycle containing from 6–12 carbon atoms either bridged or fused and containing up to two heteroatoms selected from the group consisting of —O—, —NH—, —N(C$_1$C$_4$ alkyl)—, and —S(O)$_m$—, wherein m is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H—, —CN—, —CONHR$_1$—, —NH$_2$—, C$_1$–C$_4$ alkylamino, di(C$_1$–C$_4$)alkylamino, —NHSO$_2$R$_1$—, —NHCOR$_1$—, —NO$_2$, and phenyl optionally substituted with 1–3 (C$_1$–C$_4$)alkyl;

or a pharmaceutically acceptable salt thereof.

2. The method according to claim 1 wherein:

R$_1$ is selected from H, OH or the C$_1$–C$_4$ esters or alkyl ethers thereof, halogen;

R$_2$, R$_3$, R$_4$, R$_5$, and R$_6$ are independently selected from H, OH or the C$_1$–C$_4$ esters or alkyl ethers thereof, halogen, cyano, C$_1$–C$_6$ alkyl, or trifluoromethyl, with the proviso that, when R$_1$ is H, R$_2$ is not OH;

X is selected from H, C$_1$–C$_6$ alkyl, cyano, nitro, triflouromethyl, halogen;

Y is the moiety

R$_7$ and R$_8$ are selected independently from H, C$_1$–C$_6$ alkyl, or combined by —(CH$_2$)$_p$—, wherein p is an integer of from 2 to 6, so as to form a ring, the ring being optionally substituted by up to three substituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$), —NH$_2$, C$_1$–C$_4$ alkylamino, di(C$_1$–C$_4$)alkylamino, —NHSO$_2$(C$_1$–C$_4$), —NHCO (C$_1$–C$_4$), and —NO$_2$;

or a pharmaceutically acceptable salt thereof.

3. The method according to claim 1 wherein:

R$_1$ is OH;

R$_2$, R$_3$, R$_4$, R$_5$, and R$_6$ are independently selected from H, OH or the C$_1$–C$_4$ esters or alkyl ethers thereof, halogen, cyano, C$_1$–C$_6$ alkyl, or trifluoromethyl, with the proviso that, when R$_1$ is H, R$_2$ is not OH;

X is selected from the group of Cl, NO$_2$, CN, CF$_3$, or CH$_3$;

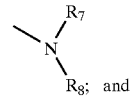

R$_7$ and R$_8$ are concatenated together as —(CH$_2$)$_r$, wherein r is an integer of from 4 to 6, to form a ring optionally substituted by up to three subsituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO2H, —CN, —CONH (C$_1$–C$_4$), —NH$_2$, C$_1$–C$_4$ alkylamino, di(C$_1$–C$_4$) alkylamino, —NHSO$_2$(C$_1$–C$_4$), —NHCO(C$_1$–C$_4$), and —NO$_2$;

or a pharmaceutically acceptable salt thereof.

4. The method according to claim 1, wherein the compound is 1-[4-(2-azepan-1-yl-ethoxy)-benzyl]-2-(4-hydroxy-phenyl)-3-methyl-1H-indol-5-ol or a pharmaceutically acceptable salt thereof.

5. The method according to claim 1, wherein the compound is 2-(4-hydroxy-phenyl)-3-methyl-1-[4-(2-piperidin-1-yl-ethoxy)-benzyl]-1H-indol-5-ol or a pharmaceutically acceptable salt thereof.

* * * * *

UNITED STATES PATENT AND TRADEMARK OFFICE
CERTIFICATE OF CORRECTION

PATENT NO. : 6,951,852 B2
APPLICATION NO. : 10/692777
DATED : October 4, 2005
INVENTOR(S) : Chris P. Miller et al.

It is certified that error appears in the above-identified patent and that said Letters Patent is hereby corrected as shown below:

Column 1,
Line 56, replace "antiestmgen," with -- antiestrogen, --;

Column 2,
Line 1, replace "1998," with -- 1997, --;

Column 4,
Line 51, replace "$(C_1-C)$" with -- $(C_1-C_4)$ --;

Column 5,
Line 41, replace "subsituents" with -- substituents --;

Column 6,
Line 22, replace "ration" with -- reaction --;

Column 18,
Line 40, replace "form" with -- from --;

Column 22,
Line 30, replace "conveniantly" with -- conveniently --;
Line 31, replace "stating" with -- starting --;

Column 25,
Line 3, replace "1610 cm$^{31\ 1}$;" with -- 1610 cm$^{-1}$; --;
Line 36, replace "EI" with -- eI --;

Column 29,
Line 20, replace "750-7.40" with -- 7.50-7.40 --;

Column 32,
Line 49, replace "matogrphed" with -- matographed --;

Column 34,
Line 15, replace "J=8.8 Hz)," with -- J=8.3 Hz) --;
Line 62, replace "8.8" with -- 8.3 --;

Column 36,
Line 26, replace "g, 87 mmol)." with -- g, 8.7 mmol). --;

Column 37,
Line 65, replace "(Kr)" with -- (KBr) --;

UNITED STATES PATENT AND TRADEMARK OFFICE
CERTIFICATE OF CORRECTION

PATENT NO.      : 6,951,852 B2
APPLICATION NO. : 10/692777
DATED           : October 4, 2005
INVENTOR(S)     : Chris P. Miller et al.

It is certified that error appears in the above-identified patent and that said Letters Patent is hereby corrected as shown below:

Column 38,
Line 7, replace "(d, 2H," with -- (t, 2H, --;

Column 40,
Line 7, replace "7.25" with -- 7.28 --;

Column 43,
Line 46, replace "MaSO$_4$ and column chromatogaphed" with -- MgSO$_4$ and column chromatographed --;

Column 44,
Line 9, delete "of product";
Lines 54 and 65, replace "J=8.8" with -- J=8.3 --;

Column 45,
Line 15, replace "J=65 Hz, J=24 Hz)," with -- J=6.5 Hz, J=2.4 Hz), --;
Line 31, replace "{4-[2-(3-" with -- {4-[2-(2- --;

Column 47,
Line 57, replace "clcd" with -- calcd --;
Line 63, replace "-1-(4-(2" with -- 1-[4-(2 --;

Column 48,
Line 63, replace "1-[4-(3-" with -- 1-[4-(2- --;

Column 54,
Line 50, replace "1:0)" with -- 1:10) --;

Column 56,
Line 9, replace "1H" with -- $^1$H --;
Line 16, replace "C$_{29}$H$_{32}$N$_2$O+1HC1" with -- C$_{29}$H$_{32}$N$_2$O$_2$+1HC1 --;
Line 33, replace "-yl)-" with -- -1-yl)- --;
Line 47, replace "4-[2(piperidin-1-" with -- 4-[2-(piperidin-1- --;
Line 54, replace "(m, 2H," with -- (t, 2H --;

UNITED STATES PATENT AND TRADEMARK OFFICE
CERTIFICATE OF CORRECTION

PATENT NO. : 6,951,852 B2
APPLICATION NO. : 10/692777
DATED : October 4, 2005
INVENTOR(S) : Chris P. Miller et al.

It is certified that error appears in the above-identified patent and that said Letters Patent is hereby corrected as shown below:

Column 57,
Line 7, replace "(2Azepan" with -- (2-Azepan --;
Line 35, replace "phenyl-3" with -- phenyl)-3 --;
Line 51, replace "713" with -- 7.23 --;
Line 60, replace "indol5" with -- indol-5 --;

Column 58,
Line 11, replace "(nm, 2H)" with -- m, 2H) --;
Line 13, replace "EXAMPLE NO. 98" with -- EXAMPLE NO. 97 --;
Line 22, replace "3.43-3.30" with -- 3.48-3.30 --;

Column 59,
Line 35, replace "508" with -- 5.08 --;
Line 67, replace "$C_{30H34}N_2O_3$" with -- $C_{30}H_{34}N_2O_3$ --;

Column 60,
Line 40, replace "210-1.99 (m, 2H), 1.46 (, 2H," with -- 2.10-1.99 (m, 2H), 1.46 (t, 2H, --;
Line 55, replace "cm-1;" with -- $cm^{-1}$; --;

Column 61,
Line 11, replace "indnol" with -- indol --;
Line 18, replace "$[N+H]^+$;" with -- $[M+H]^+$; --;

Column 62,
Line 5, replace "N2O$_4$" with -- $N_2O_4$ --;
Line 40, replace "7.6-7.23" with -- 7.26-7.23 --;

Column 63,
Line 32, replace "$C_{39}$" with -- $C_{29}$ --;
Line 55, replace "659-6.56" with -- 6.59-6.56 --;

Column 66,
Line 62, replace "N-(4Benzyloxy" with -- N-(4-Benzyloxy --;

Column 67,
Line 9, replace "triration" with -- tituration --;
Line 50, replace "phenoxyl}-asetic" with -- phenoxy}-acetic --;

UNITED STATES PATENT AND TRADEMARK OFFICE
CERTIFICATE OF CORRECTION

PATENT NO.        : 6,951,852 B2
APPLICATION NO.   : 10/692777
DATED             : October 4, 2005
INVENTOR(S)       : Chris P. Miller et al.

It is certified that error appears in the above-identified patent and that said Letters Patent is hereby corrected as shown below:

Column 68,
Line 23, replace "3-chloro" with -- )-3-chloro --;

Column 69,
Line 11, replace "(m, 4H)" with -- (bm, 4H) --;
Line 18, replace "or" with -- of --;

Column 70,
Line 20, replace "indnol" with -- indol --;
Line 33, replace "-7-(4-" with -- -2-(4- --;

Column 71,
Scheme 15, replace:

" 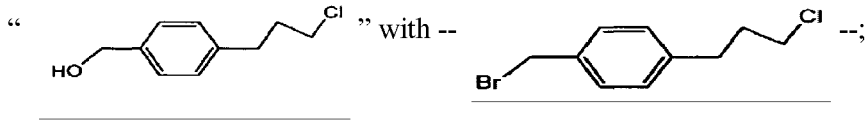 " with -- --;

Column 72,
Scheme 15, replace:

" 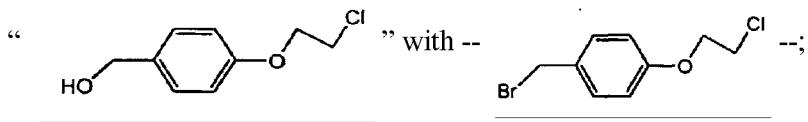 " with -- --;

Line 49, replace "benzytalcohol" with -- benzylalcohol --;

Column 73,
Line 4, replace "(2-Chloroethoxy" with -- 4-(2-Chloroethoxy --;
Line 41, replace "-2-benzyloxy-phenyl" with -- -2-(4-benzyloxy-phenyl- --;
Line 47, replace "308-3.00" with -- 3.08-3.00 --;
Line 55, replace "convened" with -- converted --;

Column 77,
Line 62, replace "-3-metyl-1H-indole No. 7 (65 g, 15.5 mmol)" with -- -3-methyl-1H-indole No. 7 (6.5 g, 15.5 mmol) --;

Column 78,
Line 51, replace "[3-piperidin" with -- [3-(piperidin --;
Line 67, replace "cm-1" with -- $cm^{-1}$ --;

UNITED STATES PATENT AND TRADEMARK OFFICE
CERTIFICATE OF CORRECTION

PATENT NO. : 6,951,852 B2
APPLICATION NO. : 10/692777
DATED : October 4, 2005
INVENTOR(S) : Chris P. Miller et al.

It is certified that error appears in the above-identified patent and that said Letters Patent is hereby corrected as shown below:

Column 81,
Line 40, replace "Mp+=56" with -- Mp=56 --;

Column 83,
Line 46, replace "treading" with -- treating --;

Column 94,
Line 1, before "94" add -- Method 17 --;
Line 45, replace "a" with -- alkaline --;
Line 47, delete the second occurrence of "as";

Column 95,
Line 39, replace "CaC12" with -- $CaCl_2$ --;

Column 96,
Line 40, replace "functionary" with -- functionally --;

Column 98,
Line 28, replace "room" with -- room on a --;

Column 99,
Line 13, replace "Statirstics" with -- Statistics --;

Column 102,
After line 27, add -- Y is the moiety --.

Signed and Sealed this

Fourth Day of July, 2006

JON W. DUDAS
*Director of the United States Patent and Trademark Office*